(12) United States Patent
Uhland et al.

(10) Patent No.: US 11,542,329 B2
(45) Date of Patent: Jan. 3, 2023

(54) ANTIBODIES TARGETING GLYCOPROTEIN VI

(71) Applicant: MORPHOSYS AG, Planegg (DE)

(72) Inventors: Kerstin Uhland, Planegg (DE); Julia Neugebauer, Munich (DE); Steffen Runz, Munich (DE)

(73) Assignee: Morphosys AG, Planegg (DE)

( * ) Notice: Subject to any disclaimer, the term of this patent is extended or adjusted under 35 U.S.C. 154(b) by 96 days.

(21) Appl. No.: 17/055,528

(22) PCT Filed: May 15, 2019

(86) PCT No.: PCT/EP2019/062522
§ 371 (c)(1),
(2) Date: Nov. 13, 2020

(87) PCT Pub. No.: WO2019/219765
PCT Pub. Date: Nov. 21, 2019

(65) Prior Publication Data
US 2021/0214435 A1    Jul. 15, 2021

(30) Foreign Application Priority Data
May 16, 2018    (EP) .................................. 18172736

(51) Int. Cl.
*C07K 16/28* (2006.01)
*A61P 7/02* (2006.01)
*A61K 39/00* (2006.01)

(52) U.S. Cl.
CPC ............ *C07K 16/2803* (2013.01); *A61P 7/02* (2018.01); *A61K 2039/505* (2013.01); *C07K 2317/55* (2013.01); *C07K 2317/565* (2013.01)

(58) Field of Classification Search
None
See application file for complete search history.

(56) References Cited

U.S. PATENT DOCUMENTS

| 6,180,370 | B1 * | 1/2001 | Queen | ..................... | A61P 31/12 |
| | | | | | 435/69.6 |
| 10,842,870 | B2 * | 11/2020 | Billiald | ................. | C07K 16/28 |

FOREIGN PATENT DOCUMENTS

| WO | WO 2003/054020 A2 | 7/2003 |
| WO | WO 2011/073954 A2 | 6/2011 |
| WO | WO 2017/021539 A2 | 2/2017 |
| WO | WO 2018/087349 A1 | 5/2018 |

OTHER PUBLICATIONS

Janeway, A. C., et al. "Immunobiology: the immune system in health and disease. London." Current Biology (1997): 3:1-3:11. (Year: 1997).*
Kipriyanov, Sergey M., and Fabrice Le Gall. "Generation and production of engineered antibodies." Molecular biotechnology 26.1 (2004): 39-60. (Year: 2004).*
Kristell Lebozec et al: "Design, development and characterization of ACT017, a humanized Fab that blocks platelet's glycoprotein VI function without causing bleeding risks", MABS, Jul. 12, 2017, 9:6, 945-958; XP055389636, US ISSN: 1942-0862, DOI: 10.1080/19420862.2017.1336592—Exhibit 5.
Smethurst P A et al: "Identification of the primary collagen-binding surface on human glycoprotein VI by site-directed mutagenesis and by a blocking phage antibody", Blood, American Society of Hematology, US, vol. 103, No. 3, Feb. 1, 2004, pp. 903-911, XP002383117, ISSN: 0006-4971, DOI: 10.1182/BLOOD-2003- 01-0308—Exhibit 6.
Qian M D et al: "Anti GPVI human antibodies neutralizing collagen-induced platelet aggregation isolated from a combinatorial phage display library", Human Antibo, IOS Press, Amsterdam, NL, vol. 11, No. 3, Jan. 1, 2002, pp. 97-105, XP009056880, ISSN: 1093-2607—Exhibit 7.
Isuru Induruwa et al: "Beyond antiplatelets: The role of glycoprotein VI in ischemic stroke", International Journal of Stroke, vol. 11, No. 6, Jul. 9, 2016, pp. 618-625, XP055510399, ISSN: 1747-4930, DOI: 10.1177/1747493016654532—Exhibit 8.

* cited by examiner

*Primary Examiner* — Michael Szperka
*Assistant Examiner* — Lia E Taylor
(74) *Attorney, Agent, or Firm* — Adriano & Associates

(57) ABSTRACT

The present disclosure provides antibodies or antibody fragments specific for GPVI. In particular, it relates to antibodies or antibody fragments that have combined beneficial properties and are therefore useful for the treatment or prophylaxis of GPVI related disorders or conditions, such as for example thrombotic or vascular disorders.

18 Claims, 10 Drawing Sheets

Specification includes a Sequence Listing.

ANTIBODIES TARGETING GLYCOPROTEIN VI

This subject application claims priority under 35 U. S. C, § 371 to PCT Application No. PCT/EP2019/062522, filed May 15, 2019, which claims the benefit of European Patent Application 18172736.3, filed May 16, 2018. The contents of these applications are incorporated by reference in their entireties here.

FIELD OF THE INVENTION

The present application relates to antibodies or antibody fragments (such as Fabs) which bind to Glycoprotein VI (GPVI). The present disclosure also relates to nucleic acids, vectors and host cells capable of expressing said antibodies or antibody fragments, pharmaceutical compositions comprising said antibodies or antibody fragments and uses of said antibodies or antibody fragments for the treatment of specific disorders.

BACKGROUND

Platelet activation is of fundamental importance in the development of arterial thrombosis and cardiovascular disorders. Patients suffering from such disorders are commonly treated with antiplatelet drugs which interfere with thrombus formation through targeting late events in this process. A serious side effect of these drugs is prolonged bleeding which limits their use.

GPVI is a major collagen receptor expressed exclusively on platelets and megakaryocytes. Binding of GPVI to collagen (which is one of the most important thrombogenic components of the subendothelial matrix (Lockyer S. et al, Thromb Res. 2006; 1 18(3):371-80)) induces receptor clustering and subsequent platelet activation. As such, GPVI is of central importance in early events of platelet activation, and therefore a major target for the interference with this mechanism (Nieswandt B and Watson S P, Blood. 2003 Jul. 15; 102(2):449-61).

The antiplatelet and antithrombotic effects of GPVI have been described in in vitro and in vivo studies, using platelets from mice and human. For instance, GPVI deficient platelets does not respond to collagen. Moreover, mouse deficient for GPVI revealed an effective inhibition of arterial thrombus formation at the damaged vessel wall without increasing the susceptibility to spontaneous bleeding. All these data indicate that GPVI is an effective and safe target for the treatment of thrombotic and vascular disorders in human.

Inhibitory or neutralizing monoclonal antibodies directed against GPVI being able to interfere with GPVI—collagen interaction has been described in the prior art. See e.g. EP1224942 (EP1228768) (Nieswandt, Bernhard), WO2001/000810 (MILLENNIUM PHARMACEUTICALS), WO2003/054020A3 (CAMBRIDGE UNIVERSITY TECHNICAL SERVICES LTD, GB), EP1538165A1 (Procorde GmbH/GSF-Forschungszentrum für Umwelt und Gesundheit GmbH), WO2005/111083 (EP1745076B1) (OTSUKA PHARMACEUTICAL CO., LTD.), WO2006/118350 (EP1876240) (MOCHIDA PHARMACEUTICAL CO. LTD., JP), WO2008/049928 (INSTITUT NATIONAL DE LA SANTE ET DE LA RECHERCHE MEDICALE (INSERM), FR), WO2011/073954 (SANOFI).

However, the majority of the reported GPVI specific antibodies seems to be not suited for the clinical development and therapeutic use in human, especially due to their animal origin (which makes them immunogenic in human patients), lack of cross-reactivity to relevant animal species, their considerably weak affinity, their short half-life or because of unfavorable functional properties, such as inducing GPVI depletion from the surface of platelets. GPVI depletion can be indicative for receptor activation and since it cannot be controlled and is irreversible it should be avoided.

Currently, only one GPVI specific monoclonal Fab antibody ACT-017 (see WO2017/021539) seems to be under clinical development for the treatment of ischemic stroke. However, this antibody is a humanized version of the earlier disclosed antibody 9012.2 (see WO 2001000810) and as such lacks cross-reactivity to rodent GPVI, which are commonly used relevant models for in vivo studies. In addition, ACT-017 bears the risk of being recognized by anti-Fab antibodies present in a patient's serum, due to its structure at the C-terminus of the Fab heavy chain. Such immune response could result in an undesired restoration of bivalent GPVI binding and GPVI activation in platelets.

There is thus a need for further improved antibodies or antibody fragments specific for GPVI suited for clinical development and therapeutic use showing better affinity, efficacy and safety profiles in human as compared to the neutralizing antibodies of the prior art.

Accordingly, the present disclosure provides novel antibodies and antibody fragments (in particular Fab fragments) which are superior to the GPVI specific antibodies known from the prior art. In particular, the antibodies of the present disclosure are human antibodies or antibody fragments which also binds to non-human primate (such as cynomolgus monkey) as well as rodent (such as rat and/or mouse) GPVI, display high affinities and combine favorable functional and safety properties never have been observed before.

In this respect, the GPVI specific antibody fragments of the present disclosure may also comprise a modification at the C-terminus of the Fab heavy chain (e.g. a modified heavy chain constant region). The inventors of the present application demonstrated that such modification can further reduce the ability of the Fab to induce platelet activation via cross-linking of GPVI on the surface of platelets by preventing the recognition of the Fab by (pre-existing) anti-Fab antibodies present in a patient' serum. As outlined above, such recognition may result in the restoration of bivalent or multivalent GPVI-binding, leading to GPVI clustering on the surface of platelets, similar to the activity of its natural agonist ligands, such as collagen.

Accordingly, the GPVI specific antibodies of the present disclosure offer a particular safe treatment of ischemic events.

These features makes the antibodies and antibody fragments of the present disclosure highly desirable for therapeutic use such as for preventing and/or treating thrombotic and vascular disorders.

SUMMARY OF THE INVENTION

The present disclosure provides novel antibodies or antibody fragments. Specifically, the present invention provides antibody or antibody fragment specific for GPVI, wherein said antibody or antibody fragment comprises
  a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO: 27, or c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region of SEQ ID NO: 49.

The present invention is based on the recognition that a modified constant heavy chain in a novel sequence of an GPVI specific antibody or antibody fragment of the present invention provides human antibodies or antibody fragments having reduced immunogenicity. Moreover, the antibodies or antibody fragments which are disclosed herein bind to human GPVI and also bind to GPVI from cynomolgus monkey, mouse and rat.

The antibodies or antibody fragments of the present disclosure neutralize the activity of GPVI.

In addition, the disclosed antibodies or antibody fragments inhibit binding of human, mouse, and cynomolgus monkey GPVI to collagen with an $IC_{50}$ concentration of 27 nM or less. In a preferred embodiment, the disclosed antibodies or antibody fragments inhibit binding of human, mouse, and cynomolgus monkey GPVI to collagen with an $IC_{50}$ concentration of 9 nM or less. In addition, the disclosed antibodies or antibody fragments inhibit collagen-induced platelet aggregation.

As disclosed and exemplified herein, these antibodies or antibody fragments proved to be effective in an in vivo mouse model of thrombosis.

Accordingly, the antibodies or antibody fragments of the present disclosure are superior in terms of effectiveness and provide well suited and promising compounds for the treatment of humans suffering for example, from thrombotic or vascular disorders.

The present disclosure provides antibodies or antibody fragments that bind to human GPVI having CDR regions according to Tables 1-4 disclosed herein.

The present disclosure also provides antibodies or antibody fragments having a variable heavy chain (VH) and a variable light chain (VL) according to Tables 1-4 disclosed herein.

The present disclosure also provides antibodies or antibody fragments having a heavy chain (HC) and a light chain (LC) according to Tables 1-4 disclosed herein.

The present disclosure also provides antibodies or antibody fragments according to the present disclosure, wherein said antibody or antibody fragment is a Fab.

The present disclosure also provides Fabs comprising a modified heavy chain constant region as disclosed herein, wherein the modified heavy chain constant region prevents or inhibits recognition of said antibodies or antibody fragments by anti-Fab antibodies present in a subject's serum.

The present disclosure also provides antibodies or antibody fragments which compete with the antibodies or antibody fragments specific for GPVI disclosed herein.

The present disclosure also provides antibodies or antibody fragments which bind to the same epitope as the antibodies or antibody fragments specific for GPVI disclosed herein.

The present disclosure also provides the isolated antibodies or antibody fragments specific for GPVI according to the present disclosure for use in medicine.

The present disclosure also provides methods for treating a subject suffering from a disorder, such as a thrombotic or vascular disorder, by administering to said subject an effective amount of an antibody or antibody fragment specific for GPVI of the present disclosure. Preferably said subject or patient is a human.

The present disclosure also provides pharmaceutical compositions comprising the isolated antibodies or antibody fragments specific for GPVI of the present disclosure, and a pharmaceutically acceptable carrier or excipient.

The present disclosure also provides nucleic acid compositions encoding the antibodies or antibody fragments specific for GPVI of the present disclosure.

The present disclosure also provides vector compositions comprising nucleic acid compositions encoding the antibodies or antibody fragment antibodies specific for GPVI of the present disclosure.

The present disclosure also provides host cells comprising vector or nucleic acid compositions encoding the antibodies or antibody fragments specific for GPVI of the present disclosure.

There is utility in the claimed antibodies or antibody fragments. Furthermore, there is utility in the claimed method to identify such antibodies or fragments. Utilization of the claimed antibodies or antibody fragments is to alter the biological activity of human GPVI.

In particular, the claimed antibodies or antibody fragments are for therapeutic use, such as the treatment of thrombotic or vascular disorders.

BRIEF DESCRIPTION OF THE FIGURES

FIG. 4E) Inhibition by a combination of acetylsalicylacid (ASA) and Ticagrelor; FIG. 4F) Inhibaition by negative control Fab. Data points were recorded as 1 frame per second. Shown are average values for each data point (black)+SD (grey) from experiments with blood samples from 14 donors.

DETAILED DESCRIPTION OF THE INVENTION

Figure 1:
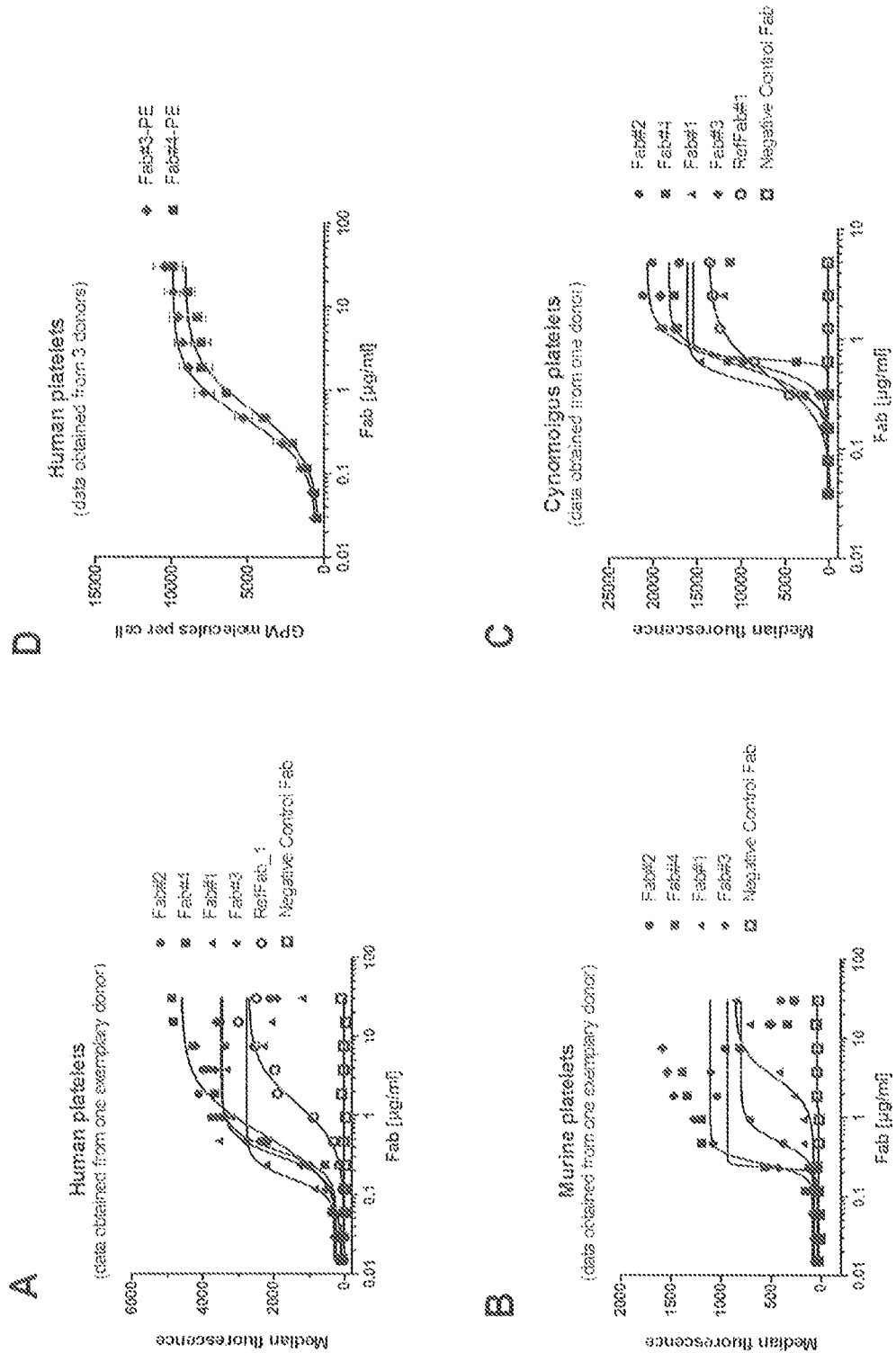
FIG. 1: A-D) Binding of Fab #1, Fab #2, Fab #3, Fab #4 (comprising a modified heavy chain constant region) to GPVI expressed on the cell surface of human, cynomolgus monkey and mouse platelets obtained from Platelet-rich plasma (PRP) from up to 3 donors. Shown are results for one exemplary donor (FIGS. 1A, 1B and 1C) or the average±standard deviation (SD) of 3 donors (FIG. 1D).

The disclosure pertains to a number of antibodies or antibody fragments that recognize human GPVI.

Definitions

The term "GPVI" refers to a protein known as Glycoprotein VI.

```
Human GPVI-1A (1-339) has the amino acid sequence
of (Uniprot: Q9HCN6-1, haplotype 'a')
                                        (SEQ ID NO: 1)
MSPSPTALFCLGLCLGRVPAQSGPLPKPSLQALPSSLVPLEKPVTLRCQG

PPGVDLYRLEKLSSSRYQDQAVLFIPAMKRSLAGRYRCSYQNGSLWSLPS

DQLELVATGVFAKPSLSAQPGPAVSSGGDVTLQCQTRYGFDQFALYKEGD

PAPYKNPERWYRASFPIITVTAAHSGTYRCYSFSSRDPYLWSAPSDPLEL

VVTGTSVTPSRLPTEPPSSVAEFSEATAELTVSFTNKVETTETSRSITTS

PKESDSPAGPARQYYTKGNLVRICLGAVILIILAGFLAEDWHSRRKRLRH

RGRAVQRPLPPLPPLPLTRKSNGGQDGGRQDVHSRGLCS

Signal peptide/Extracellular Domain/Transmembrane
and cytoplasmic domains
Cynomolgus monkey GPVI (1-318) has the amino
acid sequence of (UniProt B0I1T7):
                                        (SEQ ID NO: 2)
MSPSPTTLFCLGLCLGHVPAQRGPLPKPSLQALPSSLVPLEKPVTLRCQG

PPGVDLYRLEKLSSSRYQDQAVLFIPAMKRHLAGRYRCSYQNGSLWSPPS

DQLELVATGVFAKPSLSAQPGPAVSSGGDVTLQCQTRYGFDQFALYKEGD

PAPYKNPERWYRASFPIITVTAAHSGTYRCYSFSSGDPYLWSAPSDPLEL

MVTEFSEATTELTVSLTNKVFTTETSRSITASPKEPGSPAGPARQYYTKG

NLVRICLGAVILILLAGFLAEDWHSRRKRLRHRVRAVQRPLPPLPPTRKS

HGDQDGGRPDVHSRGLCS

Murine GPVI (1-313) has the amino acid sequence
of (UniProt P0C191):
                                        (SEQ ID NO: 3)
MSPASPTFFCIGLCVLQVIQTQSGPLPKPSLQAQPSSLVPLGQSVILRCQ

GPPDVDLYRLEKLKPEKYEDQDFLFIPTMERSNAGRYRCSYQNGSHWSLP

SDQLELIATGVYAKPSLSAHPSSAVPQGRDVTLKCQSPYSFDEFVLYKEG

DTGSYKRPEKWYRANFPIITVTAAHSGTYRCYSFSSSSPYLWSAPSDPLV

LVVTGLSATPSQVPTEESFPVTESSRRPSILPTNKISTTEKPMNITASPE

GLSPPFGFAHQHYAKGNLVRICLGATIIIILLGLLAEDWHSRKKCLQHRM

RALQRPLPPLPLA

The extracellular domain of human GPVI-1A (Position
21-269) has the amino acid sequence of (Uniprot:
Q9HCN6-1, haplotype 'a'):
                                        (SEQ ID NO: 4)
QSGPLPKPSLQALPSSLVPLEKPVTLRCQGPPGVDLYRLEKLSSSRYQDQ

AVLFIPAMKRSLAGRYRCSYQNGSLWSLPSDQLELVATGVFAKPSLSAQP

GPAVSSGGDVTLQCQTRYGEDQFALYKEGDPAPYKNPERWYRASFPIITV

TAAHSGTYRCYSFSSRDPYLWSAPSDPLELVVTGTSVTPSRLPTEPPSSV

AEFSEATAELTVSFTNKVFTTETSRSITTSPKESDSPAGPARQYYTKGN
```

The extracellular domain of human GPVI-1B (Position 21-269) has the amino acid sequence of (Uniprot: Q9HCN6-1, haplotype 'b'):

(SEQ ID NO: 5)
QSGPLPKPSLQALPSSLVPLEKPVTLRCQGPPGVDLYRLEKLSSSRYQDQ

AVLFIPAMKRSLAGRYRCSYQNGSLWSLPSDQLELVATGVFAKPSLSAQP

GPAVSSGGDVTLQCQTRYGFDQFALYKEGDPAPYKNPERWYRASFPIITV

TAAHSGTYRCYSFSSRDPYLWSAPSDPLELVVTGTSVTPSRLPTEPPSPV

AEFSEATAELTVSFTNEVFTTETSRSITASPKESDSPAGPARQYYTKGN

The extracellular domain of human GPVI-2A (Position 21-251) has the amino acid sequence of (Uniprot: Q9HCN6-2, haplotype 'a'):

(SEQ ID NO: 6)
QSGPLPKPSLQALPSSLVPLEKPVTLRCQGPPGVDLYRLEKLSSSRYQDQ

AVLFIPAMKRSLAGRYRCSYQNGSLWSLPSDQLELVATGVFAKPSLSAQP

GPAVSSGGDVTLQCQTRYGFDQFALYKEGDPAPYKNPERWYRASFPIITV

TAAHSGTYRCYSFSSRDPYLWSAPSDPLELVVTEFSEATAELTVSFTNKV

FITETSRSITTSPKESDSPAGPARQYYTKGN

The terms "GPVI-1" and "GPVI-2" refer to the published isotypes of GPVI. The suffixes "A" and "B" refer to the described high frequency allele "a" (comprising amino acids S219, K237, T249) and low frequency allele "b" (comprising amino acids Pro219, Glu237, Ala249), respectively (Joutsi-Korhonen et al., 2003).

The extracellular domain of human GPVI is composed of two Ig-like C2-type domains, namely the D1 domain and the D2 domain, linked by a hinge-interdomain. The D1 domain comprises amino acid residues 21 to 109 of SEQ ID NO: 1. The D2 domain comprises amino acid residues 114 to 207 of SEQ ID NO: 1

The extracellular domain of cynomolgus monkey GPVI (Position 21-249) has the amino acid sequence of (Uniprot: B0I1T7):

(SEQ ID NO: 7)
QRGPLPKPSLQALPSSLVPLEKPVTLRCQGPPGVDLYRLEKLSSSRYQDQ

AVLFIPAMKRHLAGRYRCSYQNGSLWSPPSDQLELVATGVFAKPSLSAQP

GPAVSSGGDVTLQCQTRYGEDQFALYKEGDPAPYKNPERWYRASFPIITV

TAAHSGTYRCYSFSSGDPYLWSAPSDPLELMVTEFSEATTELTVSLTNKV

FTTETSRSITASPKEPGSPAGPARQYYTK

The extracellular domain of mouse GPVI (Position 21-266) has the amino acid sequence of (Uniprot: P0C191):

(SEQ ID NO: 8)
QSGPLPKPSLQAQPSSLVPLGQSVILRCQGPPDVDLYRLEKLKPEKYEDQ

DFLFIPTMERSNAGRYRCSYQNGSHWSLPSDQLELIATGVYAKPSLSAHP

SSAVPQGRDVTLKCQSPYSFDEFVLYKEGDTGSYKRPEKWYRANFPIITV

TAAHSGTYRCYSFSSSSPYLWSAPSDPLVLVVTGLSATPSQVPTEESFPV

TESSRRPSILPTNKISTTEKPMNITASPEGLSPPEGFAHQHYAKGN

The extracellular domain of rat GPVI (Position 21-269) has the amino acid sequence of (Uniprot: XP_008757241.2):

(SEQ ID NO: 9)
QHGPLPKPSLQAQPSSLVPLGHPVTLRCLGPSDADLYRLEKVKPGKLIFI

DQDFLFIPIMEINNAGRYRCSYQNESHWSLPSDQLELIATGVYSKPSLSA

HPSSAIPPGRDVTLKCQSQYSFDEFVLYKEGDTRPYKRPEKWYRANFPVI

TVTAAHSGTYRCYSFSSSSPYLWSAPSDPLVVVVTGPSATPSQVPTEVPS

PMTEASRRPSMLLTNKISTTEKPMNITVSPEGPSPPFGFAHQHYAKGN

The human IgG1-Fc domain (K105-K330) used for the generation of GPVI-ECD-Fc fusion protein has the amino acid sequence of:

(SEQ ID NO: 10)
DIKTHTCPPCPAPELLGGPSVFLEPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLV

KGFYPSDIAVEWESNGQPENNYKTTPPVLDSDGSFELYSKLTVDKSRWQQ

GNVFSCSVMHEALHNHYTQKSLSLSPGK

The term "about" preceding a figure means plus or less 10% of the value of said figure.

The term "antibody" as used herein refers to a protein comprising at least two heavy (H) chains and two light (L) chains inter-connected by disulfide bonds which interacts with an antigen. Each heavy chain (HC) is comprised of a heavy chain variable region (abbreviated herein as VH) and a heavy chain constant region. The heavy chain constant region is comprised of three domains, CH1, CH2 and CH3. Each light chain (LC) is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass. Both the light and heavy chains are divided into regions of structural and functional homology.

The phrase "antibody fragment", as used herein, refers to one or more portions of an antibody that retain the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains; a Fab' fragment, a monovalent fragment consisting of the VL, VH, CL and CH1 domains and a N-terminal portion of the hinge region of an immunoglobulin; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1126-1136). Antibody fragments can be grafted into scaffolds based on polypeptides such as Fibronectin type III (Fn3) (see U.S. Pat. No. 6,703,199, which describes fibronectin polypeptide monobodies). Antibody fragments can be incorporated into single chain molecules comprising a pair of tandem Fv segments (VH-CH1-VH-CH1) which, together with complementary light chain polypeptides, form a pair of antigen-binding sites (Zapata et al., (1995) Protein Eng. 8:1057-1062; and U.S. Pat. No. 5,641,870).

As used herein, the term "hinge region" includes the region of an antibody heavy chain that joins the CH1 domain to the CH2 domain. Hinge regions can be subdivided into three distinct domains: upper, middle, and lower hinge domains (Roux et ah, J. Immunol. 1998 161:4083).

The term "CH1 domain" refers to the heavy chain constant domain of an antibody linking the variable domain to the hinge region. The term "CH1 domain" includes wildtype CH1 domains and one of its natural occurring allotypes as well as variants thereof.

A "human antibody" or "human antibody fragment", as used herein, includes antibodies and antibody fragments having variable regions in which both the framework and CDR regions are derived from sequences of human origin. Furthermore, if the antibody contains a constant region, the constant region also is derived from such sequences. Human origin includes, e.g., human germline sequences, or mutated versions of human germline sequences or antibody containing consensus framework sequences derived from human framework sequences analysis, for example, as described in Knappik et al., (2000) J Mol Biol 296:57-86). The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; Lazikani et al., (1997) J. Mol. Bio. 273:927-948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mol. Biol. 273:927-948. Human antibodies can also be isolated from synthetic libraries or from transgenic mice (e.g. xenomouse) provided the respective system yield in antibodies having variable regions in which both the framework and CDR regions are derived from sequences of human origin.

The term "chimeric antibody" or "chimeric antibody fragment" is defined herein as an antibody molecule which has constant antibody regions derived from, or corresponding to, sequences found in one species and variable antibody regions derived from another species. Preferably, the constant antibody regions are derived from, or corresponding to, sequences found in humans, and the variable antibody regions (e.g. VH, VL, CDR or FR regions) are derived from sequences found in a non-human animal, e.g. a mouse, rat, rabbit or hamster.

A "humanized antibody" or "humanized antibody fragment" is defined herein as an antibody molecule which has constant antibody regions derived from sequences of human origin and the variable antibody regions or parts thereof or only the CDRs are derived from another species. For example a humanized antibody can be CDR-grafted, wherein the CDRs of the variable domain are from a non-human origin, while one or more frameworks of the variable domain are of human origin and the constant domain (if any) is of human origin.

The term "isolated" refers to a compound, which can be e.g. an antibody or antibody fragment, that is substantially free of other antibodies or antibody fragments having different antigenic specificities. Moreover, an isolated antibody or antibody fragment may be substantially free of other cellular material and/or chemicals. Thus, in some embodiments, antibodies or antibody fragments provided are isolated antibodies or antibody fragments which have been separated from antibodies with a different specificity. An isolated antibody may be a monoclonal antibody or antibody fragment. An isolated antibody or antibody fragments may be a recombinant monoclonal antibody or antibody fragments. An isolated antibody or antibody fragment that specifically binds to an epitope, isoform or variant of a target may, however, have cross-reactivity to other related antigens, e.g., from other species (e.g., species homologs).

The term "recombinant antibody" or "recombinant antibody fragment", as used herein, includes all antibodies or antibody fragments that are prepared, expressed, created or segregated by means not existing in nature. For example antibodies isolated from a host cell transformed to express the antibody, antibodies selected and isolated from a recombinant, combinatorial human antibody library, and antibodies prepared, expressed, created or isolated by any other means that involve splicing of all or a portion of a human immunoglobulin gene, sequences to other DNA sequences or antibodies isolated from an animal (e.g., a mouse) that is transgenic or transchromosomal for human immunoglobulin genes or a hybridoma prepared therefrom. Preferably, such recombinant antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. A recombinant antibody may be a monoclonal antibody. In an embodiment, the antibodies and antibody fragment disclosed herein are isolated from the Ylanthia® antibody library as disclosed in U.S. Ser. No. 13/321,564 or U.S. Ser. No. 13/299,367, which both herein are incorporated by reference.

As used herein, the term "monoclonal antibody" or "monoclonal antibody fragment" refers to an antibody or antibody fragment that is derived from a single clone, including any eukaryotic, prokaryotic, or phage clone, and not the method by which it is produced. Monoclonal antibodies or antibody fragments as disclosed herein may be made by the hybridoma method as described in Kohler et a/.; Nature, 256:495 (1975) or may be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York).

As used herein the term "binds specifically to", "specifically binds to", is "specific to/for" or "specifically recognizes", or the like, refers to measurable and reproducible interactions such as binding between a target and an antibody or antibody fragment, which is determinative of the presence of the target in the presence of a heterogeneous population of molecules including biological molecules. For example, an antibody or antibody fragment that specifically binds to a target (which can be an antigen or an epitope of an antigen) is an antibody or antibody fragment that binds this target with greater affinity, avidity, more readily, and/or with greater duration than it binds to other targets. In certain embodiments, an antibody or antibody fragment specifically binds to an epitope on a protein that is conserved among the protein from different species. In another embodiment, specific binding can include, but does not require exclusive binding. The antibodies or antibody fragments disclosed herein specifically bind to human GPVI. Preferably, the disclosed antibodies or antibody fragments specific for human GPVI specifically bind to GPVI of another species, such as GPVI from mouse, rat and/or cynomolgus monkey. Even more preferred, the antibodies or antibody fragments disclosed herein are specific for human GPVI, cynomolgus monkey GPVI, mouse GPVI and rat GPVI. Methods for determining whether two molecules specifically bind are well known in the art and include, for example, a standard ELISA assay. The scoring may be carried out by standard color development (e.g. secondary antibody with horseradish peroxidase and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative can be more than 5-fold. Typically, determination of binding specificity is performed by using not a single reference antigen, but a set of three to five unrelated antigens, such as milk powder, BSA, transferrin or the like.

As used herein, the term "affinity" refers to the strength of interaction between the polypeptide and its target at a single site. Within each site, the binding region of the polypeptide interacts through weak non-covalent forces with its target at numerous sites; the more interactions, the stronger the affinity.

The term "$K_D$", as used herein, refers to the dissociation constant, which is obtained from the ratio of Kd to Ka (i.e. Kd/Ka) and is expressed as a molar concentration (M). KD values for antigen binding moieties like e.g. monoclonal antibodies can be determined using methods well established in the art. Methods for determining the KD of an antigen binding moiety like e.g. a monoclonal antibody are SET (soluble equilibrium titration) or surface plasmon resonance using a biosensor system such as a Biacore® system. In the present disclosure an antibody specific to GPVI typically has a dissociation rate constant (KD) (koff/kon) of less than $5\times10^{-2}$M, less than $1\times10^{-2}$M, less than $5\times1^{-3}$M, less than $1\times10^{-3}$M, less than $5\times10^{-4}$M, less than $1\times10^{-4}$M, less than $5\times10^{-5}$M, less than $1\times10^{-5}$M, less than $5\times10^{-6}$M, less than $1\times10^{-6}$M, less than $5\times10^{-7}$M, less than $1\times10^{-7}$M, less than $5\times10^{-8}$M, less than $1\times10^{-8}$M, less than $5\times10^{-9}$M, less than $1\times10^{-9}$M, less than $5\times10^{-10}$M, less than $1\times10^{-10}$M, less than $5\times10^{-11}$M, less than $1\times10^{-11}$M, less than $5\times10^{-12}$M, less than $1\times10^{-12}$M, less than $5\times10^{-13}$M, less than $1\times10^{-13}$M, less than $5\times10^{-14}$M, less than $1\times10^{-14}$M, less than $5\times10^{-15}$M, or less than $1\times10^{-15}$M or lower.

Compositions of the present disclosure may be used for therapeutic or prophylactic applications. The present disclosure, therefore, includes a pharmaceutical composition containing an antibody or antibody fragment as disclosed herein and a pharmaceutically acceptable carrier or excipient therefor. In a related embodiment, the present disclosure provides a method for treating a thrombotic or vascular disorder. Such method contains the steps of administering to a subject in need thereof an effective amount of the pharmaceutical composition that contains an antibody or antibody fragment specific for GPVI as described herein.

The present disclosure provides therapeutic methods comprising the administration of a therapeutically effective amount of an antibody or antibody fragment specific for GPVI as disclosed herein to a subject in need of such treatment. A "therapeutically effective amount" or "effective amount", as used herein, refers to the amount of an antibody or antibody fragment specific for GPVI necessary to elicit the desired biological response. In accordance with the present disclosure, the therapeutically effective amount is the amount of an antibody or antibody fragment specific for GPVI, necessary to treat and/or prevent (e.g. prophylactic) a disorder.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts PILR, e.g., in the fluid phase or colloidal phase, but also situations where the agonist or antagonist does not contact the cell or the receptor.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "$EC_{50}$" as used herein, refers to the concentration of an antibody or an antibody fragment which induces a response in an assay half way between the baseline and maximum. It therefore represents the antibody concentration at which 50% of the maximal effect is observed.

The term "$IC_{50}$" as used herein, refers to the concentration of an antibody or antibody fragment that inhibits a response in an assay half way between the maximal response and the baseline. It represents the antibody concentration that reduces a given response by 50%.

The terms "inhibition" or "inhibit" or "reduction" or "reduce" or "neutralization" or "neutralize" refer to a decrease or cessation of any phenotypic characteristic (such as binding, a biological activity or function) or to the decrease or cessation in the incidence, degree, or likelihood of that characteristic. The "inhibition", "reduction" or "neutralization" needs not to be complete as long as it is detectable using an appropriate assay. In some embodiments, by "reduce" or "inhibit" is meant the ability to cause a decrease of 20% or greater. In another embodiment, by "reduce" or "inhibit" is meant the ability to cause a decrease of 50% or greater. In yet another embodiment, by "reduce" or "inhibit" is meant the ability to cause an overall decrease of 75%, 85%, 90%, 95%, or greater.

The term "antagonistic" antibody or antibody fragment as used herein refers to an antibody or antibody fragment that interacts with GPVI and partially or fully inhibits or neutralizes a biological activity or function or any other phenotypic characteristic of GPVI.

"Cross competes" means the ability of an antibody or antibody fragment or other antigen-binding moieties to interfere with the binding of other antibodies, antibody fragments or antigen-binding moieties to a specific antigen in a standard competitive binding assay. The ability or extent to which an antibody, antibody fragment or other antigen-binding moieties is able to interfere with the binding of another antibody, antibody fragment or antigen-binding moieties to a specific antigen, and, therefore whether it can be said to cross-compete according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in International Patent Application No. WO 2003/48731. Cross-competition is present if the antibody or antibody fragment under investigation reduces the binding of one of the antibodies or antibody fragments disclosed in Tables 1-4 to GPVI by 60% or more, specifically by 70% or more and more specifically by 80% or more and if one of the antibodies described in Tables 1-4 reduces the binding of said antibody or antibody fragment to GPVI by 60% or more, specifically by 70% or more and more specifically by 80% or more.

The term "epitope" includes any proteinaceous region which is specifically recognized by an antibody or fragment thereof or a T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

"Binds the same epitope as" means the ability of an antibody or antibody fragment to bind to a specific antigen and binding to the same epitope as the exemplified antibody when using the same epitope mapping technique for comparing the antibodies. The epitopes of the exemplified antibody and other antibodies can be determined using epitope mapping techniques. Epitope mapping techniques are well known in the art. For example, conformational epitopes are readily identified by determining spatial conformation of amino acids such as by, e.g., hydrogen/deuterium exchange, x-ray crystallography and two-dimensional nuclear magnetic resonance.

The terms "engineered" or "modified" as used herein includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies or antibody fragments of the disclosure are engineered or modified, including for example, humanized and/or chimeric antibodies, and antibodies which have been engineered to improve one or more properties, such as antigen binding, stability/half-life, effector function, immunogenicity, safety and the like.

A "wildtype" protein or portion thereof is a version of the protein as it is found in nature. An amino acid sequence of a wildtype protein, e.g., a heavy chain constant region, is the amino acid sequence of the protein as it occurs in nature. Due to allotypic differences, there can be more than one amino acid sequence for a wildtype protein. For example, there are several allotypes of naturally occurring human IGg1 heavy chain constant regions (see, e.g., Jeffries et al. (2009) mAbs 1:1).

"Allotype" refers to naturally occurring variants within a specific isotype group, which variants differ in a few amino acids (see, e.g., Jefferies et al. (2009) mAbs 1:1). Antibodies described herein may be of any allotype.

As used herein, the term "pre-existing" antibodies is meant to refer to antibodies that are normally present in a subject or organism.

Embodiments

Sequences

In an embodiment, the present disclosure refers to an antibody or antibody fragment specific for Glycoprotein VI (GPVI). In an embodiment, the present disclosure refers to an isolated antibody or antibody fragment specific for Glycoprotein VI (GPVI). In an embodiment, the present disclosure refers to an isolated monoclonal antibody or antibody fragment specific for GPVI. In an embodiment, the present disclosure refers to an isolated monoclonal antibody or antibody fragment specific for GPVI comprising the variable heavy chain (VH) and the variable light chain (VL) of any one of the antibodies disclosed in Tables 1-4. In an embodiment, the present disclosure refers to an isolated monoclonal antibody or antibody fragment specific for GPVI comprising the heavy chain (HC) and the light chain (LC) of any one of the antibodies disclosed in Tables 1-4.

In an embodiment, the present disclosure refers to an isolated monoclonal antibody or antibody fragment specific for GPVI comprising 6 CDRs defined by Kabat of any one of the antibodies disclosed in Tables 1-4. In an embodiment, the present disclosure refers to an isolated monoclonal antibody or antibody fragment specific for GPVI comprising 6 CDRs of any one of the antibodies disclosed in Tables 1-4.

In an embodiment, the present disclosure refers to an antibody or antibody fragment specific for GPVI, wherein said antibody or antibody fragment comprises
- a) the variable heavy chain CDR1 (HCDR1) region comprising the amino acid sequence of SEQ ID NO: 11, the variable heavy chain CDR2 (HCDR2) region comprising the amino acid sequence of SEQ ID NO: 12, the variable heavy chain CDR3 (HCDR3) region comprising the amino acid sequence of SEQ ID NO: 13, the variable light chain CDR1 (LCDR1) region comprising the amino acid sequence of SEQ ID NO: 14, the variable light chain CDR2 (LCDR2) region comprising the amino acid sequence of SEQ ID NO: 15 and the variable light chain CDR3 (LCDR3) region comprising the amino acid sequence of SEQ ID NO: 16, or
- b) the HCDR1 region comprising the amino acid sequence of SEQ ID NO: 22, the HCDR2 region comprising the amino acid sequence of SEQ ID NO: 23, the HCDR3 region comprising the amino acid sequence of SEQ ID NO: 24, the LCDR1 region comprising the amino acid sequence of SEQ ID NO: 25, the LCDR2 region comprising the amino acid sequence of SEQ ID NO: 26 and the LCDR3 region comprising the amino acid sequence of SEQ ID NO: 27, or
- c) the HCDR1 region comprising the amino acid sequence of SEQ ID NO: 33, the HCDR2 region comprising the amino acid sequence of SEQ ID NO: 34, the HCDR3 region comprising the amino acid sequence of SEQ ID NO: 35, the LCDR1 region comprising the amino acid sequence of SEQ ID NO: 36, the LCDR2 region comprising the amino acid sequence of SEQ ID NO: 37 and the LCDR3 region comprising the amino acid sequence of SEQ ID NO: 38, or
- d) the HCDR1 region comprising the amino acid sequence of SEQ ID NO: 44, the HCDR2 region comprising the amino acid sequence of SEQ ID NO: 45, the HCDR3 region comprising the amino acid sequence of SEQ ID NO: 46, the LCDR1 region comprising the amino acid sequence of SEQ ID NO: 47, the LCDR2 region comprising the amino acid sequence of SEQ ID NO: 48 and the LCDR3 region comprising the amino acid sequence of SEQ ID NO: 49.

In an embodiment, said antibody or antibody fragment is an isolated antibody or antibody fragment. In an embodiment, said antibody or antibody fragment is a monoclonal antibody or antibody fragment. In an embodiment, said antibody or antibody fragment is an isolated monoclonal antibody or antibody fragment. In an embodiment, said antibody or antibody fragment is an isolated monoclonal human antibody or antibody fragment. In one embodiment, said antibody fragment is selected from the group consisting of a Fab, a Fab', a Fv, a scFv. In one embodiment, said antibody fragment is a Fab.

In an embodiment, the present disclosure refers to an antibody or antibody fragment specific for GPVI, wherein said antibody or antibody fragment comprises
- a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
- b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO: 27, or
- c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
- d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region comprising the amino acid sequence of SEQ ID NO: 49.

In an embodiment, said antibody or antibody fragment is an isolated antibody or antibody fragment. In an embodiment, said antibody or antibody fragment is a monoclonal antibody or antibody fragment. In an embodiment, said antibody or antibody fragment is an isolated monoclonal antibody or antibody fragment. In an embodiment, said antibody or antibody fragment is an isolated monoclonal human antibody or antibody fragment. In one embodiment, said antibody fragment is selected from the group consisting of a Fab, a Fab', a Fv, a scFv. In one embodiment, said antibody fragment is a Fab.

In an embodiment, the present disclosure refers to an antibody or antibody fragment specific for GPVI, wherein said antibody or antibody fragment comprises
- a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, and further comprises the VH of SEQ ID NO: 17 and the VL of SEQ ID NO: 16, or
- b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO: 27, and further comprises the VH of SEQ ID NO: 28 and the VL of SEQ ID NO: 29, or
- c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, and further comprises the VH of SEQ ID NO: 39 and the VL of SEQ ID NO: 40, or
- d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region comprising the amino acid sequence of SEQ ID NO: 49, and further comprises the VH of SEQ ID NO: 50 and the VL of SEQ ID NO: 51.

In an embodiment, said antibody or antibody fragment is an isolated antibody or antibody fragment. In an embodiment, said antibody or antibody fragment is a monoclonal antibody or antibody fragment. In an embodiment, said antibody or antibody fragment is an isolated monoclonal antibody or antibody fragment. In an embodiment, said antibody or antibody fragment is an isolated monoclonal human antibody or antibody fragment. In one embodiment, said antibody fragment is selected from the group consisting of a Fab, a Fab', a Fv, a scFv. In one embodiment, said antibody fragment is a Fab.

In an embodiment, the present disclosure refers to an antibody or antibody fragment specific for GPVI, wherein said antibody or antibody fragment comprises the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16.

In an embodiment, the present disclosure refers to an antibody or antibody fragment specific for GPVI, wherein said antibody or antibody fragment comprises the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO: 27.

In an embodiment, the present disclosure refers to an antibody or antibody fragment specific for GPVI, wherein said antibody or antibody fragment comprises the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38.

In an embodiment, the present disclosure refers to an antibody or antibody fragment specific for GPVI, wherein said antibody or antibody fragment comprises the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region of SEQ ID NO: 49.

In an embodiment, the present disclosure refers to an antibody or antibody fragment specific for GPVI, wherein said antibody or antibody fragment comprises
  a) the VH of SEQ ID NO: 17 and the VL of SEQ ID NO: 18 or
  b) the VH of SEQ ID NO: 28 and the VL of SEQ ID NO: 29 or
  c) the VH of SEQ ID NO: 39 and the VL of SEQ ID NO: 40 or
  d) the VH of SEQ ID NO: 50 and the VL of SEQ ID NO: 51 or
  a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In an embodiment, the present disclosure refers to an antibody or antibody fragment specific for GPVI, wherein said antibody or antibody fragment comprises
  a) the VH of SEQ ID NO: 17 and the VL of SEQ ID NO: 18 or
  b) the VH of SEQ ID NO: 28 and the VL of SEQ ID NO: 29 or
  c) the VH of SEQ ID NO: 39 and the VL of SEQ ID NO: 40 or
  d) the VH of SEQ ID NO: 50 and the VL of SEQ ID NO: 51.

In one embodiment, the present disclosure refers to an antibody or antibody fragment specific for GPVI, wherein said antibody or antibody fragment comprises the VH of SEQ ID NO: 17 and the VL of SEQ ID NO: 18 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the VH of SEQ ID NO: 17 and the VL of SEQ ID NO: 18.

In one embodiment, the present disclosure refers to an antibody or antibody fragment specific for GPVI, wherein said antibody or antibody fragment comprises the VH of SEQ ID NO: 28 and the VL of SEQ ID NO: 29 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the VH of SEQ ID NO: 28 and the VL of SEQ ID NO: 29.

In one embodiment, the present disclosure refers to an antibody or antibody fragment specific for GPVI, wherein said antibody or antibody fragment comprises the VH of SEQ ID NO: 39 and the VL of SEQ ID NO: 40 or a sequence having least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the VH of SEQ ID NO: 39 and the VL of SEQ ID NO: 40.

In one embodiment, the present disclosure refers to an antibody or antibody fragment specific for GPVI, wherein said antibody or antibody fragment comprises the VH of SEQ ID NO: 50 and the VL of SEQ ID NO: 51 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the VH of SEQ ID NO: 50 and the VL of SEQ ID NO: 51.

In one embodiment, the present disclosure refers to an antibody or antibody fragment specific for GPVI, wherein said antibody or antibody fragment comprises the HC of SEQ ID NO: 20 and the LC of SEQ ID NO: 19 or a sequence having at least 60%, at least 70%, at least 80%, at least 90%, or at least 95% identity with these sequences but which retains the same activity as the said antibody or antibody fragment.

In one embodiment, the present disclosure refers to an antibody or antibody fragment specific for GPVI, wherein said antibody or antibody fragment comprises the HC of SEQ ID NO: 20 and the LC of SEQ ID NO: 19. In one embodiment, the present disclosure refers to an antibody or antibody fragment specific for GPVI, wherein said antibody or antibody fragment consists of the HC of SEQ ID NO: 20 and the LC of SEQ ID NO: 19. In one embodiment, the present disclosure refers to an antibody or antibody fragment specific for GPVI, wherein said antibody or antibody fragment comprises the HC of SEQ ID NO: 21 and the LC of SEQ ID NO: 19 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the HC of SEQ ID NO: 21 and the LC of SEQ ID NO: 19. In one embodiment, the present disclosure refers to an antibody or antibody fragment specific for GPVI, wherein said antibody or antibody fragment consists of the HC of SEQ ID NO: 21 and the LC of SEQ ID NO: 19.

In one embodiment, the present disclosure refers to an antibody or antibody fragment specific for GPVI, wherein said antibody or antibody fragment comprises the HC of SEQ ID NO: 31 and the LC of SEQ ID NO: 30 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the HC of SEQ ID NO: 31 and the LC of SEQ ID NO: 30. In one embodiment, the present disclosure refers to an antibody or antibody fragment specific for GPVI, wherein said antibody or antibody fragment consists the HC of SEQ ID NO: 31 and the LC of SEQ ID NO: 30. In one embodiment, the present disclosure refers to an antibody or antibody fragment specific for GPVI, wherein said antibody or antibody fragment comprises the HC of SEQ ID NO: 32 and the LC of SEQ ID NO: 30 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the HC of SEQ ID NO: 32 and the LC of SEQ ID NO: 30. In one embodiment, the present disclosure refers to an antibody or antibody fragment specific for GPVI, wherein said antibody or antibody fragment consists of the HC of SEQ ID NO: 32 and the LC of SEQ ID NO: 30.

In one embodiment, the present disclosure refers to an antibody or antibody fragment specific for GPVI, wherein said antibody or antibody fragment comprises the HC of SEQ ID NO: 42 and the light chain LC of SEQ ID NO: 41 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the HC of SEQ ID NO: 42 and the light chain LC of SEQ ID NO: 41. In one embodiment, the present disclosure refers to an antibody or antibody fragment specific for GPVI, wherein said antibody or antibody fragment consists of the HC of SEQ ID NO: 42 and the light chain LC of SEQ ID NO: 41. In one embodiment, the present disclosure refers to an antibody or antibody fragment specific for GPVI, wherein said antibody or antibody fragment comprises the HC of SEQ ID NO: 43 and the LC of SEQ ID NO: 41 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the HC of SEQ ID NO: 43 and the LC of SEQ ID NO: 41. In one embodiment, the present disclosure refers to an antibody or antibody fragment specific for GPVI, wherein said antibody or antibody fragment consists of the HC of SEQ ID NO: 43 and the LC of SEQ ID NO: 41

In one embodiment, the present disclosure refers to an antibody or antibody fragment specific for GPVI, wherein said antibody or antibody fragment comprises the HC of SEQ ID NO: 53 and the LC of SEQ ID NO: 52 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the HC of SEQ ID NO: 53 and the LC of SEQ ID NO: 52. In one embodiment, the present disclosure refers to an antibody or antibody fragment specific for GPVI, wherein said antibody or antibody fragment consists of the HC of SEQ ID NO: 53 and the LC of SEQ ID NO: 52. In one embodiment, the present disclosure refers to an antibody or antibody fragment specific for GPVI, wherein said antibody or antibody fragment comprises the HC of SEQ ID NO: 54 and the LC of SEQ ID NO: 52 or a sequence having at least 60%, at least 70%, at least 80%, at least 90%, or at least 95% identity with these sequences but which retains the same activity as the said antibody or antibody fragment. In one embodiment, the present disclosure refers to an antibody or antibody fragment specific for GPVI, wherein said antibody or antibody fragment comprises the HC of SEQ ID NO: 54 and the LC of SEQ ID NO: 52. In one embodiment, the present disclosure refers to an antibody or antibody fragment specific for GPVI, wherein said antibody or antibody fragment consists the HC of SEQ ID NO: 54 and the LC of SEQ ID NO: 52.

In a further embodiment, said antibody or antibody fragment comprises
a) the HC of SEQ ID NO: 20 and the LC of SEQ ID NO: 19 or
b) the HC of SEQ ID NO: 21 and the LC of SEQ ID NO: 19 or
c) the HC of SEQ ID NO: 31 and the LC of SEQ ID NO: 30 or
d) the HC of SEQ ID NO: 32 and the LC of SEQ ID NO: 30 or
e) the HC of SEQ ID NO: 42 and the LC of SEQ ID NO: 41 or
f) the HC of SEQ ID NO: 43 and the LC of SEQ ID NO: 41 or
g) the HC of SEQ ID NO: 53 and the LC of SEQ ID NO: 52 or
h) the HC of SEQ ID NO: 54 and the LC of SEQ ID NO: 52.

In an embodiment, said aforementioned antibody or antibody fragment specific for GPVI are isolated antibody or antibody fragments. In an embodiment, said antibodies or antibody fragments are monoclonal antibodies or antibody fragments. In an embodiment, said antibodies or antibody fragments are isolated monoclonal antibodies or antibody fragments. In an embodiment, said antibodies or antibody fragments are isolated monoclonal human antibodies or antibody fragments. In one embodiment, said antibody fragments are selected from the group consisting of a Fab, a Fab', a Fv, a scFv. In one embodiment, said antibody fragments are a Fab.

In an embodiment, the antibody or antibody fragment specific for GPVI according to the present disclosure comprises a human heavy chain constant region and a human light chain constant region.

Formats

In certain embodiments, the antibody or antibody fragment of the present disclosure is a monoclonal antibody or antibody fragment.

In one embodiment of the present disclosure, the antibody or antibody fragment specific for GPVI according to the present disclosure is a human, humanized, chimeric or synthetic antibody or antibody fragment. In one embodiment, said antibody or an antibody fragment is a human or humanized antibody or antibody fragment. In one embodiment, said antibody or an antibody fragment is a human antibody or antibody fragment. In another embodiment, said antibody or antibody fragment is a chimeric antibody or antibody fragment.

In an embodiment, the antibody or antibody fragment specific for GPVI according to the present disclosure is a recombinant antibody or antibody fragment. In an embodiment, the antibody or antibody fragment specific for GPVI according to the present disclosure is an isolated antibody or antibody fragment. In a further embodiment, the antibody or antibody fragment specific for GPVI according to the present disclosure is an isolated recombinant antibody or antibody fragment. In a further embodiment, said isolated recombinant human antibody or antibody fragment is an isolated recombinant human antibody or antibody fragment.

In an embodiment, the antibody or antibody fragment specific for GPVI according to the present disclosure is a monoclonal antibody or antibody fragment. In one embodiment, the antibody or antibody fragment of the present disclosure is an isolated monoclonal antibody or antibody fragment. In one embodiment, the antibody or antibody fragment of the present disclosure is an isolated monoclonal antibody or antibody fragment.

In an embodiment, said antibody or antibody fragment specific for GPVI is an IgG. In another embodiment, said antibody or antibody fragment is of the IgG1 isotype.

In one embodiment, the antibody or antibody fragment specific for GPVI of the present disclosure is a monovalent antibody or antibody fragment. In one embodiment, said monovalent antibody or antibody fragment is selected from the group consisting of a full-length antibody, a scFv, a Fv, a Fab and a Fab'. In a preferred embodiment, said monovalent antibody fragment is a Fab.

Nucleic acids—Vectors—Cell

In an embodiment, the present disclosure refers to a nucleic acid composition comprising a nucleic acid sequence or a plurality of nucleic acid sequences encoding an antibody or antibody fragment specific for GPVI, wherein said antibody or antibody fragment comprises
  a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
  b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or
  c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
  d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region of SEQ ID NO: 49.

In another embodiment, the present disclosure refers to an isolated nucleic acid or a plurality of nucleic acid sequences encoding a heavy chain sequence and/or light chain sequence of an antibody or antibody fragment specific for GPVI, the nucleic acid comprising
  a) the HCDR1 region of SEQ ID NO: 55, the HCDR2 region of SEQ ID NO: 56, the HCDR3 region of SEQ ID NO: 57, the LCDR1 region of SEQ ID NO: 58, the LCDR2 region of SEQ ID NO: 59 and the LCDR3 region of SEQ ID NO: 60, or
  b) the HCDR1 region of SEQ ID NO: 66, the HCDR2 region of SEQ ID NO: 67, the HCDR3 region of SEQ ID NO: 68, the LCDR1 region of SEQ ID NO: 69, the LCDR2 region of SEQ ID NO: 70 and the LCDR3 region of SEQ ID NO: 71, or
  c) the HCDR1 region of SEQ ID NO: 77, the HCDR2 region of SEQ ID NO: 78, the HCDR3 region of SEQ ID NO: 79, the LCDR1 region of SEQ ID NO: 80, the LCDR2 region of SEQ ID NO: 81 and the LCDR3 region of SEQ ID NO: 82, or
  d) the HCDR1 region of SEQ ID NO: 88, the HCDR2 region of SEQ ID NO: 89, the HCDR3 region of SEQ ID NO: 90, the LCDR1 region of SEQ ID NO.: 91, the LCDR2 region of SEQ ID NO: 92 and the LCDR3 region of SEQ ID NO: 93.

In another embodiment, the present disclosure refers to an isolated nucleic acid or a plurality of nucleic acid sequences encoding a heavy chain sequence and/or light chain sequence of an antibody or antibody fragment specific for GPVI, the nucleic acid comprising
  a) the HCDR1 region comprising the nucleic acid sequence of SEQ ID NO: 55, the HCDR2 region comprising the nucleic acid sequence of SEQ ID NO: 56, the HCDR3 region comprising the nucleic acid sequence of SEQ ID NO: 57, the LCDR1 region comprising the nucleic acid sequence of SEQ ID NO: 58, the LCDR2 region comprising the nucleic acid sequence of SEQ ID NO: 59 and the LCDR3 region comprising the nucleic acid sequence of SEQ ID NO: 60, or
  b) the HCDR1 region comprising the nucleic acid sequence of SEQ ID NO: 66, the HCDR2 region comprising the nucleic acid sequence of SEQ ID NO: 67, the HCDR3 region comprising the nucleic acid sequence of SEQ ID NO: 68, the LCDR1 region comprising the nucleic acid sequence of SEQ ID NO: 69, the LCDR2 region comprising the nucleic acid sequence of SEQ ID NO: 70 and the LCDR3 region comprising the nucleic acid sequence of SEQ ID NO: 71, or
  c) the HCDR1 region comprising the nucleic acid sequence of SEQ ID NO: 77, the HCDR2 region comprising the nucleic acid sequence of SEQ ID NO: 78, the HCDR3 region comprising the nucleic acid sequence of SEQ ID NO: 79, the LCDR1 region comprising the nucleic acid sequence of SEQ ID NO: 80, the LCDR2 region comprising the nucleic acid sequence of SEQ ID NO: 81 and the LCDR3 region comprising the nucleic acid sequence of SEQ ID NO: 82, or
  d) the HCDR1 region comprising the nucleic acid sequence of SEQ ID NO: 88, the HCDR2 region comprising the nucleic acid sequence of SEQ ID NO: 89, the HCDR3 region comprising the nucleic acid sequence of SEQ ID NO: 90, the LCDR1 region comprising the nucleic acid sequence of SEQ ID NO.: 91, the LCDR2 region comprising the nucleic acid sequence of SEQ ID NO: 92 and the LCDR3 region comprising the nucleic acid sequence of SEQ ID NO: 93.

In another embodiment, the present disclosure refers to a nucleic acid sequence or a plurality of nucleic acid sequences encoding an isolated monoclonal antibody or antibody fragment specific for GPVI, wherein the nucleic acid sequence or plurality of nucleic acid sequences comprises the VH of SEQ ID NO: 61 and/or the VL of SEQ ID NO: 62, or the VH and/or the VL that has at least 60%, at least 70%, at least 80%, at least 90% or at least 95% identity to the VH of SEQ ID NO: 61 and the VL of SEQ ID NO: 62.

In another embodiment, the present disclosure refers to a nucleic acid sequence or a plurality of nucleic acid sequences encoding an isolated monoclonal antibody or antibody fragment specific for GPVI, wherein the nucleic acid sequence or the plurality of nucleic acid sequences comprises the VH of SEQ ID NO: 72 and/or the VL of SEQ ID NO: 73, or the VH and/or the VL that has at least 60%, at least 70%, at least 80%, at least 90% or at least 95% identity to the VH of SEQ ID NO: 72 and the VL of SEQ ID NO: 73.

In another embodiment, the present disclosure refers to a nucleic acid sequence or a plurality of nucleic acid sequences encoding an isolated monoclonal antibody or antibody fragment specific for GPVI, wherein the nucleic acid sequence or the plurality of nucleic acid sequences comprises the VH of SEQ ID NO: 83 and/or the VL of SEQ ID NO: 84, or the VH and/or the VL that has at least 60%, at least 70%, at least 80%, at least 90% or at least 95% identity to the VH region of SEQ ID NO: 83 and the VL of SEQ ID NO: 84.

In another embodiment, the present disclosure refers to a nucleic acid sequence or a plurality of nucleic acid sequences encoding an isolated monoclonal antibody or antibody fragment specific for GPVI, wherein the nucleic acid sequence or the plurality of nucleic acid sequences comprises the VH of SEQ ID NO: 94 and/or the VL of SEQ ID NO: 95, or the VH and/or the VL that has at least 60%, at least 70%, at least 80%, at least 90% or at least 95% identity to the VH region of SEQ ID NO: 94 and the VL of SEQ ID NO: 95.

In another embodiment, the present disclosure refers to a nucleic acid sequence or a plurality of nucleic acid sequences encoding an isolated monoclonal antibody or antibody fragment specific for GPVI, wherein the nucleic acid sequence or the plurality of nucleic acid sequences comprises the HC of SEQ ID NO: 64 and/or the LC of SEQ ID NO: 63. In another embodiment, the present disclosure refers to a nucleic acid sequence or a plurality of nucleic acid sequences encoding an isolated monoclonal antibody or antibody fragment specific for GPVI, wherein the nucleic acid or the plurality of nucleic acid sequences comprises the HC of SEQ ID NO: 65 and/or the LC of SEQ ID NO: 63.

In another embodiment, the present disclosure refers to a nucleic acid sequence or a plurality of nucleic acid sequences encoding an isolated monoclonal antibody or antibody fragment specific for GPVI, wherein the nucleic acid sequence or the plurality of nucleic acid sequences comprises the HC of SEQ ID NO: 75 and/or the LC of SEQ ID NO: 74. In another embodiment, the disclosure refers to a nucleic acid sequence or a plurality of nucleic acid sequences encoding an isolated monoclonal antibody or antibody fragment specific for GPVI, wherein the nucleic acid sequence or the plurality of nucleic acid sequences comprises the HC of SEQ ID NO: 76 and/or the LC of SEQ ID NO: 74.

In another embodiment, the disclosure refers to a nucleic acid sequence or a plurality of nucleic acid sequences encoding an isolated monoclonal antibody or antibody fragment specific for GPVI, wherein the nucleic acid sequence or the plurality of nucleic acid sequences comprises the HC of SEQ ID NO: 86 and/or the LC of SEQ ID NO: 85. In another embodiment, the disclosure refers to a nucleic acid sequence or a plurality of nucleic acid sequences encoding an isolated monoclonal antibody or antibody fragment specific for GPVI, wherein the nucleic acid sequence or a plurality of nucleic acid sequences comprises the HC of SEQ ID NO: 87 and/or the LC of SEQ ID NO: 85.

In another embodiment, the disclosure refers to a nucleic acid sequence or a plurality of nucleic acid sequences encoding an isolated monoclonal antibody or antibody fragment specific for GPVI, wherein the nucleic acid sequence or the plurality of nucleic acid sequences comprises the HC of SEQ ID NO: 97 and/or the LC of SEQ ID NO: 96. In another embodiment, the disclosure refers to a nucleic acid sequence or a plurality of nucleic acid sequences encoding an isolated monoclonal antibody or antibody fragment specific for GPVI, wherein the nucleic acid sequence or a plurality of nucleic acid sequences comprises the HC of SEQ ID NO: 98 and/or the LC of SEQ ID NO: 96.

In another embodiment, the present disclosure refers to a nucleic acid sequence or a plurality of nucleic acid sequences encoding an isolated monoclonal antibody or fragment, wherein the nucleic acid sequence or a plurality of nucleic acid sequences comprises the VH and/or the VL of any one of the antibodies disclosed in Tables 1-4.

In another embodiment, the present disclosure provides an antibody or antibody fragment specific for GPVI, encoded by any one of the nucleic acid sequences or of the plurality of nucleic acid sequences disclosed in Tables 1-4.

In certain embodiments, the present disclosure provides a nucleic acid sequence or a plurality of nucleic acid sequences encoding any one of the antibodies or antibody fragments disclosed in Tables 1-4.

In another embodiment, the present disclosure provides a nucleic acid sequence or a plurality of nucleic acid sequences encoding an antibody or antibody fragment according to the present disclosure which specifically binds to GPVI.

In another embodiment, the present disclosure refers to a nucleic acid sequence or a plurality of nucleic acid sequences encoding an isolated monoclonal antibody or antibody fragment wherein the nucleic acid sequence or the plurality of nucleic acid sequences comprises a HC and/or a LC of any one of the antibodies or antibody fragments disclosed in Tables 1-4.

Vectors

In an embodiment, the present disclosure refers to a vector composition comprising a vector or a plurality of vectors comprising a nucleic acid sequence or plurality of nucleic acid sequences encoding an antibody or antibody fragment specific for GPVI according to the present disclosure.

In an embodiment, the present disclosure refers to a vector composition comprising a vector or a plurality of vectors comprising a nucleic acid sequence or plurality of nucleic acid sequences encoding an antibody or antibody fragment specific for GPVI disclosed in Tables 1-4.

In an embodiment, the present disclosure refers to a vector composition comprising a vector or a plurality of vectors comprising a nucleic acid sequence or plurality of nucleic acid sequences disclosed in Tables 1-4.

In an embodiment, the present disclosure provides a vector comprising a nucleic acid encoding an antibody or antibody fragment specific for GPVI, according to the present disclosure.

In an embodiment, the present disclosure provides a vector comprising a nucleic acid disclosed in Tables 1-4.

In an embodiment, the present disclosure provides a vector comprising a nucleic acid encoding an antibody or antibody fragment disclosed in Tables 1-4.

Host Cell

In an embodiment, the present disclosure refers to a host cell comprising a vector composition comprising a vector or a plurality of vectors comprising the nucleic acid sequence or plurality of nucleic acid sequences encoding an antibody or antibody fragment specific for GPVI according to the present disclosure.

In an embodiment, the present disclosure refers to a host cell comprising a vector composition comprising a vector or a plurality of vectors comprising the nucleic acid sequence or plurality of nucleic acid sequences encoding an antibody or antibody fragment specific for GPVI disclosed in Tables 1-4.

In an embodiment, the present disclosure provides a host cell comprising a vector comprising a nucleic acid encoding an antibody or antibody fragment specific for GPVI according to the present disclosure.

In an embodiment, the present disclosure provides a host cell comprising a nucleic acid encoding an antibody or antibody fragment specific for GPVI of the present disclosure.

In another embodiment, the present disclosure provides an isolated host cell comprising a vector comprising a nucleic acid disclosed in Tables 1-4.

In an embodiment, said host cell is able to express the polypeptide encoded by the vector. In a further embodiment, said host cell is an isolated cell. In a further embodiment, said isolated host cell is a mammalian cell. In an embodiment, said mammalian cell is a human cell. In another embodiment, said mammalian cell is a CHO cell.

In certain embodiments of the present disclosure, additional amino acid residues, polypeptides or moieties are added to the antibody or antibody fragment of the present disclosure, for example to aid in the expression or purification or to increase the stability of the Fab of the present disclosure.

The coding sequences for the heavy and light chain of the antibody or antibody fragment of the present disclosure can be recombinant DNA molecules, which are introduced into expression vectors by operatively linking the DNA to the necessary expression control regions (e.g. regulatory regions) required for gene expression The skilled man will realize that the polynucleotides encoding the heavy or light chain can be cloned into different vectors or in the same vector. In a preferred embodiment, said polynucleotides are cloned in the same vector. The vectors can be introduced into the appropriate host cells such as prokaryotic (e.g., bacterial) or eukaryotic (e.g., yeast or mammalian) cells by methods well known in the art (see e.g., "Current Protocol in Molecular Biology", Ausubel et al. (eds.), Greene Publishing Assoc. and John Wiley Interscience, New York, 1989 and 1992). Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. Upon expression in host cells, the antibodies or antibody fragments of the present disclosure are obtained. These steps can be achieved in different ways, as will be known by the person skilled in the art. In general, such steps typically include transforming or transfecting a suitable host cell with a nucleic acid or vector or an infectious particle which encodes the antibody or antibody fragments. Further, such steps typically include culturing said host cells under conditions suitable for the proliferation (multiplication, growth) of said host cells and a culturing step under conditions suitable for the production (expression, synthesis) of the encoded antibody or antibody fragment. The culturing of host cells under conditions suitable for proliferation or expression is typically accomplished in the presence of media comprising components suitable for cell growth or induction of expression. In particular embodiments, the methods for the production of antibody or antibody fragment of the present disclosure further comprise the step of isolating the produced antibody or antibody fragment from the host cells or medium. Depending on the expression system and host selected, the antibody or antibody fragment of the present disclosure is produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art. The antibody or antibody fragment of the present disclosure can then be purified by a number of techniques as known to the person skilled in the art.

Binding

In an embodiment, the present disclosure refers to an isolated antibody or antibody fragment specific for human GPVI.

In one embodiments, the present disclosure refers to an isolated antibody or antibody fragment specific for the isoforms and haplotypes of human GPVI comprising the amino acid sequence SEQ ID NO: 1, SEQ ID NO: 4, SEQ ID NO: 5 and/or SEQ ID NO: 6. In one embodiment, the antibody or antibody fragment according to the present disclosure is specific for human GPVI encoded by the amino acid sequence of SEQ ID NO: 1. In one embodiment, the antibody or antibody fragment according to the present disclosure is specific for the extracellular domain of human GPVI encoded by the amino acid sequence of SEQ ID NO: 4, SEQ ID NO: 5 and/or SEQ ID NO: 6. In one embodiment, the antibody or antibody fragment of the present disclosure is specific for a polypeptide comprising the amino acid sequence of SEQ ID NO: 1. In one embodiment, the present disclosure relates to an antibody or antibody fragment specific for a polypeptide encoded by SEQ ID NO: I. In an embodiment, said antibody or antibody fragment being specific for a polypeptide comprising the amino acid sequence of SEQ ID NO: 1, SEQ ID NO: 4, SEQ ID NO: 5 and/or SEQ ID NO: 6 is a monoclonal antibody. In a further embodiment, said antibody or antibody fragment is an isolated antibody or antibody fragment.

In one embodiment, the antibody or antibody fragment of the present disclosure binds to the extracellular domain of GPVI. In one embodiment, the antibody or antibody fragment of the present disclosure binds to the D1 domain of the extracellular domain of human GPVI. In another embodiment, the antibody or antibody fragment of the present disclosure binds to the D2 domain of the extracellular domain of human GPVI.

The antibody or antibody fragment of the present disclosure is cross-reactive to cynomolgus monkey and rodent GPVI, such as mouse or rat GPVI. In an embodiment, the antibody or antibody fragment specific for GPVI according to the present disclosure is cross-reactive with GPVI of another species, such as GPVI from mouse, rat and/or cynomolgus monkey. In an embodiment, the antibody or antibody fragment according to the present disclosure is specific for human GPVI, cynomolgus monkey GPVI, mouse GPIV and rat GPVI. In one embodiments, the antibody or antibody fragment according to the present disclosure is specific for cynomolgus monkey GPVI. In one embodiment, the antibody or antibody fragment according to the present disclosure is specific for mouse GPVI. In one embodiments, the antibody or antibody fragment according to the present is specific for rat GPVI.

In one embodiments, the antibody or antibody fragment according to the present disclosure is specific for human GPVI and mouse GPVI. In one embodiments, the antibody or antibody fragment according to the present disclosure is specific for human GPVI, cynomolgus monkey GPVI, and mouse GPVI. In one embodiment, the disclosure refers to an isolated antibody or antibody fragment specific for GPVI, wherein said antibody or antibody fragment binds to human GPVI and to cynomolgus monkey GPVI. In one embodiment, the disclosure refers to an isolated antibody or antibody fragment specific, for GPVI, wherein said antibody or antibody fragment binds to human GPVI and to rodent GPVI. In an embodiment, said rodent GPVI is mouse and rat GPVI.

In one embodiment, the present disclosure refers to an isolated antibody or antibody fragment specific for GPVI, wherein said antibody or antibody fragment binds to human GPVI, to cynomolgus monkey GPVI, to mouse GPIV and to rat GPVI.

In another embodiment, the present disclosure provides an antibody or antibody fragment specific for human GPVI, cynomolgus monkey GPVI, mouse GPIV and rat GPVI, wherein said antibody or antibody fragment comprises
  a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
  b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or
  c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
  d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region comprising the amino acid sequence of SEQ ID NO: 49.

In a further embodiment, said antibody or antibody fragment comprises
  a) the VH of SEQ ID NO: 17 and the VL of SEQ ID NO: 18 or
  b) the VI-1 of SEQ ID NO: 28 and the VL of SEQ ID NO: 29 or
  c) the VH of SEQ ID NO: 39 and the VL of SEQ ID NO: 40 or
  d) the VH of SEQ ID NO: 50 and the VL of SEQ ID NO: 51 or
    a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In a further embodiment, said antibody or antibody fragment comprises
  a) the HC of SEQ ID NO: 20 and the LC of SEQ ID NO: 19 or
  b) the HC of SEQ ID NO: 21 and the LC of SEQ ID NO: 19 or
  c) the HC of SEQ ID NO: 31 and the LC of SEQ ID NO: 30 or
  d) the HC of SEQ ID NO: 32 and the LC of SEQ ID NO: 30 or
  e) the HC of SEQ ID NO: 42 and the LC of SEQ ID NO: 41 or
  f) the HC of SEQ ID NO: 43 and the LC of SEQ ID NO: 41 or
  g) the HC of SEQ ID NO: 53 and the LC of SEQ ID NO: 52 or
  h) the HC of SEQ ID NO: 54 and the LC of SEQ ID NO: 52.

In an embodiment, said antibody or antibody fragment is a monoclonal antibody or antibody fragment. In an embodiment, said antibody or antibody fragment is an isolated antibody or antibody fragment. In an embodiment, said antibody or antibody fragment is an isolated monoclonal antibody or antibody fragment. In an embodiment, said antibody or antibody fragment is a monovalent antibody or antibody fragment. In one embodiment, said monovalent antibody or antibody fragment is selected from the group consisting of a scFv, an Fv, a Fab and a Fab'. In a preferred embodiment, said monovalent antibody or antibody fragment is a Fab.

Affinity

In an embodiment, the present disclosure refers to an isolated antibody or antibody fragment specific for GPVI, wherein said antibody or antibody fragment has a monovalent affinity to GPVI with a dissociation rate constant ($K_D$) of less than $5\times10^{-2}$M, less than $1\times10^{-2}$M, less than $5\times10^{-3}$M, less than $1\times10^{-3}$M, less than $5\times10^{-4}$M, less than $1\times10^{-4}$M, less than $5\times10^{-5}$M, less than $1\times10^{-5}$M, less than $5\times10^{-6}$M, less than $1\times10^{-6}$M, less than $5\times10^{-7}$M, less than $1\times10^{-7}$M, less than $5\times10^{-8}$M, less than $1\times10^{-8}$M, less than $5\times10^{-9}$M, less than $1\times10^{-9}$M, less than $5\times10^{-10}$M, less than $1\times10^{-10}$M, less than $5\times10^{-11}$M, less than $1\times10^{-11}$M, less than $5\times10^{-12}$M, less than $1\times10^{-12}$M, less than $5\times10^{-13}$M, less than $1\times10^{-13}$M, less than $5\times10^{-14}$M, less than $1\times10^{-14}$M, less than $5\times10^{-15}$M, or less than $1\times10^{-15}$M.

In certain embodiments, the present disclosure provides an isolated antibody or antibody fragment specific for GPVI, wherein said antibody or antibody fragment has a monovalent affinity to GPVI with a dissociation rate constant (Kr) of less than $1\times10^{-7}$M, $1\times10^{-8}$M, $1\times10^{-9}$M, $1\times10^{-10}$M, $1\times10^{-11}$M, $1\times10^{-12}$M or $1\times10^{-13}$M.

In certain embodiments, the present disclosure refers to an antibody or antibody fragment specific for GPVI disclosed in Tables 1-4, wherein said antibody or antibody fragment binds to GPVI with a monovalent affinity of 10 nM or less, more preferably of 1 nM or less, and still more preferably 0.5 nM or less.

In a further embodiment, the present disclosure refers to an isolated antibody or antibody fragment that binds to human GPVI with a monovalent affinity of 70 pM or less. In an embodiment, said antibody or antibody fragment binds to cynomolgus monkey GPVI with a monovalent affinity of 90 pM or less. In an embodiment, said antibody or antibody fragment binds to human GPVI and to cynomolgus monkey GPVI with a monovalent affinity of 100 pM or less.

In yet a further embodiment, the present disclosure refers to an isolated antibody or antibody fragment that binds to mouse GPVI with a monovalent affinity of 30 nM or less, preferably of 9 nM or less, preferably of 1 nM or less. In yet a further embodiment, the present disclosure refers to an isolated antibody or antibody fragment that binds to human and cynomolgus monkey GPVI with a monovalent affinity of 100 pM or less and to mouse GPVI with a monovalent affinity of 9000 pM or less, preferably of 1000 pM or less.

In a further embodiment, the present disclosure refers to an isolated antibody or antibody fragment according to the present disclosure that binds to human GPVI with a monovalent affinity of 100 pM or less and to mouse GPVI with a monovalent affinity of 1000 pM or less. In embodiments, said monovalent affinity is determined in Fab format.

In an embodiment, the monovalent affinity of said isolated antibody or antibody fragment is determined by Solution Equilibrium Titration (SET) as described herein in Example 5 using soluble GPVI.

In an embodiment, said antibody or antibody fragment specific for GPVI comprises
 a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
 b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or
 c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
 d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region of SEQ ID NO: 49.

In a further embodiment, said antibody or antibody fragment comprises
 a) the VH of SEQ ID NO: 17 and the VL of SEQ ID NO: 18 or
 b) the VH of SEQ ID NO: 28 and the VL of SEQ ID NO: 29 or
 c) the VH of SEQ ID NO: 39 and the VL of SEQ ID NO: 40 or
 d) the VH of SEQ ID NO: 50 and the VL of SEQ ID NO: 51 or
 a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In a further embodiment, said antibody or antibody fragment comprises
 a) the HC of SEQ ID NO: 20 and the LC of SEQ ID NO: 19, or
 b) the HC of SEQ ID NO: 21 and the LC of SEQ ID NO: 19, or
 c) the HC of SEQ ID NO: 31 and the LC of SEQ ID NO: 30, or
 d) the HC of SEQ ID NO: 32 and the LC of SEQ ID NO: 30, or
 e) the HC of SEQ ID NO: 42 and the LC of SEQ ID NO: 41, or
 f) the HC of SEQ ID NO: 43 and the LC of SEQ ID NO: 41, or
 g) the HC of SEQ ID NO: 53 and the LC of SEQ ID NO: 52, or
 h) the HC of SEQ ID NO: 54 and the LC of SEQ ID NO: 52.

In an embodiment, said antibody or antibody fragment is a monoclonal antibody or antibody fragment. In an embodiment, said antibody or antibody fragment is an isolated antibody or antibody fragment. In an embodiment, said antibody or antibody fragment is an isolated monoclonal antibody or antibody fragment. In an embodiment, said antibody or antibody fragment is a monovalent antibody or antibody fragment. In one embodiment, said monovalent antibody or antibody fragment is selected from the group consisting of a scFv, an Fv, a Fab and a Fab'. In a preferred embodiment, said monovalent antibody or antibody fragment is a Fab.

In certain embodiments, the present disclosure provides an isolated antibody or antibody fragment specific for GPVI, wherein said antibody or antibody fragment binds to GPVI with an $EC_{50}$ concentration of 60 nM or less, 50 nM or less, 40 nM or less, 30 nM or less, 20 nM or less, 10 nM or less, 5 nM or less, 1 nM or less, 0.9 nM or less, 0.8 nM or less, 0.7 nM or less, 0.6 nM or less, 0.5 nM or less, 0.4 nM or less, 0.4 nM or less, 0.2 nM or less, 0.1 nM or less as determined in a ELISA assay.

In certain embodiments, the present disclosure provides an isolated antibody or antibody fragment specific for GPVI, wherein said antibody or antibody fragment binds to human GPVI, to cynomolgus monkey GPVI and to mouse GPVI with an $EC_{50}$ concentration of 10 nM or less determined in an ELISA assay. In certain embodiments, the present disclosure provides an isolated antibody or antibody fragment specific for GPVI, wherein said antibody or antibody fragment binds to human GPVI and to cynomolgus monkey GPVI with an $EC_{50}$ concentration of 1 nM, to mouse GPVI with an $EC_{50}$ concentration of 10 nM or less and to rat GPVI with an $EC_{50}$ concentration of 60 nM or less determined in an ELISA assay. In a preferred embodiment, the present disclosure provides an isolated antibody or antibody fragment specific for GPVI, wherein said antibody or antibody fragment binds to human GPVI and to cynomolgus monkey GPVI with an $EC_{50}$ concentration of 1 nM, to mouse GPVI with an $EC_{50}$ of 5 nM or less and to rat GPVI with an $EC_{50}$ concentration of 20 nM or less determined in an ELISA assay. In certain embodiments, the present disclosure provides an isolated antibody or antibody fragment specific for GPVI, wherein said antibody or antibody fragment binds to human GPVI, cynomolgus monkey GPVI, mouse GPVI and rat GPVI with an $EC_{50}$ concentration of 16 nM or less determined in a ELISA assay. In certain embodiments the present disclosure provides an isolated antibody or antibody fragment, specific for GPVI, which specifically binds to human GPVI, cynomolgus monkey GPVI and mouse GPVI with an EC50 of 2 nM or less determined in a ELISA assay.

In a further embodiment, said GPVI is coated on the surface of a plate.

In an embodiment, said $EC_{50}$ concentration is determined by an ELISA assay as described herein in Example 3 using soluble GPVI/Fc.

In an embodiment, said antibody or antibody fragment specific for GPVI comprises
 a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or
c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region of SEQ ID NO: 49.

In a further embodiment, said antibody or antibody fragment comprises
a) the VH of SEQ ID NO: 17 and the VL of SEQ ID NO: 18 or
b) the VH of SEQ ID NO: 28 and the VL of SEQ ID NO: 29 or
c) the VH of SEQ ID NO: 39 and the VL of SEQ ID NO: 40 or
d) the VH of SEQ ID NO: 50 and the VL of SEQ ID NO: 51 or
a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In a further embodiment, said antibody or antibody fragment comprises
a) the HC of SEQ ID NO: 20 and the LC of SEQ ID NO: 19, or
b) the HC of SEQ ID NO: 21 and the LC of SEQ ID NO: 19, or
c) the HC of SEQ ID NO: 31 and the LC of SEQ ID NO: 30, or
d) the HC of SEQ ID NO: 32 and the LC of SEQ ID NO: 30, or
e) the HC of SEQ ID NO: 42 and the LC of SEQ ID NO: 41, or
f) the HC of SEQ ID NO: 43 and the LC of SEQ ID NO: 41, or
g) the HC of SEQ ID NO: 53 and the LC of SEQ ID NO: 52, or
h) the HC of SEQ ID NO: 54 and the LC of SEQ ID NO: 52.

In an embodiment, said antibody or antibody fragment is a monoclonal antibody or antibody fragment. In an embodiment, said antibody or antibody fragment is an isolated antibody or antibody fragment. In an embodiment, said antibody or antibody fragment is an isolated monoclonal antibody or antibody fragment. In an embodiment, said antibody or antibody fragment is a monovalent antibody or antibody fragment. In one embodiment, said monovalent antibody or antibody fragment is selected from the group consisting of a scFv, an Fv, a Fab and a Fab'. In a preferred embodiment, said monovalent antibody or antibody fragment is a Fab.

In certain embodiments, the present disclosure provides an isolated antibody or antibody fragment specific for GPVI, wherein said antibody or antibody fragment binds to GPVI with an $EC_{50}$ concentration of 15 nM or less, 14 nM or less, 13 nM or less, 12 nM or less, 11 nM or less, 10 nM or less, 9 nM or less, 8 nM or less, 7 nM or less, 6 nM or less, 5 nM or less, 4 nM or less, 3 nM or less, 2 nM or less, 1 nM or less, 0.9 nM or less, 0.8 nM or less, 0.7 nM or less, 0.6 nM or less, 0.5 nM or less, 0.4 nM or less, 0.4 nM or less, 0.2 nM or less or 0.1 nM or less as determined in a Cell-ELISA assay.

In an embodiment, said $EC_{50}$ concentration is determined in a Cell-ELISA assay as described herein in Example 4.

In certain embodiments, the present disclosure provides an isolated antibody or antibody fragment specific for GPVI, wherein said antibody or antibody fragment binds to human GPVI, cynomolgus monkey GVPI and mouse GPVI with an $EC_{50}$ concentration of 15 nM or less, preferably of 6 nM or less as determined in a Cell-ELISA assay.

In certain embodiments, the present disclosure provides an isolated antibody or antibody fragment specific for GPVI, wherein said antibody or antibody fragment binds to human GPVI with an $EC_{50}$ concentration of 1 nM or less, to cynomolgus monkey GPVI with an $EC_{50}$ concentration of 2 nM or less and to mouse GPVI with an $EC_{50}$ concentration of 6 nM or less as determined in a Cell-ELISA assay. In certain embodiments, the present disclosure provides an isolated antibody or antibody fragment specific for GPVI, wherein said antibody or antibody fragment binds to mouse GPVI with an $EC_{50}$ concentration of 15 nM or less, preferably of 6 nM or less as determined in a Cell-ELISA assay.

In a further embodiment said GPVI is present on the surface of a cell. In a further embodiment said GPVI is present on the surface of a recombinant cell. In a further embodiment said GPVI is present on the surface of a platelet. In a further embodiment said GPVI is present on the surface of human, cynomolgus monkey or mouse platelets.

In an embodiment, said antibody or antibody fragment specific for GPVI comprises
a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or
c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
d) the HCDR1 region of SEQ ID NO: 44, the HCDR2 region of SEQ ID NO: 45, the HCDR3 region of SEQ ID NO: 46, the LCDR1 region of SEQ ID NO.: 47, the LCDR2 region of SEQ ID NO: 48 and the LCDR3 region comprising the amino acid sequence of SEQ ID NO: 49.

In a further embodiment, said antibody or antibody fragment comprises
a) the VH of SEQ ID NO: 17 and the VL of SEQ ID NO: 18 or
b) the VH of SEQ ID NO: 28 and the VL of SEQ ID NO: 29 or
c) the VH of SEQ ID NO: 39 and the VL of SEQ ID NO: 40 or
d) the VH of SEQ ID NO: 50 and the VL of SEQ ID NO: 51 or
a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In a further embodiment, said antibody or antibody fragment comprises
- a) the HC of SEQ ID NO: 20 and the LC of SEQ ID NO: 19, or
- b) the HC of SEQ ID NO: 21 and the LC of SEQ ID NO: 19, or
- c) the HC of SEQ ID NO: 31 and the LC of SEQ ID NO: 30, or
- d) the HC of SEQ ID NO: 32 and the LC of SEQ ID NO: 30, or
- e) the HC of SEQ ID NO: 42 and the LC of SEQ ID NO: 41, or
- f) the HC of SEQ ID NO: 43 and the LC of SEQ ID NO: 41, or
- g) the HC of SEQ ID NO: 53 and the LC of SEQ ID NO: 52, or
- h) the HC of SEQ ID NO: 54 and the LC of SEQ ID NO: 52.

In an embodiment, said antibody or antibody fragment is a monoclonal antibody or antibody fragment. In an embodiment, said antibody or antibody fragment is an isolated antibody or antibody fragment. In an embodiment, said antibody or antibody fragment is an isolated monoclonal antibody or antibody fragment. In an embodiment, said antibody or antibody fragment is a monovalent antibody or antibody fragment. In one embodiment, said monovalent antibody or antibody fragment is selected from the group consisting of a scFv, an Fv, a Fab and a Fab'. In a preferred embodiment, said monovalent antibody or antibody fragment is a Fab. In an embodiment, said Fab is a human Fab.

Functional Embodiments

In general, the antibodies or antibody fragments of the present disclosure can be used to prevent or to inhibit the interaction between GPVI and collagen, thereby preventing, inhibiting or reducing the signaling pathways that are mediated by GPVI and/or modulating the biological pathways and mechanisms in which GPVI is involved.

In one embodiment, the present disclosure pertains to an antibody or antibody fragment specific for GPVI, wherein said antibody or antibody fragment is capable of specifically interfering with GPVI-mediated signal transduction.

Methods for assaying for functional activity may utilize binding assays, such as the enzyme-linked immunosorbent assay (ELISA), radioimmunoassay (RIA), fluorescence activated cell sorting (FACS) and other methods that are well known in the art (see Hampton, R. et al. (1990; Serological Methods a Laboratory Manual, APS Press, St Paul, Minn.) and Maddox, D. E. et al. (1983; J. Exp. Med. 158:1211-1216). Alternatively, assays may test the ability of the antibody or antibody fragments of the present disclosure in eliciting a biological response as a result of binding to GPVI, either in vivo or in vitro. Such assays are described herein. Other suitable assays will be known to those of skill in the art. A method of measuring the binding of GPVI to collagen is not limited to a specific method and can also be done by the other conventional method In one embodiment, the antibody or antibody fragment of the present disclosure antagonizes GPVI activity. In one embodiment, the antibody or antibody fragment of the present disclosure neutralizes the GPVI activity. In one embodiment, the antibody or antibody fragment of the present disclosure inhibits GPVI signaling.

GPVI—Collagen Binding Inhibition

In an embodiment, the antibody or antibody fragment specific for GPVI according to the present disclosure is able to inhibit GPVI binding to collagen. In an embodiment, said antibody or antibody fragment specific for GPVI inhibits the binding of GPVI to collagen. In embodiments, said GPVI is selected from group consisting of human GPVI, cynomolgus monkey GPVI, and mouse GPVI.

In certain embodiments, said antibody or antibody fragment specific for GPVI inhibits the binding of human GPVI, cynomolgus GPVI or mouse GPVI to collagen.

In one embodiment, said antibody or antibody fragment specific for GPVI inhibits the binding of human GPVI, cynomolgus GPVI and mouse GPVI to collagen. In a further embodiment, said antibody or antibody fragment specific for GPVI inhibits the binding of GPVI to collagen, wherein said GPVI is mouse GPVI. In certain embodiments, said antibody or antibody fragment specific for GPVI inhibits the binding of GPVI to collagen, wherein said collagen is human collagen, rat aorta collagen, rabbit aorta collagen or cynomolgus monkey aorta collagen.

In certain embodiments, the antibody or antibody fragment specific for GPVI according to the present disclosure inhibits the binding of human GPVI, cynomolgus monkey GPVI and mouse GPVI to collagen with an $IC_{50}$ concentration of less than 30 nM, less than 20 nM, less than 10 nM, less than 9 nM, less than 8 nM, less than 7 nM, less than 6 nM, less than 5 nM, less than 4 nM, less than 3 nM, less than 2 nM, less than 1 nM, less than 100 pM, less than 90 pM, less than 80 pM, less than 70 pM, less than 60 pM, less than 50 pM, less than 40 pM, less than 30 pM, less than 20 pM, less than 10 pM, less than 9 pM, less than 8 pM, less than 7 pM, less than 6 pM, less than 5 pM, less than 4 pM, less than 3 pM, less than 2 pM or less than 1 pM.

In embodiments, the antibody or antibody fragment specific for GPVI according to the present disclosure inhibits the binding of human GPVI, cynomolgus monkey GPVI and mouse GPVI to collagen with an $IC_{50}$ concentration of 15 nM or less, even more preferably of 10 nM or less. In certain embodiments, said antibody or antibody fragment specific for GPVI inhibits the binding of human GPVI, cynomolgus monkey GPVI and mouse GPVI to collagen with an $IC_{50}$ concentration 10 nM or less.

In certain embodiments, the antibody or antibody fragment specific for GPVI according to the present disclosure inhibits the binding of mouse GPVI to collagen with an IC50 concentration of 30 nM or less, preferably with an $IC_{50}$ concentration of 15 nM or less, preferably with an $IC_{50}$ concentration of 10 nM or less.

In an embodiment, the antibody or antibody fragment specific for GPVI according to the present disclosure, specifically binds to human GPVI, cynomolgus monkey GPVI, mouse GPVI and rat GPVI and inhibits the binding of human GPVI, cynomolgus monkey GPVI and mouse GPVI to collagen with an $IC_{50}$ concentration of less than than 30 nM, less than 20 nM, less than 10 nM, less than 9 nM, less than 8 nM, less than 7 nM, less than 6 nM, less than 5 nM, less than 4 nM, less than 3 nM, less than 2 nM, less than 1 nM, less than 100 pM, less than 90 pM, less than 80 pM, less than 70 pM, less than 60 pM, less than 50 pM, less than 40 pM, less than 30 pM, less than 20 pM, less than 10 pM, less than 9 pM, less than 8 pM, less than 7 pM, less than 6 pM, less than 5 pM, less than 4 pM, less than 3 pM, less than 2 pM or less than 1 pM.

In a further embodiment, the antibody or antibody fragment specific for GPVI according to the present disclosure specifically binds to human GPVI, cynomolgus monkey GPVI, mouse GPVI and rat GPVI and inhibits the binding of human GPVI, cynomolgus monkey GPVI and mouse GPVI to collagen with an $IC_{50}$ concentration of 15 nM or less, more preferably with an IC50 concentration of 10 nM or less. In another embodiment, the antibody or antibody fragment specific for GPVI according to the present disclosure specifically binds to mouse GPVI and rat GPVI and inhibits the binding of mouse GPVI to collagen with an $IC_{50}$ concentration of 15 nM or less, preferably with an IC50 concentration of 10 nM or less.

In an embodiment, the antibody or antibody fragment specific for GPVI according to the present disclosure inhibits the binding of GPVI to collagen by at least 30%, at least 40%, at least 50%, at least 60%, at least 70%, at least 80%, at least 90%, at least 95%, by at least 98%, by 100%.

In an embodiment, the antibody or antibody fragment of the present disclosure inhibits the binding of GPVI to collagen by at least 30%, at least 40%, at least 50%, at least 60%, at least 70%, at least 80%, at least 90%, at least 95%, at least 98%, by 100% at a concentration of 200 nM.

In an embodiment, the antibody or antibody fragment specific for GPVI according to the present disclosure inhibits the binding of GPVI to collagen by at least 98% at a concentration of 200 nM.

In an embodiment, the antibody or antibody fragment specific for GPVI according to the present disclosure inhibits the binding of human GPVI, cynomolgus monkey GPVI and mouse GPVI to collagen by at least 98% at a concentration of 200 nM.

In one embodiment, the antibody or antibody fragment specific for GPVI according to the present disclosure binds to human GPVI, cynomolgus monkey GPVI, mouse GPVI and rat GPVI and inhibits the binding of human GPVI, cynomolgus monkey GPVI and mouse GPVI to collagen by at least 98%.

In yet another embodiment, the antibody or antibody fragment specific for GPVI according to the present disclosure specifically binds to human GPVI, cynomolgus monkey GPVI, mouse GPVI and rat GPVI and inhibits the binding of human GPVI, cynomolgus monkey GPVI and mouse GPVI to collagen by at least 98% at a concentration of 200 nM.

In a further embodiment, the antibody or antibody fragment specific for GPVI according to the present disclosure specifically binds to human GPVI, cynomolgus monkey GPVI, mouse GPVI and rat GPVI and inhibits the binding of human GPVI, cynomolgus monkey GPVI and mouse GPVI to collagen with an $IC_{50}$ concentration of 15 nM or less, preferably with an IC50 concentration of 10 nM or less and inhibits the binding of human GPVI, cynomolgus monkey GPVI and mouse GPVI to collagen by at least 98%.

In a further embodiment, the antibody or antibody fragment specific for GPVI according to the present disclosure specifically binds to human GPVI, cynomolgus monkey GPVI, mouse GPVI and rat GPVI and inhibits the binding of human GPVI, cynomolgus monkey GPVI and mouse GPVI to collagen with an $IC_{50}$ concentration of 15 nM or less, preferably with an IC50 concentration of 10 nM or less and inhibits the binding of human GPVI, cynomolgus monkey GPVI and mouse GPVI to collagen by at least 98% at a concentration of 200 nM.

In yet another embodiment, the antibody or antibody fragment specific for GPVI according to the present disclosure specifically binds to human GPVI, cynomolgus monkey GPVI, mouse GPVI and rat GPVI and inhibits the binding of human GPVI, cynomolgus monkey GPVI and mouse GPVI to collagen by at least at least 98% with an $IC_{50}$ concentration of less than 15 nM, preferably with an $IC_{50}$ concentration of 10 nM or less and with an monovalent affinity to GPVI with a dissociation rate constant ($K_D$) of 10 nM or less, preferably of 1 nM or less.

In an embodiment, said antibody or antibody fragment specific for GPVI according to the present disclosure comprises
  a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
  b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or
  c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
  d) the HCDR1 region of SEQ ID NO: 44, the HCDR2 region of SEQ ID NO: 45, the HCDR3 region of SEQ ID NO: 46, the LCDR1 region of SEQ ID NO.: 47, the LCDR2 region of SEQ ID NO: 48 and the LCDR3 region comprising the amino acid sequence of SEQ ID NO: 49.

In a further embodiment, said antibody or antibody fragment comprises
  a) the VH of SEQ ID NO: 17 and the VL of SEQ ID NO: 18 or
  b) the VH of SEQ ID NO: 28 and the VL of SEQ ID NO: 29 or
  c) the VH of SEQ ID NO: 39 and the VL of SEQ ID NO: 40 or
  d) the VH of SEQ ID NO: 50 and the VL of SEQ ID NO: 51 or
  a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In a further embodiment, said antibody or antibody fragment comprises
  a) the HC of SEQ ID NO: 20 and the LC of SEQ ID NO: 19, or
  b) the HC of SEQ ID NO: 21 and the LC of SEQ ID NO: 19, or
  c) the HC of SEQ ID NO: 31 and the LC of SEQ ID NO: 30, or
  d) the HC of SEQ ID NO: 32 and the LC of SEQ ID NO: 30, or
  e) the HC of SEQ ID NO: 42 and the LC of SEQ ID NO: 41, or
  f) the HC of SEQ ID NO: 43 and the LC of SEQ ID NO: 41, or
  g) the HC of SEQ ID NO: 53 and the LC of SEQ ID NO: 52, or
  h) the HC of SEQ ID NO: 54 and the LC of SEQ ID NO: 52.

In an embodiment, said antibody or antibody fragment is a monoclonal antibody or antibody fragment. In an embodiment, said antibody or antibody fragment is an isolated antibody or antibody fragment. In an embodiment, said antibody or antibody fragment is an isolated monoclonal antibody or antibody fragment. In an embodiment, said antibody or antibody fragment is a monovalent antibody or antibody fragment. In one embodiment, said monovalent antibody or antibody fragment is selected from the group consisting of a scFv, an Fv, a Fab and a Fab'. In a preferred embodiment, said monovalent antibody or antibody fragment is a Fab. In an embodiment, said Fab is a human Fab.

The $IC_{50}$ concentration and/or the maximum achieved inhibitory effect can be determined by ELISA, SET, FACS or MSD (Meso Scale Discovery). In an embodiment, the $IC_{50}$ concentration and/or the maximum achieved inhibitory effect is determined in a Receptor Inhibition Assay as described herein in Example 6. In an embodiment, the $IC_{50}$ concentration and/or the maximum achieved inhibitory effect can be determined by the method as described herein in Example 6.

Cell Adhesion

In an embodiment, the antibody or antibody fragment specific for GPVI according to the present disclosure inhibits the adhesion of human GPVI expressing cells to a ligand of GPVI, such as collagen. In an embodiment, said antibody or antibody fragment inhibits the adhesion of GPVI expressing cells to collagen. In an embodiment, said antibody or antibody fragment inhibits the adhesion of human GPVI expressing cells to collagen. In an embodiment, said antibody or antibody fragment inhibits the adhesion of human GPVI expressing cells on a collagen coated surface. In an embodiment, said antibody or antibody fragment inhibits the adhesion of human GPVI expressing cells on a collagen coated surface.

In an embodiment, the antibody or antibody fragment specific for GPVI according to the present disclosure inhibits the adhesion of GPVI expressing cells to collagen with an $IC_{50}$ concentration of 3 nM or less, 2 nM or less, 1 nM or less, 100 pM or less, 90 pM or less, 80 pM or less, 70 pM or less, 60 pM or less, 50 pM or less, 40 pM or less, 30 pM or less, 20 pM or less, 10 pM or less, 9 pM or less, 8 pM or less, 7 pM or less, 6 pM or less, 5 pM or less, 4 pM or less, 3 pM or less, 2 pM or less or 1 pM or less.

In an embodiment, the antibody or antibody fragment specific for GPVI according to the present disclosure inhibits the adhesion of human GPVI expressing cells on collagen with an $IC_{50}$ concentration of 3 nM or less, preferably of 2 nM or less.

In yet another embodiment, the antibody or antibody fragment specific for GPVI according to the present disclosure specifically binds to human GPVI, cynomolgus monkey GPVI, mouse GPVI and rat GPVI and inhibits the adhesion of human GPVI expressing cells on collagen with an $IC_{50}$ concentration of 3 nM or less, preferably of 2 nM or less.

In an embodiment, the antibody or antibody fragment specific for GPVI according to the present disclosure inhibits the adhesion of GPVI expressing cells on collagen by at least 10%, by at least 20%, by at least 30%, buy at least 40%, 50%, at least 60%, at least 70%, at least 80%, at least 90%, at least 95%, by essentially 100%.

In an embodiment, the antibody or antibody fragment specific for GPVI according to the present disclosure inhibits the adhesion of GPVI expressing cells on collagen by at least 10%, by at least 20%, by at least 30%, buy at least 40%, 50%, at least 60%, at least 70%, at least 80%, at least 90%, at least 95%, at least 98%, by 100% at a concentration of 200 nM.

In an embodiment, said antibody or antibody fragment of the present disclosure inhibits the adhesion of human GPVI expressing cells on collagen by at least 85% at a concentration of 200 nM.

In yet another embodiment, the antibody or antibody fragment specific for GPVI according to the present disclosure specifically binds to human GPVI, cynomolgus monkey GPVI, mouse GPVI and rat GPVI and inhibits the adhesion of human GPVI expressing cells on collagen by at least 85% at a concentration of 200 nM.

In yet another embodiment, the antibody or antibody fragment specific for GPVI according to the present disclosure specifically binds to human GPVI, cynomolgus monkey GPVI, mouse GPVI and rat GPVI and inhibits the adhesion of human GPVI expressing cells on collagen with an $IC_{50}$ concentration of 3 nM or less, preferably of 2 nM or less and inhibits the adhesion of human GPVI expressing cells on collagen by at least 85% at a concentration of 200 nM.

In one embodiment, said antibody or antibody fragment specific for GPVI according to the present disclosure comprises
  a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
  b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or
  c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ LD NO: 38, or
  d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region of SEQ ID NO: 49.

In a further embodiment, said antibody or antibody fragment comprises
  a) the VH of SEQ ID NO: 17 and the VL of SEQ ID NO: 18 or
  b) the VH of SEQ ID NO: 28 and the VL of SEQ ID NO: 29 or
  c) the VH of SEQ ID NO: 39 and the VL of SEQ ID NO: 40 or
  d) the VH of SEQ ID NO: 50 and the VL of SEQ ID NO: 51 or
    a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In a further embodiment, said antibody or antibody fragment comprises
  a) the HC of SEQ ID NO: 20 and the LC of SEQ ID NO: 19, or
  b) the HC of SEQ ID NO: 21 and the LC of SEQ ID NO: 19, or
  c) the HC of SEQ ID NO: 31 and the LC of SEQ ID NO: 30, or
  d) the HC of SEQ ID NO: 32 and the LC of SEQ ID NO: 30, or
  e) the HC of SEQ ID NO: 42 and the LC of SEQ ID NO: 41, or
  f) the HC of SEQ ID NO: 43 and the LC of SEQ ID NO: 41, or
  g) the HC of SEQ ID NO: 53 and the LC of SEQ ID NO: 52, or
  h) the HC of SEQ ID NO: 54 and the LC of SEQ ID NO: 52.

In an embodiment, said antibody or antibody fragment is a monoclonal antibody or antibody fragment. In an embodiment, said antibody or antibody fragment is an isolated antibody or antibody fragment. In an embodiment, said antibody or antibody fragment is an isolated monoclonal antibody or antibody fragment. In an embodiment, said antibody or antibody fragment is a monovalent antibody or antibody fragment. In one embodiment, said monovalent antibody or antibody fragment is selected from the group consisting of a scFv, an Fv, a Fab and a Fab'. In a preferred embodiment, said monovalent antibody or antibody fragment is a Fab. In an embodiment, said Fab is a human Fab.

The $IC_{50}$ concentration and/or the maximum achieved inhibitory effect can be determined by ELISA, SET, FACS or MSD (Meso Scale Discovery). In an embodiment, the $IC_{50}$ concentration and/or the maximum achieved inhibitory effect is determined in a Cell Adhesion Assay as described herein in Example 7. In an embodiment, the $IC_{50}$ concentration and/or the maximum achieved inhibitory effect can be determined by the method as described herein in Example 7.

Aggregation

The antibody or antibody fragment specific for GPVI according to the present disclosure is capable to inhibit platelet aggregation induced by a GPVI ligand, such as collagen, both in human platelet rich plasma and in human whole blood.

In an embodiment, said antibody or antibody fragment inhibits platelet aggregation in response to a ligand of GPVI, such as collagen. In an embodiment, the antibody or antibody fragment specific for GPVI according to the present disclosure inhibits collagen-induced platelet aggregation. In an embodiment, said collagen is human, rabbit or cynomolgus monkey collagen.

In one embodiment, the antibody or antibody fragment specific for GPVI according to the present disclosure inhibits collagen-induced human platelet aggregation when used at a concentration of 0.25 µg/mL or more, of 0.5 µg/mL or more, of 1 µg/mL or more, of 2 µg/mL or more, of 3.3 µg/mL or more, of 5 µg/mL or more, of 10 µg/mL or more.

In an embodiment, the antibody or antibody fragment specific for GPVI according to the present disclosure inhibits collagen-induced human platelet aggregation by at least 50%, by at least 60%, by at least 70%, by at least 80%, by at least 90%, by at least 95%, by at least 98%, by 100%. In an embodiment, the antibody or antibody fragment according to the present disclosure inhibits collagen-induced human platelet aggregation by at least 50%, by at least 60%, by at least 70%, by at least 80%, by at least 90%, by at least 95%, by at least 98%, by 100% when used at a concentrations of at least 3.3 µg/ml.

In an embodiment, the antibody or antibody fragment according to the present disclosure inhibits collagen-induced human platelet aggregation by 100%. In an embodiment, the antibody or antibody fragment according to the present disclosure inhibits collagen-induced human platelet aggregation by essentially 100% when used at a concentrations of 10 µg/mL or more.

In an embodiment, the antibody or antibody fragment according to the present disclosure inhibits collagen-induced human platelet aggregation by at least 70% when used at a concentrations of 3.3 µg/mL.

In an embodiment, the antibody or antibody fragment according to the present disclosure inhibits cynomolgus monkey aorta collagen-induced human platelet aggregation. In a further embodiment, the antibody or antibody fragment specific for GPVI according to the present disclosure inhibits cynomolgus aorta collagen-induced human platelet aggregation when used at a concentration of at least 3.3 µg/mL or more, preferably when used at a concentration of 10 µg/mL. In an embodiment, the antibody or antibody fragment according to the present disclosure inhibits cynomolgus aorta collagen-induced human platelet aggregation by at least 50% when used at a concentrations of 10 µg/mL.

In an embodiment, the antibody or antibody fragment according to the present disclosure inhibits collagen-induced platelet aggregation, but has no effect on platelet aggregation induced by other platelet aggregation inducing substances (e.g. other agonists of GPVI), such as ADP, TRAP or PAR1.

Furthermore, the antibody or antibody fragment specific for GPVI according to the present disclosure is also able to inhibit human atherosclerotic plaque material-induced platelet aggregation. In an embodiment, the antibody or antibody fragment of the present disclosure inhibits human atherosclerotic plaque-induced human platelet aggregation by essentially 100%. In an embodiment, the antibody or antibody fragment of the present disclosure inhibits human atherosclerotic plaque-induced human platelet aggregation by 100% when used at a concentrations of 2 µg/mL or more.

In one embodiment said antibody or antibody fragment specific for GPVI according to the present disclosure comprises
  a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
  b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or
  c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
  d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region of SEQ ID NO: 49.

In an embodiment, said antibody or antibody fragment comprises
  a) the VH of SEQ ID NO: 17 and the VL of SEQ ID NO: 18 or
  b) the VH of SEQ ID NO: 28 and the VL of SEQ ID NO: 29 or
  c) the VH of SEQ ID NO: 39 and the VL of SEQ ID NO: 40 or
  d) the VH of SEQ ID NO: 50 and the VL of SEQ ID NO: 51 or
      a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In a further embodiment, said antibody or antibody fragment comprises
  a) the HC of SEQ ID NO: 20 and the LC of SEQ ID NO: 19, or
  b) the HC of SEQ ID NO: 21 and the LC of SEQ ID NO: 19, or
  c) the HC of SEQ ID NO: 31 and the LC of SEQ ID NO: 30, or d) the HC of SEQ ID NO: 32 and the LC of SEQ ID NO: 30, or e) the HC of SEQ ID NO: 42 and the LC of SEQ ID NO: 41, or f) the HC of SEQ ID NO: 43 and the LC of SEQ ID NO: 41, or g) the HC of SEQ ID NO: 53 and the LC of SEQ ID NO: 52, or h) the HC of SEQ ID NO: 54 and the LC of SEQ ID NO: 52.

In an embodiment, said antibody or antibody fragment is a monoclonal antibody or antibody fragment. In an embodiment, said antibody or antibody fragment is an isolated antibody or antibody fragment. In an embodiment, said antibody or antibody fragment is an isolated monoclonal antibody or antibody fragment. In an embodiment, said antibody or antibody fragment is a monovalent antibody or antibody fragment. In one embodiment, said monovalent antibody or antibody fragment is selected from the group consisting of a scFv, an Fv, a Fab and a Fab'. In a preferred embodiment, said monovalent antibody or antibody fragment is a Fab. In an embodiment, said Fab is a human Fab.

The achieved inhibitory effect on aggregation can be determined by Impedance Aggregometry as described herein in Example 9 or Example 10.

The antibody for antibody fragment specific for GPVI according to the present disclosure is also able to inhibit platelet aggregation under flow on a collagen coated surface. Moreover, the antibody for antibody fragment of the present disclosure is also able to inhibit human platelet aggregation under flow on a human atherosclerotic plaque coated surface. The antibody for antibody fragments of the present disclosure are also able to inhibit platelet aggregation under flow on a human atherosclerotic plaque coated surface. The antibody or antibody fragments specific for GPVI of the present disclosure are also able to inhibit platelet aggregation under flow induced by human atherosclerotic plaque.

In certain embodiments, the antibody or antibody fragment specific for GPVI of the present disclosure inhibits human atherosclerotic plaque-induced platelet aggregation under flow by at least 95%. In certain embodiments, the antibody or antibody fragment of the present disclosure inhibits human atherosclerotic plaque-induced platelet aggregation under flow by at least 95% when used at a concentrations of 2.0 µg/mL or more. In certain embodiments, the antibody or antibody fragment of the present disclosure inhibits human atherosclerotic plaque-induced human platelet aggregation under flow by at least 95% when used at an antibody concentrations of 2.0 µg/mL or more. In certain embodiments, the antibody or antibody fragment of the present disclosure inhibits human atherosclerotic plaque-induced platelet aggregation under flow and over time by at least 95% when used at an antibody concentrations of 2.0 µg/mL or more.

In certain embodiments, the antibody or antibody fragment of the present disclosure is more efficacious in inhibiting atherosclerotic plaque-induced platelet aggregation under flow and over time when compared to the combination of acetylsalicylic acid and Ticagrelor. In certain embodiments, the antibody or antibody fragment of the present disclosure is more efficacious to inhibit arteriosclerotic plaque-induced platelet aggregation under flow over time when compared to the combination of acetylsalicylic acid and Ticagrelor when used at an antibody concentrations of 2.0 µg/mL.

In one embodiment said antibody or antibody fragment specific for GPVI according to the present disclosure comprises a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region of SEQ ID NO: 49.

In an embodiment, said antibody or antibody fragment comprises a) the VH of SEQ ID NO: 17 and the VL of SEQ ID NO: 18 or b) the VH of SEQ ID NO: 28 and the VL of SEQ ID NO: 29 or c) the VH of SEQ ID NO: 39 and the VL of SEQ ID NO: 40 or d) the VH of SEQ ID NO: 50 and the VL of SEQ ID NO: 51 or a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In a further embodiment, said antibody or antibody fragment comprises a) the HC of SEQ ID NO: 20 and the LC of SEQ ID NO: 19, or b) the HC of SEQ ID NO: 21 and the LC of SEQ ID NO: 19, or c) the HC of SEQ ID NO: 31 and the LC of SEQ ID NO: 30, or d) the HC of SEQ ID NO: 32 and the LC of SEQ ID NO: 30, or e) the HC of SEQ ID NO: 42 and the LC of SEQ ID NO: 41, or f) the HC of SEQ ID NO: 43 and the LC of SEQ ID NO: 41, or g) the HC of SEQ ID NO: 53 and the LC of SEQ ID NO: 52, or h) the HC of SEQ ID NO: 54 and the LC of SEQ ID NO: 52.

In an embodiment, said antibody or antibody fragment is a monoclonal antibody or antibody fragment. In an embodiment, said antibody or antibody fragment is an isolated antibody or antibody fragment. In an embodiment, said antibody or antibody fragment is an isolated monoclonal antibody or antibody fragment. In an embodiment, said antibody or antibody fragment is a monovalent antibody or antibody fragment. In one embodiment, said monovalent antibody or antibody fragment is selected from the group consisting of a scFv, an Fv, a Fab and a Fab'. In a preferred embodiment, said monovalent antibody or antibody fragment is a Fab. In an embodiment, said Fab is a human Fab.

The achieved inhibitory effect on aggregation under flow conditions can be determined by as described herein in Example 11.

In Vivo Activity

The antibody or antibody fragment specific for GPVI according to the present disclosure is also able to inhibit or prevent thrombus formation (e.g. platelet aggregation and adhesion) in vivo.

In an embodiment, the antibody or antibody fragment according to the present disclosure inhibits the ability of platelets to form thrombus in response to collagen binding in vivo.

In the method described in Example 12 herein, the antibody fragment according to the present disclosure has an activity that at the antibody concentration of 3 mg/kg or less, of 1 mg/kg or less, of 0.3 mg/kg or less or of 0.1 mg/kg or less, makes the collagen-induced thrombus formation of the platelet decrease by 20%, equal to or more than 40%, equal to or more than 60%, equal to or more than 80%, equal to or more than 90% or equal to or more than 95% in comparison to the value prior to the administration or the control value.

In the method described in Example 12 herein, the antibody fragment has an in vivo activity that at the antibody concentration of about 3.3 mg/kg makes thrombus formation of the platelet decrease equal to by 20%, equal to or more than 40%, more preferably equal to or more than 60%, equal to or more than 80%, equal to or more than 90% or equal to or more than 95% in comparison to the value prior to the administration or the control value.

In the method described in Example 12 herein, the antibody fragment has an in vivo activity that at the antibody concentration of about 3.3 mg/kg substantially fully prevents thrombus formation in vivo.

Safety

Bleeding

In an embodiment, the antibody or antibody fragment specific for GPVI according to the present disclosure does not induce an increase in bleeding time in a subject. In one embodiment, the antibody or antibody fragment of the present disclosure does not substantially or significantly prolongs the bleeding time in a subject. In one embodiment, the antibody or antibody fragment of the present disclosure does not prolong the bleeding time in a subject. In an embodiment, the ability of the antibody or antibody fragment of the present disclosure to prolong bleeding time in a subject is weak.

The bleeding time can be assayed by the publicly known method, and specifically the method described in Example 14 may be applicable.

In an embodiment, the antibody or antibody fragment specific for GPVI of the present disclosure substantially does not prolong the bleeding time in a subject at a therapeutically effective amount, for example, 0.3 mg/kg, 1 mg/kg, 3 mg/kg, or 10 mg/kg. In an embodiment, the antibody or antibody fragment of the present disclosure substantially does not prolong the bleeding time at a concentration of 10 mg/kg.

Specifically, the bleeding time is less or equal to 5-fold, preferably less or equal to 3-fold, less or equal to 2-fold, less or equal to 1.5-fold, or substantially equal as the value prior to administration, normal value or control.

The antibody or antibody fragment of the present disclosure substantially does not prolong the bleeding time at the therapeutically effective amount when co-administered with acetylsalicylic acid compared to the administration with acetylsalicylic acid alone.

The antibody or antibody fragment of the present disclosure does not prolong the bleeding time at a therapeutically effective amount, for example, 0.3 mg/kg, 1 mg/kg, 3 mg/kg or 10 mg/kg when co-administered with acetylsalicylic acid (ASA) compared to the administration with acetylsalicylic acid alone.

Platelet Count

The antibody or antibody fragment specific for GPVI according to the present disclosure does substantially not induce a decrease in platelet count in vivo. In one embodiment, the antibody or antibody fragment of the present disclosure does substantially not induce a decrease in platelet count in vivo when administered to a subject. Preferably, the antibody or antibody fragment of the present disclosure has no activity on platelet count in vivo.

Accordingly, in one embodiment, the antibody or antibody fragment specific for GPVI of the present disclosure does substantially not induce thrombocytopenia when administered to a subject. In a further embodiment, said antibody or antibody fragment of the present disclosure does substantially not induce thrombocytopenia in vivo.

Thrombocytopenia in vivo can be determined by collecting blood with time after in vivo administration of the antibody or antibody fragment of the present disclosure, calculating the number of platelets with a conventional method and comparing the number with a value prior to administration or the number of platelets of an individual as a control. Thrombocytopenia in vivo can be determined as described in Example 15 of the present disclosure.

In one embodiment, the antibody or antibody fragment specific for GPVI of the present disclosure does not induce a decrease in platelet count, i.e., thrombocytopenia, when administered in vivo, such as, for example, when administered at a therapeutically effective amount. In one embodiment, the antibody or antibody fragment of the present disclosure does not induce a decrease in platelet count, i.e., thrombocytopenia, when administered in vivo, such as, for example, when administered at an amount ranging from 0.01 mg/kg to 100 mg/kg. In one embodiment, the antibody or antibody fragment of the present disclosure does not induce a decrease in platelet count, i.e., thrombocytopenia, when administered in vivo when administered at a concentration of 10 mg/kg.

The platelet number reduced by the antibody or antibody fragment of the present disclosure is preferably equal to or more than 50%, equal to or more than 70%, equal to or more than 90% or substantially the same of the platelet number prior to the administration of said antibody or control when the value prior to the administration or the control value is set as 100%.

The platelet number reduced by the antibody or antibody fragment of the present disclosure is equal to or more than 50%, equal to or more than 70%, equal to or more than 90%, or preferably almost the same of the platelet number prior to the administration of said antibody or control when the value prior to the administration or the control value is set as 100% and when the antibody is administered at a concentration of e.g. 0.3 mg/kg, preferably 1 mg/kg, more preferably 3 mg/kg, further preferably 10 mg/kg.

Cell Surface Expression/Shedding/Internalization

GPVI can be downregulated or depleted from the platelet membrane or surface. This modulation of GPVI protein levels can be triggered by ligand (such as collagen) binding and subsequent receptor activation resulting for instance in the cleavage of the ectodomain of GPVI (e.g. shedding) or in ligand-induced GPVI receptor internalization. Platelet activation may also occur upon engagement of an antibody specific for GPVI which mimics the function of the ligand. In cases where an antibody specific for GPVI mimics the function of an agonist ligand of GPVI, the antibody can be considered as an agonist of GPVI.

In an embodiment, the antibody or antibody fragment of the present disclosure does substantially not activate a platelet, preferably has no activity. In an embodiment, the antibody or antibody fragment of the present disclosure does substantially not activate a platelet in vivo, preferably has no activity. In an embodiment, the antibody or antibody fragment of the present disclosure binds to GPVI on the surface of a platelet and prevents the activation of the GPVI pathway on platelets.

In one embodiment, the antibody or antibody fragment of the present disclosure does not induce depletion of GPVI from the surface of a platelet in vivo. In one embodiment, the antibody or antibody fragment of the present disclosure does not induce depletion of GPVI from the platelet surface when administered to a subject. In an embodiment, the antibody or antibody fragment of the present disclosure does not substantially depletes GPVI from the platelet surface in vivo. In an embodiment, the antibody or antibody fragment of the present disclosure does not substantially depletes GPVI from the platelet surface when contacting said antibody or antibody fragment with a platelet in vivo.

In one embodiment, the antibody or antibody fragment of the present disclosure does not induce depletion of GPVI from the platelet surface when administered in vivo, such as, for example, when administered at a therapeutically effective amount ranging from 0.01 to 500 mg. In one embodiment, the antibody or antibody fragment of the present disclosure does not induce depletion of GPVI from the platelet surface when administered in vivo at a concentration of 10 mg/kg.

In an embodiment, the antibody or antibody fragment of the present disclosure does not substantially depletes GPVI from the platelet surface by shedding of platelet GPVI, especially, shedding of platelet GPVI by metalloprotease-mediated cleavage accompanying platelet activation, when contacting said antibody or antibody fragment with said platelet.

The antibody or antibody fragment of the present disclosure does not substantially induce shedding of GPVI from the platelet surface, in particular shedding of GPVI from platelets by metalloprotease-mediated cleavage accompanying platelet activation. In an embodiment, the antibody or antibody fragment of the present disclosure does not induce depletion of GPVI from the platelet surface by bringing the antibody or antibody fragment specific for GPVI according to the present disclosure in contact with the platelet, in particular, by bringing said antibody or antibody fragment in contact with the platelet in vivo.

Such activity can be confirmed by bringing the antibody or antibody fragment of the present disclosure in contact with the platelet for a given time followed by isolating the platelet, and assaying the expression level of GPVI on the surface. The expression level of GPVI can be measured by the conventional method using FACS, etc., and the specific method is illustrated in Example 16.

The antibody or antibody fragment of the present disclosure does not induce depletion of GPVI from the platelet surface equal to or more than 20%, equal to or more than 40%, equal to or more than 60%, equal to or more than 80%, equal to or more than 90%, in comparison with the value prior to administration to a subject or the control value at a concentration of 0.1 mg/kg or more, 0.3 mg/kg or more, 1 mg/kg or more, 3 mg/kg or 10 mg/kg or more.

The antibody or antibody fragment of the present disclosure does not substantially depletes GPVI on the platelet surface via internalization of GPVI from the platelet by contacting the platelet with the antibody or antibody fragment of the present disclosure.

Platelet Activation

Antibodies when present as full immunoglobulins are bivalent molecules and as such can induce GPVI receptor clustering on the surface of platelets and therefore platelet activation, similar to its natural agonist ligands, such as collagen. To circumvent this, the inventors of the present disclosure have developed monovalent antibody or antibody fragments, in particular Fab fragments specific for GPVI.

However, Fabs which in nature do exist only as a degradation product of immunoglobulins, reveal a potential to still induce platelet activation in a patient specific manner. This is thought to be caused by the C-terminal end (C-terminus) of a Fab, which forms an epitope that may be recognized and specifically bound by pre-existing antibodies present in a subject's serum. These pre-existing antibodies then may elicit an immune response leading to unwanted platelet activation due to the restoration of a bivalent or multivalent antibody molecule. Amino acid sequences that form the epitopes for such anti-Fab antibodies can be referred to as auto-antigenic sequences (Kormeier et al. (1968) J. Immunol. 100(3); 612-21; Persselin and Stevens (1985) J. Clin. Invest. 76; 723-30). Accordingly, the term "non-auto-antigenic sequence" as used herein refers to an amino acid sequence that is not or does not form an epitope recognized by pre-existing antibodies present is a subject.

In order to determine whether an amino acid sequence acts as an auto-antigenic sequence, peptide constructs comprising the specific sequence to be tested can be exposed to human sera to determine whether antibodies are present in the sera which recognize and specifically bind to the peptide constructs. More specifically, in order to identify whether a particular amino acid sequence of an immunoglobulin is an auto-antigenic sequence, IgG molecules can, for example, be cleaved with a panel of proteases to provide IgG fragments that contain different sequences at the C-terminal region. Alternatively, peptides and polypeptides can be produced by peptide synthesis or recombinant DNA technology which are modelled upon the sequence of the IgG C-terminal region. In either case, human sera can be screened to determine whether pre-existing antibodies are present which bind to a particular exposed C-terminal amino acid sequence or synthetic peptide, respectively.

To offer a safe therapeutic for the treatment of ischemic events, it has to be ensured that this activating potential of the developed antibody fragment, such as a Fab, is not present or very weak. Accordingly, in an embodiment, the Fab specific for GPVI according to the present disclosure does substantially not activate platelets, preferably has no activity. The activation of a platelet can be measured by known methods, and an expression level of a platelet surface antigen, preferably CD62P can be used as an index.

For example, a method of isolating a platelet from a subject to whom the monovalent antibody or antibody fragment has been administered after a given period and measuring the expression level of CD62P by a conventional method, a method of bringing the monovalent antibody or antibody fragment specific for GPVI according to the present disclosure in contact with a platelet isolated from a subject, and assaying the expression level of CD62P after a given period by a conventional method, and the like are included. A specific method is shown in Example 13.

Accordingly, in an embodiment, the Fab specific for GPVI according to the present disclosure does substantially not activate a platelet due to recognition of said Fab by anti-Fab antibodies present in a subject's serum. In a further embodiment, the Fab specific for GPVI of the present disclosure does substantially not induce expression of a cell surface activation marker on platelet such as CD62P.

The inventors of the present application demonstrated that a modification at the C-terminus of the Fab heavy chain can further reduce, prevent or inhibit the potential of such Fab to induce platelet activation e.g. by preventing recognition of said Fab specific for GPVI by anti-Fab antibodies present in a subject's serum.

Herein, the "prevention of recognition by" or "prevention of binding of" means that a Fab specific for GPVI according to the present disclosure does not cross-link GPVI on the platelet surface and activate GPVI signaling due to the presence of anti-Fab antibodies present in a subject's serum. Such cross-linking may mimic the activity of natural ligands (such as collagen) resulting in GPVI receptor activation. In other words, a Fab of the present disclosure may act as agonist instead of acting as antagonists. An antagonistic GPVI specific antibody or antibody fragment which neutralizes GPVI receptor function or an agonistic GPVI specific antibody or antibody fragment that activates the function of GPVI can be assessed by assaying an in vivo marker that reflects the function of GPVI.

Accordingly, the present disclosure provides an antibody fragment specific for GPVI comprising a modified heavy chain constant region. In an embodiment, said antibody fragment is a Fab. Such modifications of the heavy chain constant region comprise addition or substitutions of one or more amino acid residue(s) at or to the C-terminus of the Fab heavy chain.

Accordingly, the present disclosure provides a Fab specific for GPVI comprising a modified heavy chain constant region, wherein the modified heavy chain constant region prevents or inhibits recognition of said Fab by anti-Fab antibodies present in a subject's serum.

In an embodiment of the present disclosure, the heavy chain constant region of a Fab specific for GPVI can be modified by the addition or substitution of one or more amino acid(s), preferably by addition or substitution of more than one amino acid, such as an amino acid sequence (e.g. a polypeptide). Such an added or substituted polypeptide can be any amino acid sequence as long as it is able to constitute a non-auto-antigenic sequence when introduced into the Fab of the present disclosure but without interfering with the binding of said Fab to GPVI.

As used herein, "engineered" or "modified" refers to a Fab that is genetically engineered to contain an amino acid extension (e.g. addition) or substitution at the C-terminus of the Fab heavy chain.

In an embodiment, the polypeptide is added to the C-terminus of the Fab heavy chain. In an embodiment, the polypeptide is added to the C-terminus of the CH1 domain of a Fab. Alternatively, the polypeptide is substituting the hinge portion at the C-terminus of the Fab heavy chain if present. In an embodiment, said hinge portion of a Fab comprises or consist of the amino acid sequence EPKSC (SEQ ID NO: 101).

As such, the present disclosure provides a Fab specific for GPVI according to the present disclosure, comprising a modified heavy chain constant region, wherein the modified heavy chain constant region comprises in order from the N-terminus to the C-terminus a CH1 domain and a polypeptide being able to constitute a non-auto-antigenic sequence, wherein said modified heavy chain constant region prevents or inhibits recognition of said Fab by anti-Fab antibodies present in a subject's serum.

In an embodiment, said subject is a human. In an embodiment, said CH1 domain is a human CH1 domain.

In an embodiment, said polypeptide constitutes a non-auto-antigenic sequence. In an embodiment, said polypeptide comprises 1 to 100 amino acids, 1 to 50 amino acids, 1 to 20 amino acids, 1 to 15 amino acids or 1 to 10 amino acids or 1 to 5 amino acids or 1 amino acid.

In an embodiment, said polypeptide comprise only one cysteine which allows the formation of a disulfide bond between the heavy chain and the light chain of the Fab and thus stabilizes the molecule. In a particular embodiment, said cysteine is the last amino-acid residue of the modified heavy chain constant region of the Fab of the present disclosure. In further embodiments of the present disclosure, the cysteine does not allow the formation of disulfide bonds between the heavy chain constant region of a first Fab molecule and the heavy chain constant region of a second Fab molecule. In a further embodiments of the present disclosure, the non-auto-antigenic sequence prevents the formation of (Fab)$_2$ molecules. In a further embodiment of the present disclosure, said polypeptide contains not more than one cysteine.

In an embodiment, the polypeptide being able to constitute a non-auto-antigenic sequence comprises the amino acid sequence ERRX2X3G1GHKC (SEQ ID NO: 102), wherein X2 and X3 can be any natural occurring amino acid residue except cysteine. In an embodiment, said polypeptide comprises or consist of the amino acid sequence selected from the group consisting of ERRNGGIGHKC (SEQ ID NO: 103), EERNGGIGHKC (SEQ ID NO: 104), ERRQGGIGHKC (SEQ ID NO: 105) and VPREC (SEQ ID NO: 106). In an embodiment, the said polypeptide consists of the amino acid sequence ERRQGGIGHKC (SEQ ID NO: 105). It is within the scope of the disclosure, that said polypeptide being able to constitute a non-auto-antigenic sequence may comprise additional amino-acid substitution, for instance in order to remove potential post-translational modification sites or potential T-cell epitopes present in a produced Fab of the present disclosure.

As such, the present disclosure provides a Fab specific for GPVI according to the present disclosure comprising a modified heavy chain constant region, wherein the modified heavy chain constant region comprises in order from the N-terminus to the C-terminus a CH1 domain and a polypeptide being able to constitute a non-auto-antigenic sequence when added to the C-terminus of said Fab, wherein said polypeptide consists of the amino acid sequence ERRQGGIGHKC (SEQ ID NO: 105), wherein said modified heavy chain constant region prevent or inhibits recognition of said Fab by anti-Fab antibodies present in a subject's serum.

In an embodiment, said CH1 domain is selected from the group consisting of: a human IgG1 CH1 domain, a human IgG2 CH1 domain, a human IgG3 CH1 domain and a human IgG4 CH1 domain. In one embodiments, said CH1 domain is a human IgG1 CH1 domain. In embodiments, said CH1 domain is a wildtype human IgG1 CH1 domain, any allotype of a wildtype human IgG1 CH1 domain or comprises an amino acid sequence that is at least 95% identical to the amino acid sequence of a wildtype human IgG1 CH1 domain.

In certain embodiments, said modified heavy chain constant region consists the amino acid sequence selected from the group consisting of:

```
                                           (SEQ ID NO: 107)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKIVP

REC,
                                           (SEQ ID NO: 108)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVER

RNGGIGHKC
                                           (SEQ ID NO: 109)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVEKKVER

RNGGIGHKC,
                                           (SEQ ID NO: 110)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKGVER

RNGGIGHKC,
                                           (SEQ ID NO: 111)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKEVER

RNGGIGHKC,
                                           (SEQ ID NO: 112)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEE

RNGGIGHKC,
and
                                           (SEQ ID NO: 113)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKEVER

RQGGIGHKC
``` or an amino acid sequence that differs from SEQ ID NO: 107, SEQ ID NO: 108, SEQ ID NO: 109, SEQ ID NO: 110, SEQ ID NO: 111, SEQ ID NO: 112 or SEQ ID NO: 113 in at most 10 amino acids or is at least 90% identical to any of these sequences.

In an embodiments, the present disclosure provides a Fab specific for GPVI as disclosed herein, comprising a modified heavy chain constant region, wherein said modified heavy chain constant region consist the amino acid sequence

```
                                           (SEQ ID NO: 113)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKEVER

RQGGIGHKC
```

In certain embodiments, the present disclosure provides a Fab specific for GPVI comprising a modified heavy chain constant region and a combination of a VH and a VL, selected from the group consisting of
 a) the VH of SEQ ID NO: 17 and the VL of SEQ ID NO: 18,
 b) the VH of SEQ ID NO: 28 and the VL of SEQ ID NO: 29,
 c) the VH of SEQ ID NO: 39 and the VL SEQ ID NO.40, and
 d) the VH of SEQ ID NO: 50 and the VL of SEQ ID NO: 51, and
wherein said modified heavy chain constant region consists of an amino acid sequence selected from the group consisting of SEQ ID NO: 107, SEQ ID NO: 108, SEQ ID NO 109, SEQ ID NO: 110, SEQ ID NO: 111, SEQ ID NO: 112 and SEQ ID NO: 113. In an embodiment, said modified heavy chain constant region consists of SEQ ID NO: 113.

In an embodiment, the present disclosure provides a Fab specific for GPVI, wherein said Fab comprises a combination of a VH and a VL, selected from the group consisting of
 a) the VH of SEQ ID NO: 17 and the VL of SEQ ID NO: 18,
 b) the VH of SEQ ID NO: 28 and the VL of SEQ ID NO: 29,
 c) the VH of SEQ ID NO: 39 and the VL of SEQ ID NO.40, and
 d) the VH of SEQ ID NO: 50 and the VL of SEQ ID NO: 51,
and further comprises a modified heavy chain constant region selected from the group consisting of SEQ ID NO: 107, SEQ ID NO: 108, SEQ ID NO 109, SEQ ID NO: 110, SEQ ID NO: 111, SEQ ID NO: 112 and SEQ ID NO: 113. In a preferred embodiment, said modified heavy chain constant region consists of SEQ ID NO. 113.

In one embodiment, the present disclosure refers to a Fab specific for GPVI comprising a modified heavy chain constant region, wherein said Fab comprises the heavy chain of SEQ ID NO: 21 and the light chain of SEQ ID NO: 19.

In one embodiment, the present disclosure refers to a Fab specific for GPVI comprising a modified heavy chain constant region, wherein said Fab comprises the heavy chain of SEQ ID NO: 32 and the light chain of SEQ ID NO: 30.

In one embodiment, the present disclosure refers to Fab specific for GPVI comprising a modified heavy chain constant region, wherein said Fab comprises the heavy chain of SEQ ID NO: 43 and the light chain of SEQ ID NO: 41.

In one embodiment, the present disclosure refers to a Fab specific for GPVI comprising a modified heavy chain constant region, wherein said Fab comprises the heavy chain of SEQ ID NO: 54 and the light chain of SEQ ID NO: 52.

In one embodiment, the present disclosure refers to a Fab specific for GPVI comprising a modified heavy chain constant region, wherein said Fab consists of the heavy chain of SEQ ID NO: 21 and the light chain of SEQ ID NO: 19.

In one embodiment, the present disclosure refers to a Fab specific for GPVI comprising a modified heavy chain constant region, wherein said Fab consists of the heavy chain of SEQ ID NO: 32 and the light chain of SEQ ID NO: 30.

In one embodiment, the present disclosure refers to Fab specific for GPVI comprising a modified heavy chain constant region, wherein said Fab consists of the heavy chain of SEQ ID NO: 43 and the light chain of SEQ ID NO: 41.

In one embodiment, the present disclosure refers to a Fab specific for GPVI comprising a modified heavy chain constant region, wherein said Fab consists of the heavy chain of SEQ ID NO: 54 and the light chain of SEQ ID NO: 52.

In a further embodiment, the present disclosure refers to a Fab specific for GPVI comprising a modified heavy chain constant region said Fab comprises
 a) the HC of SEQ ID NO: 20 and the LC of SEQ ID NO: 19, or b) the HC of SEQ ID NO: 21 and the LC of SEQ ID NO: 19, or
c) the HC of SEQ ID NO: 31 and the LC of SEQ ID NO: 30, or
d) the HC of SEQ ID NO: 32 and the LC of SEQ ID NO: 30, or
e) the HC of SEQ ID NO: 42 and the LC of SEQ ID NO: 41, or
f) the HC of SEQ ID NO: 43 and the LC of SEQ ID NO: 41, or
g) the HC of SEQ ID NO: 53 and the LC of SEQ ID NO: 52, or
h) the HC of SEQ ID NO: 54 and the LC of SEQ ID NO: 52.

In an embodiment, the present disclosure provides a Fab specific for GPVI according to the present disclosure, comprising a modified heavy chain constant region, wherein the modified heavy chain constant region comprises in order from the N-terminus to the C-terminus a CH1 domain and a polypeptide being able to constitute a non-auto-antigenic sequence, wherein said modified heavy chain constant region prevents or inhibits recognition of said Fab by anti-Fab antibodies present in a subject's serum and wherein and wherein said Fab consists of the heavy chain of SEQ ID NO: 43 and the light chain of SEQ ID NO: 41.

Accordingly, the present disclosure also provides a method of preventing platelet activation by anti-Fab antibodies present in a subject's serum when a Fab specific for GPVI is used, comprising:

(a) providing a Fab specific for GPVI comprising heavy chain constant region and a light chain constant region (b) adding or substituting a polypeptide being able to constitute a non-auto-antigenic to the C-terminus of the heavy chain constant region of said Fab.

Cross-Competition/Epitope

In embodiments, the disclosure pertains to an antibody or antibody fragment that cross-competes with an antibody or antibody fragment disclosed in Tables 1-4. In an embodiment, the present disclosure refers to an antibody or antibody fragment, wherein said antibody or antibody fragment cross-competes with an antibody or antibody fragment comprising 6 CDRs defined by Kabat of one of the antibodies disclosed in Table 1-4.

In another embodiment, the present disclosure refers to an antibody or antibody fragment, wherein said antibody or antibody fragment cross-competes with an antibody or antibody fragment comprising 6 CDRs, wherein the HCDR1 is the amino acid sequence of SEQ ID NO: 11, the HCDR2 is the amino acid sequence of SEQ ID NO: 12, the HCDR3 is the amino acid sequence of SEQ ID NO: 13, the LCDR1 is the amino acid sequence of SEQ ID NO: 14, the LCDR2 is the amino acid sequence of SEQ ID NO: 15 and the LCDR3 is the amino acid sequence of SEQ ID NO: 16. In another embodiment, the present disclosure refers to an antibody or antibody fragment, wherein said antibody or antibody fragment cross-competes with an antibody or antibody fragment comprising the VH according to SEQ ID NO: 17 and the VL according to SEQ ID NO: 18.

In another embodiment, the present disclosure refers to an antibody or antibody fragment, wherein said antibody or antibody fragment cross-competes with an antibody or antibody fragment comprising 6 CDRs, wherein the HCDR1 is the amino acid sequence of SEQ ID NO: 22, the HCDR2 is the amino acid sequence of SEQ ID NO: 23, the HCDR3 is the amino acid sequence of SEQ ID NO: 24, the LCDR1 is the amino acid sequence of SEQ ID NO: 25, the LCDR2 is the amino acid sequence of SEQ ID NO: 26 and the LCDR3 is the amino acid sequence of SEQ ID NO: 27. In another embodiment the present disclosure refers to an antibody or antibody fragment, wherein said antibody or antibody fragment cross-competes with an antibody or antibody fragment comprising the VH according to SEQ ID NO: 28 and the VL according to SEQ ID NO: 29.

In another embodiment, the present disclosure refers to an antibody or antibody fragment, wherein said antibody or antibody fragment cross-competes with an antibody or antibody fragment comprising 6 CDRs, wherein the HCDR1 is the amino acid sequence of SEQ ID NO: 34, the HCDR2 is the amino acid sequence of SEQ ID NO: 34, the HCDR3 is the amino acid sequence of SEQ ID NO: 35, the LCDR1 is the amino acid sequence of SEQ ID NO: 36, the LCDR2 is the amino acid sequence of SEQ ID NO: 37 and the LCDR3 is the amino acid sequence of SEQ ID NO: 38. In another embodiment the present disclosure refers to an antibody or antibody fragment, wherein said antibody or antibody fragment cross-competes with an antibody or antibody fragment comprising the VH according to SEQ ID NO: 39 and the VL according to SEQ ID NO: 40.

In another embodiment, the present disclosure refers to an antibody or antibody fragment, wherein said antibody or antibody fragment cross-competes with an antibody or antibody fragment comprising 6 CDRs, wherein the HCDR1 is the amino acid sequence of SEQ ID NO: 44, the HCDR2 is the amino acid sequence of SEQ ID NO: 45, the HCDR3 is the amino acid sequence of SEQ ID NO: 46, the LCDR1 is the amino acid sequence of SEQ ID NO: 47, the LCDR2 is the amino acid sequence of SEQ ID NO: 48 and the LCDR3 is the amino acid sequence of SEQ ID NO: 49. In another embodiment the present disclosure refers to an antibody or antibody fragment, wherein said antibody or antibody fragment cross-competes with an antibody or antibody fragment comprising the VH according to SEQ ID NO: 50 and the VL according to SEQ ID NO: 51.

In another embodiment, the present disclosure refers to an antibody or antibody fragment that cross-competes with an antibody or antibody fragment disclosed in Tables 1-4 and reduces the binding of any one of the antibodies disclosed in Tables 1-4 to GPVI by at least 60%, 70%, 80% or 90% in an ELISA-based cross-competition assay. In a certain embodiment, the antibody or antibody fragment that cross-competes with an antibody or antibody fragment disclosed in Tables 1-4 reduces the binding of one of the antibodies described in Tables 1-4 to GPVI by at least 60%, 70%, 80% or 90% in an ELISA-based cross-competition assay according to Example 17.

In another embodiment, the present disclosure refers to an antibody or antibody fragment that binds to (e.g., by binding, stabilizing, spatial distribution) the same epitope as one of the antibodies disclosed in Tables 1-4. In a further embodiment, said antibody or antibody fragment binds to (e.g., by binding, stabilizing, spatial distribution) the same epitope as an antibody or antibody fragment comprising 6 CDRs defined by Kabat of one of the antibodies disclosed in Tables 1-4. In yet another embodiment, said antibody or antibody fragment binds to (e.g., by binding, stabilizing, spatial distribution) the same epitope of GPVI as an antibody or antibody fragment comprising 6 CDRs defined by Kabat of one of the antibodies disclosed in Tables 1-4. In yet another embodiment, said antibody or antibody fragment binds to (e.g., by binding, stabilizing, spatial distribution) the same epitope of polypeptide comprising the amino acid sequence of SEQ ID NO: 1 as an antibody or antibody fragment comprising 6 CDRs defined by Kabat of one of the antibodies disclosed in Tables 1-4

In another embodiment, the present disclosure refers to an antibody or antibody fragment, wherein said antibody or antibody fragment binds to the same epitope as an antibody or antibody fragment comprising 6 CDRs, wherein the HCDR1 is the amino acid sequence of SEQ ID NO: 11, the HCDR2 is the amino acid sequence of SEQ ID NO: 12, the HCDR3 is the amino acid sequence of SEQ ID NO: 13, the LCDR1 is the amino acid sequence of SEQ ID NO: 14, the LCDR2 is the amino acid sequence of SEQ ID NO: 15 and the LCDR3 is the amino acid sequence of SEQ ID NO: 16. In another embodiment, the present disclosure refers to an antibody or antibody fragment, wherein said antibody or antibody fragment binds to the same epitope as an antibody or antibody fragment comprising the VH according to SEQ ID NO: 17 and the VL according to SEQ ID NO: 18.

In another embodiment, the present disclosure refers to an antibody or antibody fragment, wherein said antibody or antibody fragment binds to the same epitope as an antibody or antibody fragment comprising 6 CDRs, wherein the HCDR1 is the amino acid sequence of SEQ ID NO: 22, the HCDR2 is the amino acid sequence of SEQ ID NO: 23, the HCDR3 is the amino acid sequence of SEQ ID NO: 24, the LCDR1 is the amino acid sequence of SEQ ID NO: 25, the LCDR2 is the amino acid sequence of SEQ ID NO: 26 and the LCDR3 is the amino acid sequence of SEQ ID NO: 27. In another embodiment, the present disclosure refers to an antibody or antibody fragment, wherein said antibody or antibody fragment binds to the same epitope as an antibody or antibody fragment comprising the VH according to SEQ ID NO: 28 and the VL according to SEQ ID NO: 29.

In another embodiment, the present disclosure refers to an antibody or antibody fragment, wherein said antibody or antibody fragment binds to the same epitope as an antibody or antibody fragment comprising 6 CDRs, wherein the HCDR1 is the amino acid sequence of SEQ ID NO: 34, the HCDR2 is the amino acid sequence of SEQ ID NO: 34, the HCDR3 is the amino acid sequence of SEQ ID NO: 35, the LCDR1 is the amino acid sequence of SEQ ID NO: 36, the LCDR2 is the amino acid sequence of SEQ ID NO: 37 and the LCDR3 is the amino acid sequence of SEQ ID NO: 38. In another embodiment, the present disclosure refers to an antibody or antibody fragment, wherein said antibody or antibody fragment binds to the same epitope as an antibody or antibody fragment comprising the VH according to SEQ ID NO: 39 and the VL according to SEQ ID NO: 40.

In another embodiment, the present disclosure refers to an antibody or antibody fragment, wherein said antibody or antibody fragment binds to the same epitope as an antibody or antibody fragment comprising 6 CDRs, wherein the HCDR1 is the amino acid sequence of SEQ ID NO: 44, the HCDR2 is the amino acid sequence of SEQ ID NO: 45, the HCDR3 is the amino acid sequence of SEQ ID NO: 46, the LCDR1 is the amino acid sequence of SEQ ID NO: 47, the LCDR2 is the amino acid sequence of SEQ ID NO: 48 and the LCDR3 is the amino acid sequence of SEQ ID NO: 49. In another embodiment the present disclosure refers to an antibody or antibody fragment, wherein said antibody or antibody fragment binds to the same epitope as an antibody or antibody fragment comprising the VH according to SEQ ID NO: 50 and the VL according to SEQ ID NO: 51

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, epitopes are readily identified by determining spatial conformation of amino acids such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. MoI. Biol. 157:105-132; for hydropathy plots.

In a certain embodiment, the antibody or antibody fragment that binds to the same epitope on GPVI as the antibodies of the present disclosure is a human monoclonal antibody or antibody fragment. In a certain embodiment, the antibody or antibody fragment that binds to the same linear epitope on GPVI as the antibody or antibody fragment of the present disclosure is a human monoclonal antibody or antibody fragment. In a certain embodiment, the antibody or antibody fragment that binds to the same conformational epitope on GPVI as the antibodies of the present disclosure is a human monoclonal antibody or antibody fragment. Such human monoclonal antibodies or antibody fragments can be prepared and isolated as described herein.

Method of Treatment

The antibody or antibody fragment specific for GPVI according to the present disclosure may be used for the prophylaxis or treatment of thrombotic or vascular disorders or conditions associated with the undesired presence of GPVI.

In an embodiments, the present disclosure refers to an antibody or antibody fragments according to the present disclosure for use in medicine. In an embodiment, the present disclosure refers to antibody or antibody fragment according to the present disclosure for use in the treatment of a subject in need thereof. In an embodiment, the present disclosure refers to an antibody or antibody fragment according to the present disclosure for use in the preparation of a medicament. In embodiments, the methods disclosed herein comprise administering to a subject in need thereof an antibody or antibody fragment according to the present disclosure. The present disclosure also relates to the use of an antibody or antibody fragment specific for GPVI according to the present disclosure for use in the preparation of a medicament for the treatment and/or prophylaxis of a disorder or condition associated with the undesired presence of GPVI. In an embodiment, the present disclosure provides a method for the prophylaxis or treatment of a disorder or condition associated with the undesired presence of GPVI.

In certain embodiments, the present disclosure provides a method for the prophylaxis or treatment of a thrombotic or vascular disorder in a subject.

Thrombotic or vascular (e.g. cardiovascular) disorders or conditions related to GPVI may include, but are not limited to, such as, for example, arterial thrombosis including atherothrombosis, ischemic events, acute coronary artery syndrome, myocardial infarction (heart attack), acute cerebrovascular ischemia (stroke), percutaneous coronary intervention, stenting thrombosis, ischemic, restenosis, ischemia, (acute and chronic), disorders of the aorta and its branches (such as aortic aneurysm, thrombosis), peripheral artery disorders, venous thrombosis, acute phlebitis and pulmonary embolism, cancer-associated thrombosis (Trousseau syndrome), inflammatory thrombosis and thrombosis associated to infection. Further disorders or conditions associated with the undesired presence of GPVI may be but not limited to, bleeding disorders or conditions (such as, for example, bleeding tendency and/or prolonged bleeding time) such as thrombocytopenia such as, for example, idiopathic thrombocytopenic purpura (ITP) or immune thrombocytopenia. In yet another embodiment, a disorder or condition associated with the undesired presence of GPVI may comprise inflammation and/or cancer.

In an embodiment, the methods disclosed herein comprise the step of administering to the subject a therapeutically effective amount of an antibody or antibody fragment specific for GPVI according to the present disclosure. In an embodiment, said subject is a human. In an alternative embodiment, said subject is a rodent, such as a rat or a mouse. In an embodiment, the present disclosure refers to an antibody or antibody fragment specific for GPVI according to the present disclosure for use in the treatment of a disorder or condition associated with the undesired presence of GPVI.

The present disclosure further relates to a method for inhibiting GPVI receptor function and downstream signaling, thereby preventing or treating a disorder or condition associated with the undesired presence of GPVI, wherein said method comprises administering an antibody or antibody fragment according to the present disclosure to a subject.

The present disclosure refers to a method for inhibiting GPVI receptor function and downstream signaling while not impacting platelet count, presence of GPVI at the platelet surface or bleeding time.

The present disclosure further relates to a method for preventing or inhibiting the binding of GPVI to collagen, thereby treating or preventing a disorder or condition associated with the undesired presence of GPVI, wherein said method comprises administering an antibody or antibody fragment specific for GPVI according to the present disclosure to a subject. In one embodiment, the method for preventing or inhibiting the binding of GPVI to collagen does not impact platelet count, presence of GPVI at the platelet surface or bleeding time in a subject.

The present disclosure further relates to a method for inhibiting or preventing platelet adhesion to collagen, thereby treating a GPVI related condition, wherein said method comprises administering an antibody or antibody fragment according to the present disclosure to a subject. In one embodiment, the method for preventing or inhibiting adhesion of GPVI to collagen does not impact platelet count, presence of GPVI at the platelet surface or bleeding time in a subject.

In another embodiment, the antibody or antibody fragment according to the present disclosure is used to inhibit platelet aggregation. Thus, the present disclosure further relates to a method for inhibiting or preventing collagen-induced platelet aggregation, thereby treating a GPVI related condition, wherein said method comprises administering an antibody or antibody fragment according to the present disclosure to a subject. In one embodiment, the method for preventing or inhibiting collagen-induced platelet aggregation does not impact platelet count, presence of GPVI at the platelet surface or bleeding time in a subject.

The present disclosure further relates to a method for inhibiting or preventing platelet activation, thereby treating a GPVI related condition, wherein said method comprises administering an antibody or antibody fragment according to the present disclosure to a subject. In one embodiment, the method for preventing or inhibiting platelet activation does not impact platelet count, presence of GPVI at the platelet surface or bleeding time in a subject.

The present disclosure further relates to a method for preventing or inhibiting thrombus formation in a subject in response to collagen binding, wherein said method comprises administering an antibody or antibody fragment according to the present disclosure to a subject. In one embodiment, the method for preventing or inhibiting thrombus formation in response to collagen binding in a subject does not impact platelet count, presence of GPVI at the platelet surface or bleeding time in a subject.

In some embodiments, the methods disclosed herein comprise contacting platelets with an antibody or antibody fragment specific for GPVI according to the present disclosure.

In an embodiment, the subject is affected by, preferably is diagnosed with a disorder or condition related to GPVI, preferably a thrombotic or vascular disorder and/or event. In an embodiment, the subject is at risk of developing a disorder or condition related to GPVI, preferably a thrombotic or vascular disorder and/or event. Examples of risk include, but are not limited to, family history (such as, for example, genetic predisposition), ethnicity, age, tobacco exposure, high blood pressure (hypertension), high cholesterol, obesity, physical inactivity, diabetes (in particular type 2 diabetes), unhealthy diets, and harmful use of alcohol.

In an embodiment, said antibody or antibody fragment specific for GPVI administered in the disclosed methods herein comprises
  a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
  b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO:27, or
  c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
  d) the HCDR1 region of SEQ ID NO: 44, the HCDR2 region of SEQ ID NO: 45, the HCDR3 region of SEQ ID NO: 46, the LCDR1 region of SEQ ID NO.: 47, the LCDR2 region of SEQ ID NO: 48 and the LCDR3 region of SEQ ID NO: 49.

In a further embodiment, said antibody or antibody fragment comprises
  a) the VH of SEQ ID NO: 17 and the VL of SEQ ID NO: 18 or
  b) the VH of SEQ ID NO: 28 and the VL of SEQ ID NO: 29 or
  c) the VH of SEQ ID NO: 39 and the VL of SEQ ID NO: 40 or
  d) the VH of SEQ ID NO: 50 and the VL of SEQ ID NO: 51 or a VH and a VL that has at least 60%, at least 70%, at least 80%, at least 90% or at least 95% identity to the VH of SEQ ID NO: 17, 28, 39 or 50 and to the VL of SEQ ID NO: 18, 29, 40 or 51.

In a further embodiment, said antibody or antibody fragment comprises
- a) the HC of SEQ ID NO: 20 and the LC of SEQ ID NO: 19, or
- b) the HC of SEQ ID NO: 21 and the LC of SEQ ID NO: 19, or
- c) the HC of SEQ ID NO: 31 and the LC of SEQ ID NO: 30, or
- d) the HC of SEQ ID NO: 32 and the LC of SEQ ID NO: 30, or
- e) the HC of SEQ ID NO: 42 and the LC of SEQ ID NO: 41, or
- f) the HC of SEQ ID NO: 43 and the LC of SEQ ID NO: 41, or
- g) the HC of SEQ ID NO: 53 and the LC of SEQ ID NO: 52, or
- h) the HC of SEQ ID NO: 54 and the LC of SEQ ID NO: 52.

In an embodiment, said antibody or antibody fragment is a monoclonal antibody or antibody fragment. In an embodiment, said antibody or antibody fragment is an isolated antibody or antibody fragment. In an embodiment, said antibody or antibody fragment is an isolated monoclonal antibody or antibody fragment. In an embodiment, said antibody or antibody fragment is a monovalent antibody or antibody fragment. In one embodiment, said monovalent antibody or antibody fragment is selected from the group consisting of a scFv, an Fv, a Fab and a Fab'. In a preferred embodiment, said monovalent antibody or antibody fragment is a Fab.

Compositions

The compositions of the present disclosure are preferably pharmaceutical compositions comprising an antibody or antibody fragment specific for GPVI according to the present disclosure and a pharmaceutically acceptable carrier, diluent or excipient, for the prophylaxis or treatment of a thrombotic or vascular disorder. Such carriers, diluents and excipients are well known in the art, and the skilled artisan will find a formulation and a route of administration best suited to treat a subject with the GPVI antibody or antibody fragment of the present disclosure.

In an embodiment, the present disclosure refers to a pharmaceutical composition comprising an antibody or antibody fragment specific for GPVI according to the present disclosure and a pharmaceutically acceptable carrier or excipient.

Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

In an embodiment, said antibody or antibody fragment specific for GPVI is present in a pharmaceutically or therapeutically effective amount.

In an embodiment, the present disclosure refers to pharmaceutical compositions comprising an antibody or antibody fragment specific for GPVI according to the present disclosure for the use in the treatment of a disorder or condition associated with the undesired presence of GPVI. In another embodiment, said condition associated with the undesired presence of GPVI is a thrombotic or vascular disorder. In an embodiment, the present disclosure refers to the use of said pharmaceutical compositions comprising an antibody or antibody fragment specific for GPVI as disclosed herein in the preparation of a medicament for the treatment of a disorder or condition associated with the undesired presence of GPVI. In another embodiment, said disorder or condition associated with the undesired presence of GPVI is a thrombotic or vascular disorder. In an embodiment, the present disclosure refers to the use of said pharmaceutical composition for the treatment of a disorder or condition associated with the undesired presence of GPVI. In another embodiment, said disorder or condition associated with the undesired presence of GPVI is thrombotic or vascular disorder.

In another embodiment provided herein is a method of treating a thrombotic or vascular disorder in a subject, the method comprising administering a pharmaceutical composition comprising a therapeutically effective amount of an antibody or antibody fragment specific for GPVI according to the present disclosure. In another embodiment the subject is a subject in need thereof. In a preferred embodiment said subject is a human. In alternative embodiment said subject is a rodent, such as a rat or a mouse. In an embodiment, the present disclosure refers to a pharmaceutical composition comprising an antibody or antibody fragment specific for GPVI disclosed in Tables 1-4 and a pharmaceutically acceptable carrier or excipient. In an embodiment, said pharmaceutical composition is for the treatment or prophylaxis of a thrombotic or vascular disorder.

In another embodiment, the present disclosure refers to a method for the prophylaxis of a thrombotic or vascular disorder in a subject, said method comprising administering an antibody or antibody fragment of the present disclosure or a pharmaceutical composition comprising such antibody or antibody fragment and a pharmaceutically acceptable carrier or excipient, for the treatment of a thrombotic or vascular disorder.

"Prophylaxis" as used in this context refers to methods which aim to prevent the onset of a disorder or which delay the onset of a disorder. In some embodiments said subject is a human. In alternative embodiments said subject is a rodent, such as a rat or a mouse.

The term "administration" used herein includes subcutaneous, intravenous, intramuscular, intra-articular, intraspinally, intra-synovial, intrasternal, intrathecal, intrahepatic, intralesional and intracranial injection or infusion techniques.

In an embodiment, the compositions of the present disclosure comprising an antibody or antibody fragment specific for GPVI according to the present disclosure are administered intravenously. Preferably, a therapeutically effective amount of the antibody or antibody fragment of the present disclosure is administered to the subject in need thereof.

It will be understood that the total daily usage of the antibody or antibody fragment of the present disclosure, composition, pharmaceutical composition or medicament of the present disclosure will be decided by the attending physician within the scope of sound medical judgment. The specific therapeutically effective dose level for any particular patient will depend upon a variety of factors including the disorder being treated and the severity of the disorder; activity of the specific protein employed; the specific composition employed, the age, body weight, general health, sex and diet of the subject; the time of administration, route of administration, and rate of excretion of the specific protein employed; the duration of the treatment; drugs used in combination or coincidental with the specific protein employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the antibody or antibody fragment may be varied over a wide range from 0.01 to 500 mg per subject per day. Preferably, the compositions contain 1.0, 2.5, 5.0, 10.0, 15.0, 25.0, 50.0, 100, 150, 200, 250, 300, 350, 400, 450 or 500 mg of the active ingredient for the symptomatic adjustment of the dosage to the patient to be treated. A medication typically contains from 0.01 mg to 1000 mg of the active ingredient, preferably from 1 mg to 500 mg of the active ingredient.

In an embodiment, the present disclosure refers to the use of a composition comprising an antibody or antibody fragment specific for GPVI according to the present disclosure for the manufacture of pharmaceutical preparations for simultaneous, separate or sequential use in the treatment and/or prevention and/or prophylaxis and/or therapy of a disorder or condition related to undesired presence of GPVI or a GPVI related condition. In a preferred embodiment, the compositions of the present disclosure are preferably pharmaceutical compositions comprising a Fab specific for GPVI Methods of Identification In an embodiment, the present disclosure provides a method to identify an antagonistic antibody or antibody fragment specific GPVI comprising the steps of:
a) contacting platelet rich plasma of a mammal with an antibody or antibody fragment specific GPVI
b) initiating the aggregation of platelets by adding collagen
c) comparing the aggregation as determined in step (b) with the aggregation which is obtained when the collagen is added to platelet rich plasma without adding the antibody or antibody fragment specific for GPVI of step (a),
wherein a reduction of aggregation of platelets in the presence of the antibody or antibody fragment as described in step (a) indicates that said antibody or antibody fragment is an inhibitor or antagonist of GPVI according to the present disclosure.

In an embodiment, the reduction of aggregation of platelets is reduced by at least 30%, at least 40%, at least 50%, at least 60%, at least 70%, or at least 80%, or at least 90%, or at least 95% in the presence of the antibody or antibody fragment described in step (a).

Diagnostics

The present disclosure further relates to the use of the antibody or antibody fragment specific for human GPVI according to the present disclosure for detecting GPVI in a biological sample. Examples of assays in which the antibody or antibody fragment of the present disclosure may be used, include, but are not limited to, ELISA, sandwich ELISA, RIA, FRCS, tissue immunohistochemistry, Western-blot, and immunoprecipitation. In an embodiment, the antibody or antibody fragment of the present disclosure may be labeled for diagnostic or detection purposes. By labeled herein is meant that a compound has at least one element, isotope or chemical compound attached to enable the detection of the compound.

In an embodiment of the present disclosure, the antibody or antibody fragment specific for GPVI can be used for diagnosis of GPVI expression changes. It is described that changes in the expression of GPVI on the platelet surface as well as the occurrence and concentration of soluble GPVI (cleaved extracellular domain of GPVI) in plasma may well be associated with pathophysiological conditions such as acute coronary syndromes, transient ischemic attacks or stroke (Bigalke B, et al., Eur J Neurol., 2009 Jul. 21; Bigalke B. et al., Semin Thromb Hemost. 2007 March; 33(2): 179-84).

Thus, measurement of these parameters could be used to identify subjects at risk for the aforementioned conditions requiring anti-thrombotic treatment and being possibly particularly susceptible for anti-GPVI treatment. Therefore, antibodies and antibody fragments described herein can be used as a diagnostic tool and be part of a diagnostic kit which determines the presence and quantitative changes of GPVI on the platelet surface as well as in plasma samples.

Such method for diagnosing of GPVI changes in a subject may comprise
a) contacting platelets or plasma sample of said patient with an antibody or antibody fragment according to the present disclosure,
b) measuring the binding of said antibody or antibody fragment to the cells present in said sample, and
c) comparing the binding measured in step (ii) with that of a normal reference subject or standard.

Another object of the present disclosure is a kit comprising at least one antibody or antibody fragment of the disclosure. By "kit" is intended any manufacture (e.g., a package or a container) comprising at least one reagent, i.e. for example an antibody or antibody fragment, for specifically detecting the expression of GPVI. The kit may be promoted, distributed, or sold as a unit for performing the methods of the present invention. Furthermore, any or all of the kit reagents may be provided within containers that protect them from the external environment, such as in sealed containers. The kits may also contain a package insert describing the kit and methods for its use.

Antibody Sequences

TABLE 1

| Antibody sequences of Fab#1 | | | | |
|---|---|---|---|---|
| Antibody# | | | SEQ ID NO: | [aa]/DNA |
| Fab#1 | HCDR1 (Kabat) | (Protein) | 11 | SHYMH |
| | HCDR2 (Kabat) | (Protein) | 12 | LIEPSEGETEYAQRFQG |

TABLE 1-continued

| Antibody sequences of Fab#1 | | |
|---|---|---|
| Antibody# | SEQ ID NO: | [aa]/DNA |
| HCDR3 (Kabat) (Protein) | 13 | DSSRSYPLGFDI |
| LCDR1 (Kabat) (Protein) | 14 | SGSSSNIGNNYVS |
| LCDR2 (Kabat) (Protein) | 15 | DNNKRPS |
| LCDR3 (Kabat) (Protein) | 16 | AAWDFRSSRWV |
| VH (Protein) | 17 | QVQLVQSGAEVKKPGASVKVSCKASGYTFTSHYMHW VRQAPGQGLEWMGLIEPSEGETEYAQRFQGRVTMTRD TSTSTVYMELSSLRSEDTAVYYCARDSSRSYPLGFDIW GQGTLVTVSS |
| VL (Protein) | 18 | QSVLTQPPSVSAAPGQKVTISCSGSSSNIGNNYVSWYQ QLPGTAPKLLIYDNNKRPSGIPDRFSGSKSGTSATLGITG LQTEDEADYYCAAWDERSSRWVFGGGTKLTVLGQ |
| Light chain (Fab) (Protein) | 19 | QSVLTQPPSVSAAPGQKVTISCSGSSSNIGNNYVSWYQ QLPGTAPKLLIYDNNKRPSGIPDRFSGSKSGTSATLGITG LQTEDEADYYCAAWDFRSSRWVFGGGTKLTVLGQPK AAPSVTLFPPSSEELQANKATLVCLISDFYPGAVTVAW KADSSPVKAGVETTTPSKQSNNKYAASSYLSLTPEQWK SHRSYSCQVTHEGSTVEKTVAPTECS |
| Heavy chain (Fab) (Protein) | 20 | QVQLVQSGAEVKKPGASVKVSCKASGYTFTSHYMHW VRQAPGQGLEWMGLIEPSEGETEYAQRFQGRVTMTRD TSTSTVYMELSSLRSEDTAVYYCARDSSRSYPLGFDIW GQGTLVTVSSASTKGPSVFPLAPSSKSTSGGTAALGCL VKDYFPEPVTVSWNSGALTSGVHTFPAVLQSSGLYSLS SVVTVPSSSLGTQTYICNVNHKPSNTKVDKRVEPKSC |
| Heavy chain with modified heavy chain constant region (Fab) (Protein) | 21 | QVQLVQSGAEVKKPGASVKVSCKASGYTFTSHYMHW VRQAPGQGLEWMGLIEPSEGETEYAQRFQGRVTMTRD TSTSTVYMELSSLRSEDTAVYYCARDSSRSYPLGFDIW GQGTLVTVSSASTKGPSVFPLAPSSKSTSGGTAALGCL VKDYFPEPVTVSWNSGALTSGVHTFPAVLQSSGLYSLS SVVTVPSSSLGTQTYICNVNFIKPSNTKVDKEVERRQGG IGHKC |
| HCDR1 (Kabat) (DNA) | 55 | TCCCATTACATGCAT |
| HCDR2 (Kabat) (DNA) | 56 | CTGATCGAGCCCTCCGAGGGAGAGACTGAGTATGCT CAACGGTTCCAAGGC |
| HCDR3 (Kabat) (DNA) | 57 | GACAGCAGCCGTAGCTACCCTCTGGGTTTCGATATT |
| LCDR1 (Kabat) (DNA) | 58 | AGCGGCAGCAGCAGCAACATCGGCAACAACTACGTT AGC |
| LCDR2 (Kabat) (DNA) | 59 | GATAACAACAAACGCCCGAGC |
| LCDR3 (Kabat) (DNA) | 60 | GCTGCTTGGGACTTCCGTTCTTCTCGTTGGGTG |
| VH (DNA) | 61 | CAGGTGCAGCTGGTGCAGAGCGGTGCCGAAGTGAAA AAACCAGGCGCCAGCGTGAAAGTTAGCTGCAAAGCC AGCGGCTATACCTTTACCTCCCATTACATGCATTGGG TTCGCCAGGCCCCAGGCCAGGGTCTGGAATGGATGG GGCTGATCGAGCCCTCCGAGGGAGAGACTGAGTATG CTCAACGGTTCCAAGGCCGCGTGACCATGACCCGCG ATACCAGCACCAGCACCGTGTATATGGAACTGAGCA GCCTGCGCAGCGAAGATACCGCCGTGTATTATTGCG CGCGAGACAGCAGCCGTAGCTACCCTCTGGGTTTCG ATATTTGGGGCCAGGGCACCCTGGTTACTGTCTCGAG C |

TABLE 1-continued

Antibody sequences of Fab#1

| Antibody# | | SEQ ID NO: | [aa]/DNA |
|---|---|---|---|
| | VL (DNA) | 62 | CAGAGCGTGCTGACCCAGCCGCCGAGCGTTAGCGCC GCACCAGGCCAGAAAGTGACCATTAGCTGTAGCGGC AGCAGCAGCAACATCGGCAACAACTACGTTAGCTGG TATCAGCAGCTGCCGGGCACCGCCCCGAAACTGCTG ATCTATGATAACAACAAACGCCCGAGCGGCATCCCG GATCGCTTTAGCGGTAGCAAAAGCGGCACCAGCGCC ACCCTGGGCATTACCGGCCTGCAAACCGAAGACGAA GCCGATTATTACTGCGCTGCTTGGGACTTCCGTTCTT CTCGTTGGGTGTTTGGCGGCGGTACCAAGCTGACCGT GCTGGGCCAG |
| | Light chain (Fab) (DNA) | 63 | CAGAGCGTGCTGACCCAGCCGCCGAGCGTTAGCGCC GCACCAGGCCAGAAAGTGACCATTAGCTGTAGCGGC AGCAGCAGCAACATCGGCAACAACTACGTTAGCTGG TATCAGCAGCTGCCGGGCACCGCCCCGAAACTGCTG ATCTATGATAACAACAAACGCCCGAGCGGCATCCCG GATCGCTTTAGCGGTAGCAAAAGCGGCACCAGCGCC ACCCTGGGCATTACCGGCCTGCAAACCGAAGACGAA GCCGATTATTACTGCGCTGCTTGGGACTTCCGTTCTT CTCGTTGGGTGTTTGGCGGCGGTACCAAGCTGACCGT GCTGGGCCAGCCCAAAGCCGCCCCTAGCGTGACCCT GTTCCCCCCAAGCAGCGAGGAACTCCAGGCCAACAA GGCCACCCTCGTGTGCCTGATCAGCGACTTCTACCCT GGCGCCGTGACCGTGGCCTGGAAGGCCGATAGCAGC CCTGTGAAGGCCGGCGTGGAAACCACCACCCCCAGC AAGCAGAGCAACAACAAATACGCCGCCAGCAGCTAC CTGAGCCTGACCCCCGAGCAGTGGAAGTCCCACAGA TCCTACAGCTGCCAGGTCACACACGAGGGCAGCACC GTGGAAAAGACCGTGGCCCCCACCGAGTGCAGC |
| | Heavy chain (Fab) (DNA) | 64 | CAGGTGCAGCTGGTGCAGAGCGGTGCCGAAGTGAAA AAACCAGGCGCCAGCGTGAAAGTTAGCTGCAAAGCC AGCGGCTATACCTTTACCTCCCATTACATGCATTGGG TTCGCCAGGCCCCAGGCCAGGGTCTGGAATGGATGG GGCTGATCGAGCCCTCCGAGGGAGAGACTGAGTATG CTCAACGGTTCCAAGGCCGCGTGACCATGACCCGCG ATACCAGCACCAGCACCGTGTATATGGAACTGAGCA GCCTGCGCAGCGAAGATACCGCCGTGTATTATTGCG CGCGAGACAGCAGCCGTAGCTACCCTCTGGGTTTCG ATATTTGGGGCCAGGGCACCCTGGTTACTGTCTCGAG CGCCAGCACAAAGGGACCCAGCGTGTTCCCTCTGGC CCCCAGCAGCAAGTCTACATCTGGCGGAACAGCCGC CCTGGGCTGCCTCGTAAGGACTACTTTCCCGAGCCC GTGACCGTGTCCTGGAACTCTGGCGCTCTGACAAGC GGCGTGCACACCTTTCCAGCCGTGCTCCAGAGCAGC GGCCTGTACTCTCTGAGCAGCGTCGTGACAGTGCCC AGCAGCTCTCTGGGCACCCAGACCTACATCTGCAAC GTGAACCACAAGCCCAGCAACACAAAGGTGGACAA GCGGGTGGAACCCAAGTCCTGC |
| | Heavy chain (Fab) with modified heavy chain constant region (DNA) | 65 | CAGGTGCAGCTGGTGCAGAGCGGTGCCGAAGTGAAA AAACCAGGCGCCAGCGTGAAAGTTAGCTGCAAAGCC AGCGGCTATACCTTTACCTCCCATTACATGCATTGGG TTCGCCAGGCCCCAGGCCAGGGTCTGGAATGGATGG GGCTGATCGAGCCCTCCGAGGGAGAGACTGAGTATG CTCAACGGTTCCAAGGCCGCGTGACCATGACCCGCG ATACCAGCACCAGCACCGTGTATATGGAACTGAGCA GCCTGCGCAGCGAAGATACCGCCGTGTATTATTGCG CGCGAGACAGCAGCCGTAGCTACCCTCTGGGTTTCG ATATTTGGGGCCAGGGCACCCTGGTTACTGTCTCGAG CGCCAGCACAAAGGGACCCAGCGTGTTCCCTCTGGC CCCCAGCAGCAAGTCTACATCTGGCGGAACAGCCGC CCTGGGCTGCCTCGTAAGGACTACTTTCCCGAGCCC GTGACCGTGTCCTGGAACTCTGGCGCTCTGACAAGC GGCGTGCACACCTTTCCAGCCGTGCTCCAGAGCAGC GGCCTGTACTCTCTGAGCAGCGTCGTGACAGTGCCC AGCAGCTCTCTGGGCACCCAGACCTACATCTGCAAC GTGAACCACAAGCCCAGCAACACAAAGGTGGACAA GGAAGTCGAGCGCAGACAGGGCGGCATCGGCCATA AATGC |

TABLE 2

Antibody sequences of Fab#2

| Antibody# | | SEQ ID NO: | [aa]/DNA |
|---|---|---|---|
| Fab#2 | HCDR1 (Kabat) (Protein) | 22 | DHYMS |
| | HCDR2 (Kabat) (Protein) | 23 | SVGSEGKFIDYAASVKG |
| | HCDR3 (Kabat) (Protein) | 24 | HYREFRWHYYYFDY |
| | LCDR1 (Kabat) (Protein) | 25 | TGSSSNIGAGYDVH |
| | LCDR2 (Kabat) (Protein) | 26 | GNSNRPS |
| | LCDR3 (Kabat) (Protein) | 27 | QSHDLGAHVWV |
| | VH (Protein) | 28 | QVQLVESGGGLVKPGGSLRLSCAASGFSFSDHYMSWIRQ APGKGLEWVSSVGSEGKFIDYAASVKGRFTISRDNAKNS LYLQMNSLRAEDTAVYYCARHYREFRWHYYYFDYWG QGTLVTVSS |
| | VL (Protein) | 29 | QSVLTQPPSVSGAPGQRVTISCTGSSSNIGAGYDVHWYQ QLPGTAPKLLIYGNSNRPSGVPDRFSGSKSGTSASLAITG LQAEDEADYYCQSHDLGAHVWVFGGGTKLTVLGQ |
| | Light chain (Fab) (Protein) | 30 | QSVLTQPPSVSGAPGQRVTISCTGSSSNIGAGYDVHWYQ QLPGTAPKLLIYGNSNRPSGVPDRFSGSKSGTSASLAITG LQAEDEADYYCQSHDLGAHVWVFGGGTKLTVLGQPKA APSVTLFPPSSEELQANKATLVCLISDFYPGAVTVAWKA DSSPVKAGVETTTPSKQSNNKYAASSYLSLTPEQWKSHR SYSCQVTHEGSTVEKTVAPTECS |
| | Heavy chain (Fab) (Protein) | 31 | QVQLVESGGGLVKPGGSLRLSCAASGFSFSDHYMSWIRQ APGKGLEWVSSVGSEGKFIDYAASVKGRFTISRDNAKNS LYLQMNSLRAEDTAVYYCARHYREFRWHYYYFDYWG QGTLVTVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKRVEPKSC |
| | Heavy chain with modified heavy chain constant region (Fab) (Protein) | 32 | QVQLVESGGGLVKPGGSLRLSCAASGFSFSDHYMSWIRQ APGKGLEWVSSVGSEGKFIDYAASVKGRFTISRDNAKNS LYLQMNSLRAEDTAVYYCARHYREFRWHYYYFDYWG QGTLVTVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKEVERRQGGIGHK C |
| | HCDR1 (Kabat) (DNA) | 66 | GACCATTACATGAGC |
| | HCDR2 (Kabat) (DNA) | 67 | AGCGTTGGGAGCGAGGGCAAATTCATCGACTATGCTG CAAGCGTGAAAGGG |
| | HCDR3 (Kabat) (DNA) | 68 | CACTACCGTGAGTTCCGTTGGCACTACTATTACTTTGA CTAT |
| | LCDR1 (Kabat) (DNA) | 69 | ACCGGCAGCAGCAGCAACATTGGCGCAGGCTATGATG TGCAT |
| | LCDR2 (Kabat) (DNA) | 70 | GGCAACAGCAATCGCCCAAGC |
| | LCDR3 (Kabat) (DNA) | 71 | CAGTCTCATGACCTGGGTGCTCATGTTTGGGTG |
| | VH (DNA) | 72 | CAGGTGCAGCTGGTGGAAAGCGGCGGTGGCCTGGTGA AACCAGGCGGTAGCCTGCGCCTGAGCTGCGCCGCCAG CGGGTTTAGCTTTTCCGACCATTACATGAGCTGGATTC GCCAGGCCCCAGGCAAAGGCCTGGAATGGGTTAGCAG CGTTGGGAGCGAGGGCAAATTCATCGACTATGCTGCA AGCGTGAAAGGGCGCTTTACCATTAGCCGCGATAACG CCAAAAACAGCCTGTATCTGCAAATGAACAGCCTGCG GGCCGAAGATACCGCCGTGTATTATTGCGCGCGTCAC |

TABLE 2-continued

Antibody sequences of Fab#2

| Antibody# | | SEQ ID NO: | [aa]/DNA |
|---|---|---|---|
| | | | TACCGTGAGTTCCGTTGGCACTACTATTACTTTGACTATTGGGGTCAGGGCACCCTGGTTACTGTCTCGAGC |
| | VL (DNA) | 73 | CAGAGCGTGCTGACCCAGCCACCAAGCGTGAGCGGTGCACCAGGTCAGCGCGTGACCATTAGCTGCACCGGCAGCAGCAGCAACATTGGCGCAGGCTATGATGTGCATTGGTATCAGCAGCTGCCAGGCACCGCACCGAAACTGCTGATTTATGGCAACAGCAATCGCCCAAGCGGTGTGCCGGATCGCTTTAGCGGCAGCAAAAGCGGCACCAGCGCCAGCCTGGCGATTACCGGTCTGCAAGCCGAAGACGAAGCCGATTATTACTGCCAGTCTCATGACCTGGGTGCTCATGTTTGGGTGTTTGGCGGCGGTACCAAGCTGACCGTGCTGGGCCAG |
| | Light chain (Fab) (DNA) | 74 | CAGAGCGTGCTGACCCAGCCACCAAGCGTGAGCGGTGCACCAGGTCAGCGCGTGACCATTAGCTGCACCGGCAGCAGCAGCAACATTGGCGCAGGCTATGATGTGCATTGGTATCAGCAGCTGCCAGGCACCGCACCGAAACTGCTGATTTATGGCAACAGCAATCGCCCAAGCGGTGTGCCGGATCGCTTTAGCGGCAGCAAAAGCGGCACCAGCGCCAGCCTGGCGATTACCGGTCTGCAAGCCGAAGACGAAGCCGATTATTACTGCCAGTCTCATGACCTGGGTGCTCATGTTTGGGTGTTTGGCGGCGGTACCAAGCTGACCGTGCTGGGCCAGCCCAAAGCCGCCCCTAGCGTGACCCTGTTCCCCCCAAGCAGCGAGGAACTCCAGGCCAACAAGGCCACCCTCGTGTGCCTGATCAGCGACTTCTACCCTGGCGCCGTGACCGTGGCCTGGAAGGCCGATAGCAGCCCTGTGAAGGCCGGCGTGGAAACCACCACCCCCAGCAAGCAGAGCAACAACAAATACGCCGCCAGCAGCTACCTGAGCCTGACCCCCGAGCAGTGGAAGTCCCACAGATCCTACAGCTGCCAGGTCACACACGAGGGCAGCACCGTGGAAAAGACCGTGGCCCCCACCGAGTGCAGC |
| | Heavy chain (Fab) (DNA) | 75 | CAGGTGCAGCTGGTGGAAAGCGGCGGTGGCCTGGTGAAACCAGGCGGTAGCCTGCGCCTGAGCTGCGCCGCCAGCGGGTTTAGCTTTTCCGACCATTACATGAGCTGGATTCGCCAGGCCCCAGGCAAAGGCCTGGAATGGGTTAGCAGCGTTGGGAGCGAGGGCAAATTCATCGACTATGCTGCAAGCGTGAAAGGGCGCTTTACCATTAGCCGCGATAACGCCAAAAACAGCCTGTATCTGCAAATGAACAGCCTGCGGGGCCGAAGATACCGCCGTGTATTATTGCGCGCGTCACTACCGTGAGTTCCGTTGGCACTACTATTACTTTGACTATTGGGGTCAGGGCACCCTGGTTACTGTCTCGAGCGCCAGCACAAAGGGACCCAGCGTGTTCCCTCTGGCCCCCAGCAGCAAGTCTACATCTGGCGGAACAGCCGCCCTGGGCTGCCTCGTGAAGGACTACTTTCCCGAGCCCGTGACCGTGTCCTGGAACTCTGGCGCTCTGACAAGCGGCGTGCACACCTTTCCAGCCGTGCTCCAGAGCAGCGGCCTGTACTCTCTGAGCAGCGTCGTGACAGTGCCCAGCAGCTCTCTGGGCACCCAGACCTACATCTGCAACGTGAACCACAAGCCCAGCAACACAAAGGTGGACAAGCGGGTGGAACCCAAGTCCTGC |
| | Heavy chain with modified heavy chain constant region (Fab) (DNA) | 76 | CAGGTGCAGCTGGTGGAAAGCGGCGGTGGCCTGGTGAAACCAGGCGGTAGCCTGCGCCTGAGCTGCGCCGCCAGCGGGTTTAGCTTTTCCGACCATTACATGAGCTGGATTCGCCAGGCCCCAGGCAAAGGCCTGGAATGGGTTAGCAGCGTTGGGAGCGAGGGCAAATTCATCGACTATGCTGCAAGCGTGAAAGGGCGCTTTACCATTAGCCGCGATAACGCCAAAAACAGCCTGTATCTGCAAATGAACAGCCTGCGGGGCCGAAGATACCGCCGTGTATTATTGCGCGCGTCACTACCGTGAGTTCCGTTGGCACTACTATTACTTTGACTATTGGGGTCAGGGCACCCTGGTTACTGTCTCGAGCGCCAGCACAAAGGGACCCAGCGTGTTCCCTCTGGCCCCCAGCAGCAAGTCTACATCTGGCGGAACAGCCGCCCTGGGCTGCCTCGTGAAGGACTACTTTCCCGAGCCCGTGACCGTGTCCTGGAACTCTGGCGCTCTGACAAGCGGCGTGCACACCTTTCCAGCCGTGCTCCAGAGCAGCGGCCTGTACTCTCTGAGCAGCGTCGTGACAGTGCCCAGCAGCTCTCTGGGCACCCAGACCTACATCTGCAACGTGAACCACAAGCCCAGCAACACAAAGGTGGACAAGGAAGTCGAGCGCAGACAGGGCGGCATCGGCCATAAATGC |

TABLE 3

Antibody sequences of Fab#3

| Antibody# | | SEQ ID NO: | [aa]/DNA |
|---|---|---|---|
| Fab#3 | HCDR1 (Kabat) (Protein) | 33 | DYYVS |
| | HCDR2 (Kabat) (Protein) | 34 | AIGGSGSAVQYAESVKG |
| | HCDR3 (Kabat) (Protein) | 35 | HYREFRWHYYYFDY |
| | LCDR1 (Kabat) (Protein) | 36 | TGSSSNIGAGYDVH |
| | LCDR2 (Kabat) (Protein) | 37 | GNSNRPS |
| | LCDR3 (Kabat) (Protein) | 38 | QSHDLGAHVWV |
| | VH (Protein) | 39 | QVQLVESGGGLVKPGGSLRLSCAASGFSFGDY YVSWIRQAPGKGLEWVSAIGGSGSAVQYAESV KGRFTISRDNAKNSLYLQMNSLRAEDTAVYYC ARHYREFRWHYYYFDYWGQGTLVTVSS |
| | VL (Protein) | 40 | QSVLTQPPSVSGAPGQRVTISCTGSSSNIGAGYD VHWYQQLPGTAPKLLIYGNSNRPSGVPDRFSG SKSGTSASLAITGLQAEDEADYYCQSHDLGAH VWVFGGGTKLTVLGQ |
| | Light chain (Fab) (Protein) | 41 | QSVLTQPPSVSGAPGQRVTISCTGSSSNIGAGYD VHWYQQLPGTAPKLLIYGNSNRPSGVPDRFSG SKSGTSASLAITGLQAEDEADYYCQSHDLGAH VWVFGGGTKLTVLGQPKAAPSVTLFPPSSEELQ ANKATLVCLISDFYPGAVTVAWKADSSPVKAG VETTTPSKQSNNKYAASSYLSLTPEQWKSHRS YSCQVTHEGSTVEKTVAPTECS |
| | Heavy chain (Fab) (Protein) | 42 | QVQLVESGGGLVKPGGSLRLSCAASGFSFGDY YVSWIRQAPGKGLEWVSAIGGSGSAVQYAESV KGRFTISRDNAKNSLYLQMNSLRAEDTAVYYC ARHYREFRWHYYYFDYWGQGTLVTVSSASTK GPSVFPLAPSSKSTSGGTAALGCLVKDYFPEPV TVSWNSGALTSGVHTFPAVLQSSGLYSLSSVVT VPSSSLGTQTYICNVNTIKPSNTKVDKRVEPKSC |
| | Heavy chain with modified heavy chain constant region (Fab) (Protein) | 43 | QVQLVESGGGLVKPGGSLRLSCAASGFSFGDY YVSWIRQAPGKGLEWVSAIGGSGSAVQYAESV KGRFTISRDNAKNSLYLQMNSLRAEDTAVYYC ARHYREFRWHYYYFDYWGQGTLVTVSSASTK GPSVFPLAPSSKSTSGGTAALGCLVKDYFPEPV TVSWNSGALTSGVHTFPAVLQSSGLYSLSSVVT VPSSSLGTQTYICNVNHKPSNTKVDKEVERRQ GGIGHKC |
| | HCDR1 (Kabat) (DNA) | 77 | GACTATTACGTGAGC |
| | HCDR2 (Kabat) (DNA) | 78 | GCCATTGGGGGTCCGGTTCCGCCGTGCAAT ACGCTGAATCCGTGAAGGGC |
| | HCDR3 (Kabat) (DNA) | 79 | CACTACCGTGAGTTCCGTTGGCACTACTATTA CTTTGACTAT |
| | LCDR1 (Kabat) (DNA) | 80 | ACCGGCAGCAGCAGCAACATTGGCGCAGGCT ATGATGTGCAT |
| | LCDR2 (Kabat) (DNA) | 81 | GGCAACAGCAATCGCCCAAGC |
| | LCDR3 (Kabat) (DNA) | 82 | CAGTCTCATGACCTGGGTGCTCATGTTTGGGT G |
| | VH (DNA) | 83 | CAGGTGCAGCTGGTGGAAAGCGGCGGTGGCC TGGTGAAACCAGGCGGTAGCCTGCGCCTGAG CTGCGCCGCCAGCGGGTTTAGCTTCGGCGAC TATTACGTGAGCTGGATTCGCCAGGCCCCAG GCAAAGGCCTGGAATGGGTTAGCGCCATTGG GGGGTCCGGTTCCGCCGTGCAATACGCTGAA TCCGTGAAGGGCCGCTTTACCATTAGCCGCG ATAACGCCAAAAACAGCCTGTATCTGCAAAT GAACAGCCTGCGGGCCGAAGATACCGCCGTG TATTATTGCGCGCGTCACTACCGTGAGTTCCG TTGGCACTACTATTACTTTGACTATTGGGGTC AGGGCACCCTGGTTACTGTCTCGAGC |

TABLE 3-continued

Antibody sequences of Fab#3

| Antibody# | | SEQ ID NO: | [aa]/DNA |
|---|---|---|---|
| | VL (DNA) | 84 | CAGAGCGTGCTGACCCAGCCACCAAGCGTGA GCGGTGCACCAGGTCAGCGCGTGACCATTAG CTGCACCGGCAGCAGCAGCAACATTGGCGCA GGCTATGATGTGCATTGGTATCAGCAGCTGC CAGGCACCGCACCGAAACTGCTGATTTATGG CAACAGCAATCGCCCAAGCGGTGTGCCGGAT CGCTTTAGCGGCAGCAAAAGCGGCACCAGCG CCAGCCTGGCGATTACCGGTCTGCAAGCCGA AGACGAAGCCGATTATTACTGCCAGTCTCAT GACCTGGGTGCTCATGTTTGGGTGTTTGGCG GCGGTACCAAGCTGACCGTGCTGGGCCAG |
| | Light chain (Fab) (DNA) | 85 | CAGAGCGTGCTGACCCAGCCACCAAGCGTGA GCGGTGCACCAGGTCAGCGCGTGACCATTAG CTGCACCGGCAGCAGCAGCAACATTGGCGCA GGCTATGATGTGCATTGGTATCAGCAGCTGC CAGGCACCGCACCGAAACTGCTGATTTATGG CAACAGCAATCGCCCAAGCGGTGTGCCGGAT CGCTTTAGCGGCAGCAAAAGCGGCACCAGCG CCAGCCTGGCGATTACCGGTCTGCAAGCCGA AGACGAAGCCGATTATTACTGCCAGTCTCAT GACCTGGGTGCTCATGTTTGGGTGTTTGGCG GCGGTACCAAGCTGACCGTGCTGGGCCAGCC CAAAGCCGCCCCTAGCGTGACCCTGTTCCCC CCAAGCAGCGAGGAACTCCAGGCCAACAAG GCCACCCTCGTGTGCCTGATCAGCGACTTCTA CCCTGGCGCCGTGACCGTGGCCTGGAAGGCC GATAGCAGCCCTGTGAAGGCCGGCGTGGAAA CCACCACCCCAGCAAGCAGAGCAACAACA AATACGCCGCCAGCAGCTACCTGAGCCTGAC CCCCGAGCAGTGGAAGTCCCACAGATCCTAC AGCTGCCAGGTCACACACGAGGGCAGCACCG TGGAAAAGACCGTGGCCCCCACCGAGTGCAG C |
| | Heavy chain (Fab) (DNA) | 86 | CAGGTGCAGCTGGTGGAAAGCGGCGGTGGCC TGGTGAAACCAGGCGGTAGCCTGCGCCTGAG CTGCGCCGCCAGCGGGTTTAGCTTCGGCGAC TATTACGTGAGCTGGATTCGCCAGGCCCCAG GCAAAGGCCTGGAATGGGTTAGCGCCATTGG GGGGTCCGGTTCCGCCGTGCAATACGCTGAA TCCGTGAAGGGCCGCTTTACCATTAGCCGCG ATAACGCCAAAAACAGCCTGTATCTGCAAAT GAACAGCCTGCGGGCCGAAGATACCGCCGTG TATTATTGCGCGCGTCACTACCGTGAGTTCCG TTGGCACTACTATTACTTTGACTATTGGGGTC AGGGCACCCTGGTTACTGTCTCGAGCGCCAG CACAAAGGGACCCAGCGTGTTCCCTCTGGCC CCCAGCAGCAAGTCTACATCTGGCGGAACAG CCGCCCTGGGCTGCCTCGTGAAGGACTACTT TCCCGAGCCCGTGACCGTGTCCTGGAACTCT GGCGCTCTGACAAGCGGCGTGCACACCTTTC CAGCCGTGCTCCAGAGCAGCGGCCTGTACTC TCTGAGCAGCGTCGTGACAGTGCCCAGCAGC TCTCTGGGCACCCAGACCTACATCTGCAACG TGAACCACAAGCCCAGCAACACAAAGGTGG ACAAGCGGGTGGAACCCAAGTCCTGC |
| | Heavy chain with modified heavy chain constant region (Fab) (DNA) | 87 | CAGGTGCAGCTGGTGGAAAGCGGCGGTGGCC TGGTGAAACCAGGCGGTAGCCTGCGCCTGAG CTGCGCCGCCAGCGGGTTTAGCTTCGGCGAC TATTACGTGAGCTGGATTCGCCAGGCCCCAG GCAAAGGCCTGGAATGGGTTAGCGCCATTGG GGGGTCCGGTTCCGCCGTGCAATACGCTGAA TCCGTGAAGGGCCGCTTTACCATTAGCCGCG ATAACGCCAAAAACAGCCTGTATCTGCAAAT GAACAGCCTGCGGGCCGAAGATACCGCCGTG TATTATTGCGCGCGTCACTACCGTGAGTTCCG TTGGCACTACTATTACTTTGACTATTGGGGTC AGGGCACCCTGGTTACTGTCTCGAGCGCCAG CACAAAGGGACCCAGCGTGTTCCCTCTGGCC CCCAGCAGCAAGTCTACATCTGGCGGAACAG CCGCCCTGGGCTGCCTCGTGAAGGACTACTT TCCCGAGCCCGTGACCGTGTCCTGGAACTCT |

TABLE 3-continued

| Antibody sequences of Fab#3 | | | |
|---|---|---|---|
| Antibody# | | SEQ ID NO: | [aa]/DNA |
| | | | GGCGCTCTGACAAGCGGCGTGCACACCTTTC CAGCCGTGCTCCAGAGCAGCGGCCTGTACTC TCTGAGCAGCGTCGTGACAGTGCCCAGCAGC TCTCTGGGCACCCAGACCTACATCTGCAACG TGAACCACAAGCCCAGCAACACAAAGGTGG ACAAGGAAGTCGAGCGCAGACAGGGCGGCA TCGGCCATAAATGC |

TABLE 4

| Antibody sequences of Fab#4 | | | |
|---|---|---|---|
| Antibody# | | SEQ ID NO: | [aa]/DNA |
| Fab#4 | HCDR1 (Kabat) (Protein) | 44 | SSYMH |
| | HCDR2 (Kabat) (Protein) | 45 | IIEPTGASTLYAQRFQG |
| | HCDR3 (Kabat) (Protein) | 46 | TGIALPLGFDL |
| | LCDR1 (Kabat) (Protein) | 47 | SGSSSNIGNNYVS |
| | LCDR2 (Kabat) (Protein) | 48 | DNNKRPS |
| | LCDR3 (Kabat) (Protein) | 49 | AAWSTRFRWV |
| | VH (Protein) | 50 | QVQLVQSGAEVKKPGASVKVSCKASG GAFTSSYMHWVRQAPGQGLEWMGIIE PTGASTLYAQRFQGRVTMTRDTSTSTV YMELSSLRSEDTAVYYCARTGIALPLG FDLWGQGTLVTVSS |
| | VL (Protein) | 51 | QSVLTQPPSVSAAPGQKVTISCSGSSSNI GNNYVSWYQQLPGTAPKLLIYDNNKR PSGIPDRFSGSKSGTSATLGITGLQTEDE ADYYCAAWSTRFRWVFGGGTKLTVLG Q |
| | Light chain (Fab) (Protein) | 52 | QSVLTQPPSVSAAPGQKVTISCSGSSSNI GNNYVSWYQQLPGTAPKLLIYDNNKR PSGIPDRFSGSKSGTSATLGITGLQTEDE ADYYCAAWSTRFRWVFGGGTKLTVLG QPKAAPSVTLFPPSSEELQANKATLVCL ISDFYPGAVTVAWKADSSPVKAGVETT TPSKQSNNKYAASSYLSLTPEQWKSHR SYSCQVTHEGSTVEKTVAPTECS |
| | Heavy chain (Fab) (Protein) | 53 | QVQLVQSGAEVKKPGASVKVSCKASG GAFTSSYMHWVRQAPGQGLEWMGIIE PTGASTLYAQRFQGRVTMTRDTSTSTV YMELSSLRSEDTAVYYCARTGIALPLG FDLWGQGTLVTVSSASTKGPSVFPLAP SSKSTSGGTAALGCLVKDYFPEPVTVS WNSGALTSGVHTFPAVLQSSGLYSLSS VVTVPSSSLGTQTYICNVNHKPSNTKV DKRVEPKSC |
| | Heavy chain with modified heavy chain constant region (Protein) | 54 | QVQLVQSGAEVKKPGASVKVSCKASG GAFTSSYMHWVRQAPGQGLEWMGIIE PTGASTLYAQRFQGRVTMTRDTSTSTV YMELSSLRSEDTAVYYCARTGIALPLG FDLWGQGTLVTVSSASTKGPSVFPLAP SSKSTSGGTAALGCLVKDYFPEPVTVS WNSGALTSGVHTFPAVLQSSGLYSLSS VVTVPSSSLGTQTYICNVNHKPSNTKV DKEVERRQGGIGHKC |
| | HCDR1 (Kabat) (DNA) | 88 | TCCAGCTACATGCAT |
| | HCDR2 (Kabat) (DNA) | 89 | ATTATCGAGCCCACTGGGGCATCCAC ACTGTACGCACAGCGGTTCCAAGGG |

TABLE 4-continued

Antibody sequences of Fab#4

| Antibody# | | SEQ ID NO: [aa]/DNA | |
|---|---|---|---|
| | HCDR3 (Kabat) (DNA) | 90 | ACTGGAATCGCACTGCCTCTGGGTTT TGACCTG |
| | LCDR1 (Kabat) (DNA) | 91 | AGCGGCAGCAGCAGCAACATCGGCA ACAACTACGTTAGC |
| | LCDR2 (Kabat) (DNA) | 92 | GATAACAACAAACGCCCGAGC |
| | LCDR3 (Kabat) (DNA) | 93 | GCCGCTTGGAGTACTCGTTTCCGTTG GGTG |
| | VH (DNA) | 94 | CAGGTGCAGCTGGTGCAGAGCGGTGC CGAAGTGAAAAAACCAGGCGCCAGC GTGAAAGTTAGCTGCAAAGCCAGCG GCGGCGCATTTACCTCCAGCTACATG CATTGGGTTCGCCAGGCCCCAGGCCA GGGTCTGGAATGGATGGGCATTATCG AGCCCACTGGGGCATCCACACTGTAC GCACAGCGGTTCCAAGGGCGCGTGAC CATGACCCGCGATACCAGCACCAGCA CCGTGTATATGGAACTGAGCAGCCTG CGCAGCGAAGATACCGCCGTGTATTA TTGCGCGCGAACTGGAATCGCACTGC CTCTGGGTTTTGACCTGTGGGGCCAG GGCACCCTGGTTACTGTCTCGAGC |
| | VL (DNA) | 95 | CAGAGCGTGCTGACCCAGCCGCCGAG CGTTAGCGCCGCACCAGGCCAGAAA GTGACCATTAGCTGTAGCGGCAGCAG CAGCAACATCGGCAACAACTACGTTA GCTGGTATCAGCAGCTGCCGGGCACC GCCCCGAAACTGCTGATCTATGATAA CAACAAACGCCCGAGCGGCATCCCG GATCGCTTTAGCGGTAGCAAAAGCGG CACCAGCGCCACCCTGGGCATTACCG GCCTGCAAACCGAAGACGAAGCCGA TTATTACTGTGCCGCTTGGAGTACTC GTTTCCGTTGGGTGTTTGGCGGCGGT ACCAAGCTGACCGTGCTGGGCCAG |
| | Light chain (Fab) (DNA) | 96 | CAGAGCGTGCTGACCCAGCCGCCGAG CGTTAGCGCCGCACCAGGCCAGAAA GTGACCATTAGCTGTAGCGGCAGCAG CAGCAACATCGGCAACAACTACGTTA GCTGGTATCAGCAGCTGCCGGGCACC GCCCCGAAACTGCTGATCTATGATAA CAACAAACGCCCGAGCGGCATCCCG GATCGCTTTAGCGGTAGCAAAAGCGG CACCAGCGCCACCCTGGGCATTACCG GCCTGCAAACCGAAGACGAAGCCGA TTATTACTGTGCCGCTTGGAGTACTC GTTTCCGTTGGGTGTTTGGCGGCGGT ACCAAGCTGACCGTGCTGGGCCAGCC CAAAGCCGCCCCTAGCGTGACCCTGT TCCCCCAAGCAGCGAGGAACTCCAG GCCAACAAGGCCACCCTCGTGTGCCT GATCAGCGACTTCTACCCTGGCGCCG TGACCGTGGCCTGGAAGGCCGATAGC AGCCCTGTGAAGGCCGGCGTGGAAA CCACCACCCCCAGCAAGCAGAGCAA CAACAAATACGCCGCCAGCAGCTACC TGAGCCTGACCCCCGAGCAGTGGAAG TCCCACAGATCCTACAGCTGCCAGGT CACACACGAGGGCAGCACCGTGGAA AAGACCGTGGCCCCCACCGAGTGCAG C |
| | Heavy chain (Fab) (DNA) | 97 | CAGGTGCAGCTGGTGCAGAGCGGTGC CGAAGTGAAAAAACCAGGCGCCAGC GTGAAAGTTAGCTGCAAAGCCAGCG GCGGCGCATTTACCTCCAGCTACATG CATTGGGTTCGCCAGGCCCCAGGCCA GGGTCTGGAATGGATGGGCATTATCG AGCCCACTGGGGCATCCACACTGTAC GCACAGCGGTTCCAAGGGCGCGTGAC CATGACCCGCGATACCAGCACCAGCA |

TABLE 4-continued

Antibody sequences of Fab#4

| Antibody# | | SEQ ID NO: [aa]/DNA | |
|---|---|---|---|
| | | | CCGTGTATATGGAACTGAGCAGCCTG<br>CGCAGCGAAGATACCGCCGTGTATTA<br>TTGCGCGCGAACTGGAATCGCACTGC<br>CTCTGGGTTTTGACCTGTGGGGCCAG<br>GGCACCCTGGTTACTGTCTCGAGCGC<br>CAGCACAAAGGGACCCAGCGTGTTCC<br>CTCTGGCCCCCAGCAGCAAGTCTACA<br>TCTGGCGGAACAGCCGCCCTGGGCTG<br>CCTCGTGAAGGACTACTTTCCCGAGC<br>CCGTGACCGTGTCCTGGAACTCTGGC<br>GCTCTGACAAGCGGCGTGCACACCTT<br>TCCAGCCGTGCTCCAGAGCAGCGGCC<br>TGTACTCTCTGAGCAGCGTCGTGACA<br>GTGCCCAGCAGCTCTCTGGGCACCCA<br>GACCTACATCTGCAACGTGAACCACA<br>AGCCCAGCAACACAAAGGTGGACAA<br>GCGGGTGGAACCCAAGTCCTGC |
| | Heavy chain with modified heavy chain constant region (Fab) (DNA) | 98 | CAGGTGCAGCTGGTGCAGAGCGGTGC<br>CGAAGTGAAAAAACCAGGCGCCAGC<br>GTGAAAGTTAGCTGCAAAGCCAGCG<br>GCGGCGCATTTACCTCCAGCTACATG<br>CATTGGGTTCGCCAGGCCCCAGGCCA<br>GGGTCTGGAATGGATGGGCATTATCG<br>AGCCCACTGGGGCATCCACACTGTAC<br>GCACAGCGGTTCCAAGGGCGCGTGAC<br>CATGACCCGCGATACCAGCACCAGCA<br>CCGTGTATATGGAACTGAGCAGCCTG<br>CGCAGCGAAGATACCGCCGTGTATTA<br>TTGCGCGCGAACTGGAATCGCACTGC<br>CTCTGGGTTTTGACCTGTGGGGCCAG<br>GGCACCCTGGTTACTGTCTCGAGCGC<br>CAGCACAAAGGGACCCAGCGTGTTCC<br>CTCTGGCCCCCAGCAGCAAGTCTACA<br>TCTGGCGGAACAGCCGCCCTGGGCTG<br>CCTCGTGAAGGACTACTTTCCCGAGC<br>CCGTGACCGTGTCCTGGAACTCTGGC<br>GCTCTGACAAGCGGCGTGCACACCTT<br>TCCAGCCGTGCTCCAGAGCAGCGGCC<br>TGTACTCTCTGAGCAGCGTCGTGACA<br>GTGCCCAGCAGCTCTCTGGGCACCCA<br>GACCTACATCTGCAACGTGAACCACA<br>AGCCCAGCAACACAAAGGTGGACAA<br>GGAAGTCGAGCGCAGACAGGGCGGC<br>ATCGGCCATAAATGC |

TABLE 13

Antibody sequences of RefFab#1 derived from WO2011073954

| Antibody# | | SEQ ID NO: [aa] | |
|---|---|---|---|
| RefFab#1 | VH (Protein) | 99 | EVQLLESGPGLVAPSGSLSITCTVS GFSLTGYGVNWVRQPPGKGLEWLGM IWGDGSTDYQSTLKSRLSISKDNSK SQVFLKMNSLRTDDTARYYCARDLP MDYWGLGTSVTVSS |
| | VL (Protein) | 100 | DIQMTQSPSSLSASVGGRVTITCKA SQDINKYIAWYQHKPGKGPSLLIHY TSTLQPGVPSRFSGSGSGRDYSFSI SNLQPEDIATYYCLQYANLLTFGGG TKLEIKRT |

WORKING EXAMPLES

Example 1: Antigen Generation and Quality Control

Amino acid sequences of GPVI from human, cynomolgus monkey, mouse and rat were retrieved from public available sources (e.g. Uniprot) and were produced in-house.
Recombinant Soluble Extracellular Domains Soluble GPVI corresponds to the extracellular domain of GPVI fused at its C-terminus to a human Fc sequence. This soluble GPVI may be referred to as GPVI-Fc.

The extracellular domain (ECD) of human GPVI-1A (SEQ ID NO: 4), human GPVI-1B (SEQ ID NO: 5), human GPVI-2A; SEQ ID NO: 6), cynomolgus monkey GPVI (SEQ ID NO: 7), mouse GPVI (SEQ ID NO: 8) and rat GPVI (SEQ ID NO: 9) were cloned in the expression vector pMAX_vk_Fc2(K105-K330) using KpnI and EcoRV resulting in C-terminal Fc2(K105-K330) fusion constructs. Fc2 (K105-K330) has the amino acid sequence as disclosed in SEQ ID NO: 10.

The encoding DNA of the extracellular domain of human, cynomolgus monkey, mouse or rat GPVI were cloned in frame with an N-terminal Vic leader sequence and a C-terminal human IgG Fc-tag into a pMAX expression vector, which is a modified expression vector based on pcDNA3.1 (Thermo Fisher). HKB11 #52 (Parental clone: U.S. Pat. No. 6,136,599. J. Biomed. Sci. 2002; 9:631-638) cells were maintained in MAC1.0 medium containing 2.0 mM L-Alanyl-L-Glutamine, 0.1% PF-68 in a humidified CO2 incubator at 37° C. and 6% CO2. HKB11 #52 cells were transiently transfected one day post seeding with FectoPro™ and FectoPro™ Booster (Polyplus) according to the manufacturer's instructions. The cells were cultured for 3 days and the conditioned cell culture supernatant was harvested by centrifugation followed by sterile filtration. The antigens were purified by Protein A chromatography using HiTrap MabSelect SuRe columns (GE Healthcare). After binding and washing the proteins were eluted with 100 mM Glycin pH 3.0. All affinity chromatography steps were performed using ÄKTA Express (GE Healthcare) chromatography systems. The samples were subsequently neutralized (with 3 M Tris pH 8) and buffer-exchanged to PBS using PD10 columns (GE Healthcare). The quality of the samples was analyzed by denaturing, reducing or non-reducing SDS-PAGE, HP-SEC and DLS.

Recombinant Cells Overexpressing GPVI

CHO cells were stably transfected with either human GPVI (SEQ ID NO: 1), cynomolgus monkey GPVI (SEQ ID NO: 2) or mouse GPVI (SEQ ID NO: 3).

Flp-In CHO cells (Invitrogen) were stably transfected with pcDNA5/FRT/TO vectors encoding the full-length proteins of human, cynomolgus or mouse GPVI using Lipofectamine 2000 (Invitrogen) as transfection reagent. Cell were cultivated in selection medium containing Hygromycin B (Roth) until a uniformly GPVI-expressing cell population was observed by fluorocytometry as described below. A cell bank was generated and used for subsequent experiments.

Rat basophilic RBL-2H3 cells (ACC 312, DSMZ) were stably transfected with a pcDNA3.1 vector encoding full-length human GPVI using Lipofectamine 2000 (Invitrogen) as transfection reagent. Cell were cultivated in selection medium containing Geneticin (Gibco) for four weeks. Single clone selection of cells with high GPVI expression was performed using a FACS Aria cell sorter (BD Biosciences). Single clones were expanded in selection medium and checked for GPVI expression level by fluorocytometry. Cell clone with strongest GPVI expression was selected for cell bank generation and used in further experiments.

For fluorocytometric evaluation of GPVI expression levels of transfected cells, cells were blocked in Superblock (Thermo Scientific) and subsequently incubated for 60 min on ice with a GPVI-specific Fab diluted in Superblock to a final concentration of 5 µg/ml. After washing with PBS supplemented with 3% fetal calf serum (FCS) and 0.02% sodium azide, cells were incubated for 30 min on ice with a PE-conjugated anti-F(ab')2 detection antibody (Jackson Immuno Research) diluted in Superblock. Cells were washed again and cells evaluated in a FACS Array (BD Biosciences).

Example 2: Selection of GPVI Specific Antibodies from MorphoSys-Ylanthia™ Library For the antibody generation the MorphoSys Ylanthia® library was used to select Fab fragments against GPVI. The MorphoSys Ylanthia® library (Tiller et al. mAbs 5:3, 1-26; May/June (2013) and U.S. Pat. No. 8,728,981) is a commercially available phagemid library and employs the CysDisplay® technology for displaying the Fab on the phage surface (Lohning et al., WO2001/05950).

To identify GPVI specific antibodies different panning strategies were employed. Each panning strategy comprised at least 3 individual rounds of panning against various GPVI antigens (either as soluble ECD-Fc fusions or overexpressed on CHO-cells) from different species as described in Example 1. The isolated and identified clones were maturated and engineered in order to increase affinity, functionality and safety. Accordingly, several hundred clones were screened and functionality was rigorously tested in in vitro assays comprising e.g.

Binding to human, cynomolgus monkey, mouse and rat GPVI determined by ELISA, Cell-ELISA and/or Solution equilibrium titration (SET)

Inhibition of binding of GPVI to different collagen substrates of GPVI.

Finally, 4 lead molecules (Fab #1, Fab #2, Fab #3, Fab #4) were selected and are further described in the working examples as outlined below.

Each of the 4 lead Fab molecule was generated and produced in two variants; either by having a wild-type human Fab heavy chain constant region or having a modified human heavy chain constant region according SEQ ID NO: 113.

For mammalian production, human Fab fragments were converted from the bacterial to the mammalian Fab format by sub-cloning procedure. Antibody encoding vectors were enzymatically digested and the resulting vector backbones were ligated with the Ylanthia" mammalian expression cassette and further sub-cloned into the respective mammalian human Fab vector.

For generation of the modified heavy chain constant regions according to the present disclosure, the DNA encoding the entire designed heavy chain constant region was synthesized as double-stranded DNA fragments. The resulting synthetic linear DNA fragments comprising the modified heavy chain constant region with homologous overlapping sequences were subsequently seamlessly cloned into the corresponding mammalian human Fab vector by replacing the parental Fab heavy chain constant region.

For expression and purification, eukaryotic HKB11 cells were transfected with pYMex10 eukaryotic expression vector DNA encoding both heavy and light chains of Fabs. Cell culture supernatant was harvested on day 3 post transfection and subjected to Capture select IgG-CH1 affinity chromatography (MabSelect SURE, GE Healthcare) for antibody purification. All samples were sterile filtered (0.2 μm pore size). Purity of Fab was analyzed under denaturing, reducing and non-reducing conditions using a Labchip System (Caliper GXII, Perkin Elmer) or on SDS-PAGE. Protein concentrations were determined by UV-spectrophotometry and HP-SEC was performed to analyze IgG preparations in native state.

Reference Control Antibody RefFab #1: Nucleotide sequences encoding the VH (SEQ ID NO: 99) and the VL (SEQ ID NO: 100) of a humanized GPVI antibody disclosed in WO2011073954A2 (SANOFI) were gene synthesized as linear DNA fragments with appropriate flanking regions (e.g. suitable restriction enzyme recognition sites, linker sequences) either in-house or by an external provider. All synthesized DNA fragments were cloned into suited mammalian Fab expression vectors (as described above) with additionally adding a glycin-cerin linker $(G_4S)_2$ to the C-terminus of the Fab heavy chain using standard molecular biology methods.

Example 3: Binding of Monovalent Fab to Human, Cynomolgus Monkey, Mouse, and Rat GPVI Determined by ELISA Materials and Methods 0.5-2 nM of recombinant GPVI-Fc-fusion proteins (as described in Example 1) were coated overnight on Maxisorp microtiter plates at 4° C. Plates were washed with PBS supplemented with 0.05% Tween-20 (PBST) and subsequently blocked with 5% skim milk powder diluted in PBS (MPBS) for 1 h at room temperature (RT). Following washing with PBST, Fabs (comprising a modified heavy chain constant region) serially diluted to concentrations in the range of 600 nM to 1 pM in PBST with 5% skim milk powder (MPBST) were added for 1 h at RT. Plates were washed with PBST. Bound Fab was detected using an alkaline phosphatase-conjugated detection antibody (Jackson Immuno Research) diluted in MPBST and directed against human F(ab')2 fragment. After washing with TBS supplemented with 0.05% Tween-20 (TBST), AttoPhos substrate (Roche) diluted in ddH2O was added and fluorescence intensity measured at a Tecan Infinite 200Pro reader. EC50 values were calculated using Prism 5 software (GraphPad).

The sequences used for extracellular domain of human, cynomolgus monkey, mouse and rat GPVI are described in SEQ ID NO: 4, SEQ ID NO: 5, SEQ ID NO: 6, SEQ ID NO: 7, SEQ ID NO: 8, SEQ ID NO: 9.

Results and Conclusions

As shown in Table 5, all Fabs (comprising a modified heavy chain constant region) bound to human GPVI isoforms and haplotypes and were cross-reactive with cynomolgus monkey GPVI. In contrast to Fab #1-Fab #4 according to the present disclosure, RefFab #1 did not bind to recombinant mouse and rat GPVI.

TABLE 5

Binding of Fabs to recombinant GPVI-Fc fusion proteins of different species in ELISA. Shown are average EC50 values ± standard deviation (SD) of two experiments. Only one data set is available of Fab#2. nep: no evaluation possible (no EC50 calculation due to incomplete titration).

| | HC | LC | ELISA EC50 [nM] (n = 2; for Fab#2 n = 1) | | | | | |
|---|---|---|---|---|---|---|---|---|
| | SEQ ID NO: | SEQ ID NO: | hGPVI-1a | hGPVI-1b | hGPVI-2a | cyGPVI-2 | mGPVI | rGPVI |
| Fab#1 | 21 | 19 | 0.46 ± 0.30 | 0.66 ± 0.45 | 0.93 ± 0.42 | 0.53 ±0.17 | Binding but nep | Binding but nep |
| Fab#2 | 32 | 30 | 0.41 | 0.45 | 0.65 | 0.42 | 6.55 | 53.06 |
| Fab#3 | 43 | 41 | 0.35 ± 0.09 | 0.39 ± 0.10 | 0.48 ± 0.09 | 0.37 ± 0.08 | 1.36 ± 0.39 | 9.65 ± 6.04 |
| Fab#4 | 54 | 52 | 0.41 ± 0.03 | 0.48 ± 0.08 | 0.74 ± 0.15 | 0.50 ± 0.20 | 1.00 ± 0.06 | 9.32 ± 1.39 |
| RefFab#1 | | | 0.93 ± 0.16 | 1.00 ± 0.29 | 1.43 ± 031 | 0.58 ± 0.13 | no binding | no binding |

Example 4: Binding of Monovalent Fab to Human, Cynomolgus Monkey or Mouse GPVI Expressed on the Cell Surface of Recombinant Cells Determined by Cell-ELISA Materials and Methods CHO cells stably transfected with either human, cynomolgus monkey, or mouse GPVI (SEQ ID NO: 1, SEQ ID NO: 2, SEQ ID NO: 3, respectively and as described in Example 1) were seeded at a density of 5000 cells/well in growth medium on a 96 well high bind plate (Meso Scale Discovery) and cultivated overnight at 37° C. and 5% CO2. Cells were blocked with PBS supplied with 5% BSA and then incubated with Fab (comprising a modified heavy chain constant region) serially diluted to concentrations between 300 nM to 5 pM in PBS supplied with 0.5% BSA. After washing, bound Fab was detected using ECL-conjugated detection antibody directed against human F(ab')2 fragment (Jackson Immuno Research). MSD read buffer (Meso Scale Discovery) was added to cells prior to readout in a Sector Imager6000 (Meso Scale Discovery). EC50 values were calculated using Prism 5 software (GraphPad).

Results and Conclusions

As shown in Table 6, Fab #1-Fab #4 (comprising a modified heavy chain constant region) recognized human and cynomolgus monkey GPVI expressed on cells and revealed binding to cell surface expressed mouse GPVI. As observed in ELISA, RefFab #1 did not bind to cells expressing murine GPVI.

TABLE 6

Binding of Fabs to CHO cells overexpressing GPVI from different species in Cell ELISA. Shown are average EC50 values ± SD of 2-3 experiments.

|  | HC SEQ ID NO: | LC SEQ ID NO: | Cell ELISA EC50 [nM] (n = 2-3) | | |
| --- | --- | --- | --- | --- | --- |
|  |  |  | CHO_hGPVI | CHO_cyGPVI | CHO_mGPVI |
| Fab#1 | 21 | 19 | 0.89 ± 0.42 | 0.74 ± 0.08 | nep |
| Fab#2 | 32 | 30 | 0.78 ± 0.01 | 1.06 ± 0.37 | 8.28 ± 4.35 |
| Fab#3 | 43 | 41 | 0.77 ± 0.04 | 1.06 ± 0.28 | 3.74 ± 1.58 |
| Fab#4 | 54 | 52 | 0.78 ± 0.05 | 0.8 ± 0.15 | 0.93 ± 0.07 |
| RefFab#1 |  |  | 2.80 ± 0.61 | 2.09 ± 0.17 | no binding | nep: no evaluation possible (no EC50 calculation due to incomplete titration).

Example 5: Affinity Determination for Monovalent Fabs on GPVI Determined by Solution Equilibrium Titration (SET)

Materials and Methods

For KD determinations, monomer fractions of Fab protein were used containing at least 90% monomer content, as analyzed by analytical SEC. Affinity determination in solution was basically performed as described in the literature (Friguet et al. 1985). In order to improve the sensitivity and accuracy of the SET method, it was transferred from classical ELISA to ECL-based technology (Haenel et al. 2005).

1 mg/mL goat-anti-human (Fab)2 fragment specific antibodies (Dianova) were labeled with MSD Sulfo TAG™ NHS-Ester (Meso Scale Discovery| Gaithersburg| Md.| USA) according to the manufacturer's instructions. The experiments were carried out in polypropylene microtiter plates and PBS (GIBCO 14190 | pH 7.0-7.2) containing 0.5% BSA and 0.02% Tween20 as assay buffer. Serial dilutions of unlabeled human GPVI-Fc (SEQ ID NO: 4), cynomolgus monkey GPVI-Fc (SEQ ID NO: 7), and mouse GPVI-Fc (SEQ ID NO: 8) (as prepared in Example 1) were prepared, starting with a concentration at least 10 times higher than the expected KD. Wells without antigen were used to determine Bmax values; wells containing only assay buffer were used to determine background. After addition of appropriate amount of binder (antibody concentration similar to or below the expected KD, 60 µL final volume), the mixture was incubated over night at RT. MSD plates were coated with antigen or biotinylated antigen on standard and streptavidin plates, respectively (30 µL per well). After washing the plate with PBS with 0.05% Tween 20, the equilibrated samples were transferred to the plates and incubated for 20 min. Following incubation, 30 µL per well of the MSD-Sulfo-tag labeled detection antibody (anti-human (Fab)2 | final dilution typically 1:2,000) was added to the washed MSD plate and incubated for 30 min at RT on an Eppendorf shaker (700 rpm). After washing the MSD plate and adding 30 µL/well MSD Read Buffer T with surfactant, electrochemiluminescence signals were detected using a Sector Imager 6000 (Meso Scale Discovery| Gaithersburg| Md. | USA). The data was evaluated with XLfit (IDBS) software applying customized fitting models. For KD determination of Fabs the fit model according to (Haenel et al. 2005), modified according to (Abraham et al.) was used.

Results and Conclusions

Results are summarized in Table 7. All tested Fabs (comprising a modified heavy chain constant region) of the present disclosure displayed affinities in the double digit picomolar range on human and cynomolgus monkey GPVI. While Fab #1 and Fab #2 bound mouse GPVI with reasonable weaker affinities of 28 nM and 7 nM, respectively, Fab #4 and Fab #3 displayed sub-nanomlar affinities on mouse GPVI. No affinity to mouse GPVI was determined for RefFab #1 due to lack of binding as confirmed in ELISA and cell ELISA.

TABLE 7

Affinity of anti-GPVI-Fabs on different GPVI species. Shown are average KD values of 1-2 experiments ± SD.

| Antibody | HC SEQ ID NO: | LC SEQ ID NO: | SET KD [pM] | | |
| --- | --- | --- | --- | --- | --- |
|  |  |  | hGPVI | cyGPVI | mGPVI |
| Fab#1 | 21 | 19 | 68 | 75 | 28,000 |
| Fab#2 | 32 | 30 | 27 ± 2 | 24 ± 4 | 7100 ± 1697 |
| Fab#3 | 43 | 41 | 62 ± 4 | 68 ± 13 | 600 ± 113 |
| Fab#4 | 54 | 52 | 22 | 17 | 290 |
| RefFab#1 |  |  | 54 | 36 | not tested |

Example 6: Binding of Monovalent Fabs to GPVI Expressed on the Cell Surface of Human, Cynomolgus Monkey or Mouse Platelets Determined by FACS Materials and Methods Platelet-rich plasma (PRP) from up to 4 donors was prepared by centrifugation of citrated whole blood for 15 min at 150×g without brake. The resulting supernatant was transferred as PRP into a new sample tube without disturbing the underlying leukocyte-rich interphase. After careful washing in Tyrode's buffer supplemented with Prostacyclin $I_2$ (PGI2; Epoprostenol-Rotexmedica), platelets were resuspended in Tyrode's/PGI2 and transferred to 96 well V-bottom microtiter plates. Platelets were spiked with Fab (comprising a modified heavy chain constant region) diluted to final concentrations between 0.015-30 µg/ml in Tyrode's/PGI2 and incubated for 30 min at RT. Platelets were carefully washed to remove non-bound Fab and then incubated for 30 min at RT with a Phycoerythrine (PE)-conjugated detection antibody (Jackson ImmunoResearch). After incubation for 30 min at RT, platelets were analyzed by flow cytometry in a FACS Canto II (Becton Dickinson). In the case of Fab directly conjugated with PE (FIG. 1D), incubation with detection antibody was omitted. Data was evaluated using FACS Diva software (Becton Dickinson). EC50 values were calculated using Prism 5 software (GraphPad).

Results and Conclusions

Results obtained for all 4 Fabs (comprising a modified heavy chain constant region) of the present disclosure on blood platelets from one exemplary donor are shown in FIGS. 1A-C. Additional results for anti GPVI Fabs Fab #3 and Fab #4 (comprising a modified heavy chain constant region) as PE-direct conjugates tested on blood platelets from three human donors are depicted in FIG. 1D.

Fab #1 to Fab #4 revealed specific but donor dependent binding to GPVI expressed on the cell surface of human, cynomolgus monkey and mouse platelets. In contrast to Fab #1 to Fab #4, no binding to GPVI on murine platelets was observed for RefFab #1 which is in line with previous results in ELISA and cell ELISA.

Example 7: Competitive Binding of Monovalent Fabs—Binding Inhibition of Human, Cynomolgus Monkey and Mouse GPVI to Different Collagen Substrates Determined by ELISA Materials and Methods 1 or 10 µg/ml of recombinant GPVI collagen substrate (crosslinked collagen-related peptide (CRP-XL (Anaspec, Inc.), rat-tail collagen (Enzo Life Sciences) or VitroCol (Advanced BioMatrix, Inc.) was coated on a MSD-plate over night at 4° C., washed with PBST, blocked for 1 h at RT with PBS supplemented with 0.05% Tween-20 and 3% skim milk powder, and subsequently washed again with PBST. Purified recombinant GPVI antigens (human, cynomolgus monkey or mouse GPVI as prepared in Example 1) diluted in PBS and varying concentrations of Fab (comprising a modified heavy chain constant region) diluted in PBS (final concentration range 200-0.3 µg/ml) were incubated in a polypropylene plate for 30 min at RT. Fab/GPVI-Fc mixture was added to coated collagen substrate for 1 h at RT. After washing with PBST, bound GPVI form different species was detected using an ECL-conjugated detection antibody directed against human Fc (Jackson Immuno Research) for 1 h at RT. MSD read buffer (Meso Scale Discovery) was added prior to readout in a Sector Imager6000 (Meso Scale Discovery). Inhibition of the GPVI/ligand interaction by the Fab resulted in decreasing signals.

Results and Conclusions

Results are summarized in Table 8 (for human GPVI), Table 9 (for cynomolgus monkey GPVI) and Table 10 (for mouse GPVI). Indicated are the IC50 values and the maximum achieved inhibitory effect of anti-GPVI Fabs (comprising a modified heavy chain constant region) for different GPVI collagen substrates.

For all tested Fabs, comparable IC50 values were obtained on each GPVI/substrate combination with the exception of mouse GPVI. Here, binding to the different substrates could not be blocked by RefFab #1 due to the lack of mouse cross-reactivity.

With regard to the maximal inhibition of GPVI/substrate-binding, Fab #2 and Fab #3 completely inhibited binding of GPVI to the different collagen substrates at 200 nM, Fab #1 and Fab #4 did not reach complete inhibition. The strongest difference appeared when using CRP-XL: binding of this substrate to GPVI was inhibited by 47% to 77% by Fab #1 and Fab #4.

TABLE 8

Inhibition of human GPVI-Fc binding to different coated GPVI collagen substrates. Potency of Fabs is illustrated as IC50 value and efficacy as % inhibition of GPVI/substrate binding obtained at the highest Fab concentration tested. Shown are average values ± SD of two experiments.

| | | | Competition ELISA with human GPVI (n = 2, average) | | | | | |
|---|---|---|---|---|---|---|---|---|
| | | | IC50 [nM] | | | Maximum inhibition at 200 nM Fab [%] | | |
| | HC SEQ ID NO: | LC SEQ ID NO: | CRP-XL | VitroCol | Rat-tail collagen | CRP-XL | VitroCol | Rat-tail collagen |
| Fab#1 | 21 | 19 | 10.9 ± 4.5 | 8.2 ± 3.6 | 11 ± 6.9 | 63 ± 6 | 79 ± 0 | 89 ± 1 |
| Fab#2 | 32 | 30 | 8.3 ± 0.8 | 5.4 ± 0.1 | 6.3 ± 0.2 | 100 ± 0 | 100 ± 0 | 100 ± 0 |
| Fab#3 | 43 | 41 | 8.7 ± 1.4 | 5.6 ± 0.7 | 6.3 ± 0.4 | 100 ± 0 | 99 ± 1 | 99 ± 0 |
| Fab#4 | 54 | 52 | 13.2 ± 2.0 | 10.6 ± 1.0 | 8.2 ± 0.7 | 47 ± 5 | 82 ± 7 | 86 ± 0 |
| RefFab#1 | | | 10.6 ± 0.7 | 5.8 ± 0.7 | 7 ± 0.0 | 100 ± 0 | 100 ± 0 | 99 ± 0 |

TABLE 9

Inhibition of cynomolgus GPVI-Fc binding to different coated GPVI collagen substrates. Potency of Fabs is illustrated as IC50 value and efficacy as % inhibition of GPVI/substrate binding obtained at the highest Fab concentration tested. Shown are average values ± SD of two experiments.

| | | | Competition ELISA with cyno GPVI (n = 2, average) | | | | | |
|---|---|---|---|---|---|---|---|---|
| | | | IC50 [nM] | | | Max. inhibition at 200 nM Fab [%] | | |
| | HC SEQ ID NO: | LC SEQ ID NO: | CRP-XL | VitroCol | Rat-tail collagen | CRP-XL | VitroCol | Rat-tail collagen |
| Fab#1 | 21 | 19 | 11.5 ± 6.3 | 9.7 ± 2.6 | 9.6 ± 2.8 | 59 ± 6 | 84 ± 7 | 86 ± 1 |
| Fab#2 | 32 | 30 | 7.9 ± 1.3 | 4.3 ± 1.0 | 7.1 ± 0.5 | 100 ± 0 | 100 ± 0 | 100 ± 0 |
| Fab#3 | 43 | 41 | 9.1 ± 1.2 | 4.7 ± 2.0 | 7.6 ± 0.8 | 100 ± 0 | 100 ± 0 | 99 ± 1 |
| Fab#4 | 54 | 52 | 11.3 ± 3.7 | 8.1 ± 2.5 | 9.1 ± 2.8 | 51 ± 12 | 91 ± 2 | 83 ± 2 |
| RefFab#1 | | | 9.5 ± 0.2 | 5.5 ± 0.1 | 8.8 ± 0.6 | 100 ± 0 | 100 ± 0 | 99 ± 0 |

TABLE 10

Inhibition of mouse GPVI-Fc binding to different coated GPVI collagen substrates. Potency of Fabs is illustrated as IC50 value and efficacy as % inhibition of GPVI/substrate binding obtained at the highest Fab concentration tested. Shown are average values ± SD of two experiments. no inh. = no inhibition

| | | | Competition ELISA with mouse GPVI (n = 2, average) | | | | | |
|---|---|---|---|---|---|---|---|---|
| | | | IC50 [nM] | | | Max. inhibition at 200 nM Fab [%] | | |
| | HC SEQ ID NO: | LC SEQ ID NO: | CRP-XL | VitroCol | Rat-tail collagen | CRP-XL | VitroCol | Rat-tail collagen |
| Fab#1 | 21 | 19 | 26.4 ± 14.3 | 9.1 ± 5.1 | 17.2 ± 9.2 | 77 ± 2 | 96 ± 2 | 89 ± 5 |
| Fab#2 | 32 | 30 | 12 ± 1.1 | 4.3 ± 0.6 | 5.7 ± 1.7 | 99 ± 0 | 99 ± 1 | 99 ± 0 |
| Fab#3 | 43 | 41 | 8.1 ± 0.7 | 3.3 ± 0.1 | 5.3 ± 2.1 | 100 ± 0 | 100 ± 0 | 99 ± 1 |
| Fab#4 | 54 | 52 | 10.6 ± 3.9 | 6.7 ± 2.0 | 0.8 ± 2.0 | 67 ± 2 | 94 ± 3 | 87 ± 5 |
| RefFab#1 | | | no inh. | no inh. | no inh. | no inh. | no ink. | no inh. |

Example 8: Cell Adhesion Assay

Materials and Methods

Recombinant GPVI-substrate (1 µg/ml crosslinked collagen-related peptide (CRP-XL (Anaspec, Inc.) or 10 µg/ml VitroCol (Advanced BioMatrix, Inc.)) diluted in carbonate buffer (15 mM Na2CO3, 35 mM NaHCO$_3$, pH 9.6) was coated on a 96-well microtiter Maxisorp plate over night at 4° C. After washing with PBS, wells were blocked with PBS supplemented with 2% BSA. Rat basophilic RBL-2H3 cells stably transfected with human GPVI were detached from culture flasks, washed with attachment buffer (OptiMEM supplemented with 0.5% BSA and 10 mM HEPES) and stained with 2.5 µg/ml Calcein-AM (Molecular Probes) for 30 min at 37° C. Cells were incubated with anti-GPVI Fabs (comprising a modified heavy chain constant region) diluted in attachment buffer (final concentration range 100 nM to 10 pM) in 96-well polypropylene microtiter plates for 30 min shaking at RT in the dark. Coated and blocked Maxisorp plates were washed with PBS and incubated with cell-antibody-mixture for 30 min at RT and subsequently for 30 min at 37° C. After further gentle washing, bound cells were assessed by measuring fluorescence intensity (excitation at 485 nm, emission at 530 nm) in a Tecan Infinite M1000 Pro reader. Inhibition of cell adhesion results in signal reduction compared to untreated control cells.

Results and Conclusions

Results are summarized in Table 11 for RBL-2H3 cells expressing human GPVI and recombinant collagen substrate CRP-XL and VitroCol. Indicated are the $IC_{50}$ values and the maximum achieved inhibitory effect of anti-GPVI Fab fragments at an antibody concentration of 200 nM.

Fab #1 to Fab #4 (comprising a modified heavy chain constant region) potently inhibited cell binding to coated VitroCol with comparable half-maximal concentrations in the range of 0.57 to 1.17 nM. For CRP-XL, similar results were obtained for Fab #2 and Fab #3, while Fab #1 and Fab #4 had no relevant effect on cell binding to this substrate.

With regard to efficacy, Fab #2 and Fab #3 completely (100%) and almost completely (91-93%) inhibited cell binding to CRP-XL and VitroCol, respectively. The maximum inhibitory effects of Fab #1 and Fab #4 on VitroCol were 55% and 59%, respectively.

TABLE 11

Inhibition of human GPVI overexpressing RBL-2H3 cell binding to different coated collagen substrates. Potency of Fabs is illustrated as IC50 value and efficacy as % inhibition of cell/substrate binding obtained at the highest Fab concentration tested. Shown are average values ± SD of two experiments.

|  | HC | LC | Cell adhesion assay with RBL-2H3 hGPVI cells (n = 2, average) | | | |
|---|---|---|---|---|---|---|
|  |  |  | IC50 [nM] | | Max. inhibition at 200 nM Fab [%] | |
|  | SEQ ID NO: | SEQ ID NO: | CRP-XL | VitroCol | CRP-XL | VitroCol |
| Fab#1 | 21 | 19 | no inhibition | 0.58 ± 0.2 | no inhibition | 55 ± 8 |
| Fab#2 | 32 | 30 | 1.59 ± 0.2 | 0.89 ± 0.6 | 100 ± 0 | 93 ± 5 |
| Fab#3 | 43 | 41 | 1.81 ± 0.2 | 0.84 ± 0.5 | 100 ± 0 | 91 ± 5 |
| Fab#4 | 54 | 52 | no inhibition | 0.57 ± 0.2 | no inhibition | 59 ± 13 |
| RefFab#1 |  |  | 2.69 ± 0.1 | 1.17 ± 0.6 | 100 ± 0 | 92 ± 5 |

Example 9: Inhibition of Collagen Induced Human Platelet Aggregation—Multiplate® Impedance Aggregometry Materials and Methods Hirudin-anti-coagulated blood was diluted 1:1 with 0.9% NaCl in Multiplate® standard test cells (Roche), spiked with anti-GPVI Fab (comprising a modified heavy chain constant region) pre-diluted in PBS to 10, 3.3, 1.1 and 0.37 µg/ml, and pre-incubated for 3 min at 37° C. with stirring. Subsequently, platelet aggregation was induced by addition of different platelet agonist substrates (CRP-XL (1 µg/ml; Anaspec, Inc.), VitroCol (100 µg/ml; Advanced BioMatrix, Inc.), rabbit aorta collagen (4 µg/ml; AdvanceCor), cyno aorta collagen (7.4 µg/ml; AdvanceCor), TRAP-6 (8 µM; TRAPtest, Roche), ADP (6.5 µM; ADPtest, Roche)). To evaluate an intrinsic agonistic potential of the anti GPVI Fab on platelets by themselves, the effect of Fab was also investigated in the absence of agonists. Platelet aggregation was then determined in a Multiplate® device (Roche) for six minutes at 37° C. with continued stirring by measuring the increase of the impedance between the sensor wires of the test cells over time, which was induced by aggregated platelets.

Results and Conclusions

Figure 2:
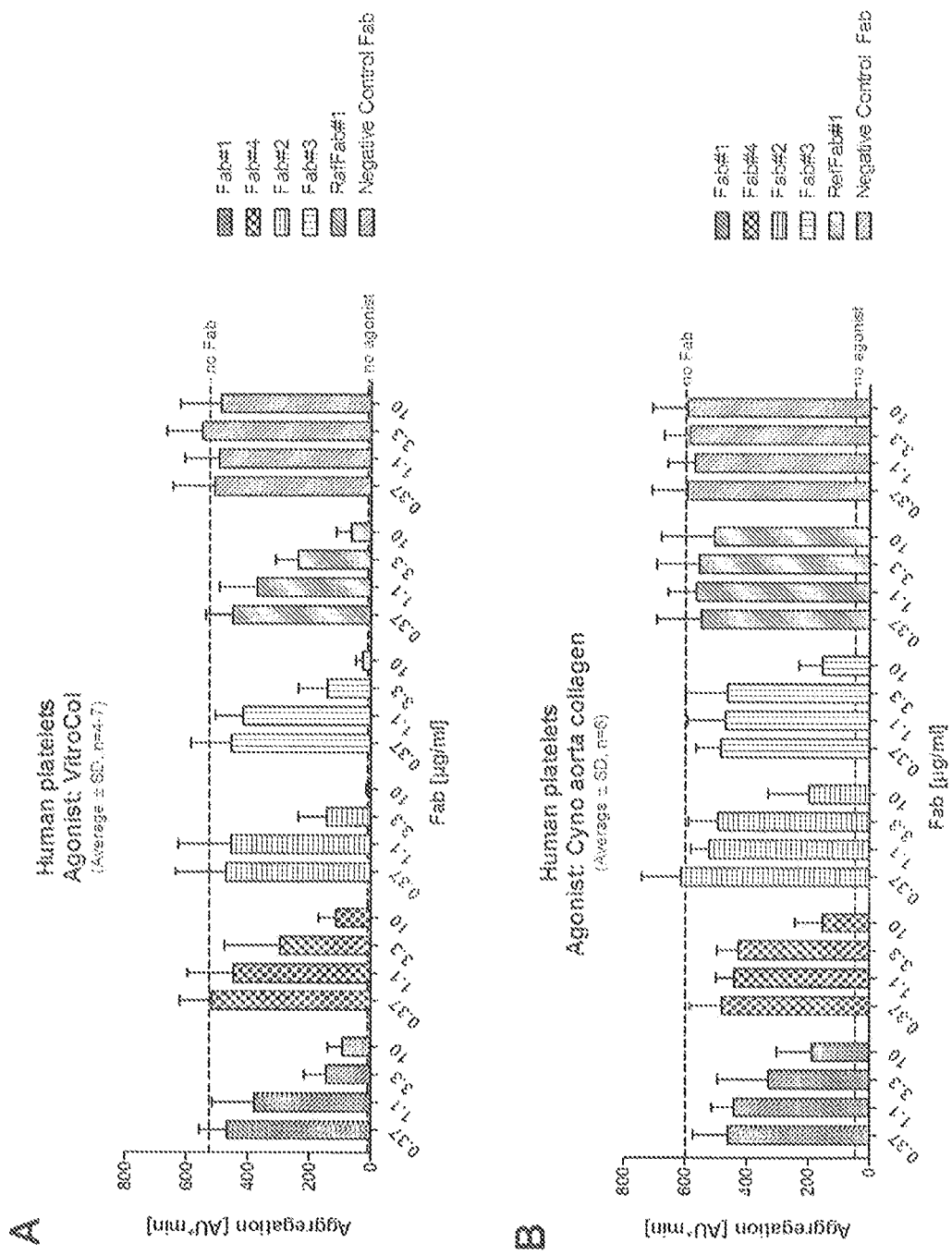
FIG. 2: In vitro inhibition of recombinant human collagen VitroCol (A) and cyno aorta collagen (B) induced Human Platelet Aggregation by Fab #1, Fab #2, Fab #3 and Fab #4 (comprising a modified heavy chain constant region) under static conditions. Platelet aggregation was measured in a Multiplate® device as increasing impedance over a time course of six minutes. Shown are average values±SD of blood samples from 4-7 donors.

Table 12 indicates the inhibitory activity of anti-GPVI Fabs Fab #1 to Fab #4 (comprising a modified heavy chain constant region) on platelet aggregation induced by GPVI dependent and GPVI independent agonists. Detailed results for GPVI agonists VitroCol and Cyno Aorta Collagen are summarized in FIGS. 2A and 2B, respectively.

In sum, the results demonstrate that the GPVI specific Fabs according to the present disclosure inhibited platelet aggregation induced by GPVI dependent collagen agonists. The degree of inhibition depended on Fab and agonist used. Fab #2 and Fab #3 revealed most potent dose dependent inhibitory activity on aggregation of human platelets induced by the human collagen substrates CRP-XL and VitroCol with the ability to fully inhibit aggregation of human platelets at a Fab concentration of 10 µg/ml. Functional superiority of these two Fabs over RefFab #1 could be shown for all tested collagen substrates. No inhibitory effect was observable for the GPVI independent agonists TRAP and ADP indicating GPVI specific effects. Moreover, none of the tested Fabs induced platelet aggregation in the absence of an agonist, thus ruling out an intrinsic agonistic activity of the Fabs.

TABLE 12

Effect of anti-GPVI Fabs on platelet aggregation induced by different agonists or in absence of agonists as assessed by multiple electrode aggregometry using a Multiplate ® device. Each Fab-agonist combination was tested with blood samples of 4-7 donors. Degree of aggregation inhibition by Fabs is represented in four categories from "strong dose dependent inhibition" (+++) to "no inhibition"(0).

| | HC SEQ ID NO: | LC SEQ ID NO: | CRP-XL | VitroCol | rabbit aorta collagen | cyno aorta collagen | TRAP* | ADP* | Absence of agonists |
|---|---|---|---|---|---|---|---|---|---|
| Fab#1 | 21 | 19 | + | ++ | +++ | + | 0 | 0 | no activation |
| Fab#4 | 54 | 52 | + | + | ++ | + | 0 | 0 | no activation |
| Fab#2 | 32 | 30 | +++ | +++ | ++ | + | 0 | 0 | no activation |
| Fab#3 | 43 | 41 | +++ | +++ | ++ | + | 0 | 0 | no activation |
| RefFab#1 |  |  |  | ++ | ++ | + | 0 | 0 | no activation |

+++ strong dose dependent inhibition
++ moderate dose dependent inhibition
+ weak dose dependent inhibition No
0 inhibition
*GPVI independent agonists

Example 10: Inhibition of Human Atherosclerotic Plaque-Induced Human Platelet Aggregation—Multiplate® Impedance Aggregometry Materials and Methods In order to assess the inhibitory activity of anti-GPVI Fabs (comprising a modified heavy chain constant region) on human platelet aggregation reflecting a relevant disease setting, atherosclerotic plaque-induced platelet aggregation was measured in a static system by Multiple Electrode Aggregometry (MEA) using the Multiplate® device as described previously (Toth et al., Thromb Haemost, 2006) according to a recently modified protocol (Bampalis et al., J Thromb Haemost, 2012). Human atherosclerotic plaque material (which was obtained from patients undergoing endarterectomy for high grade carotid artery stenosis.

The antibodies were incubated at concentrations of 2, 1, 0.5 and 0.2 µg/ml for three minutes at 37° C. in 0.3 ml of anticoagulated blood diluted with 0.3 ml saline in Multiplate® cuvettes before inducing aggregation by spiking human pooled plaque homogenate (333 µg/ml). The increase in electrical impedance was recorded continuously for six minutes. Specificity of the anti-GPVI antibodies was assessed by aggregation induction by GPVI-independent agonists ADP (0.5-2 µM) and the PAR-1 agonist TRAP (2-10 µM).

Results and Conclusions

Figure 3:
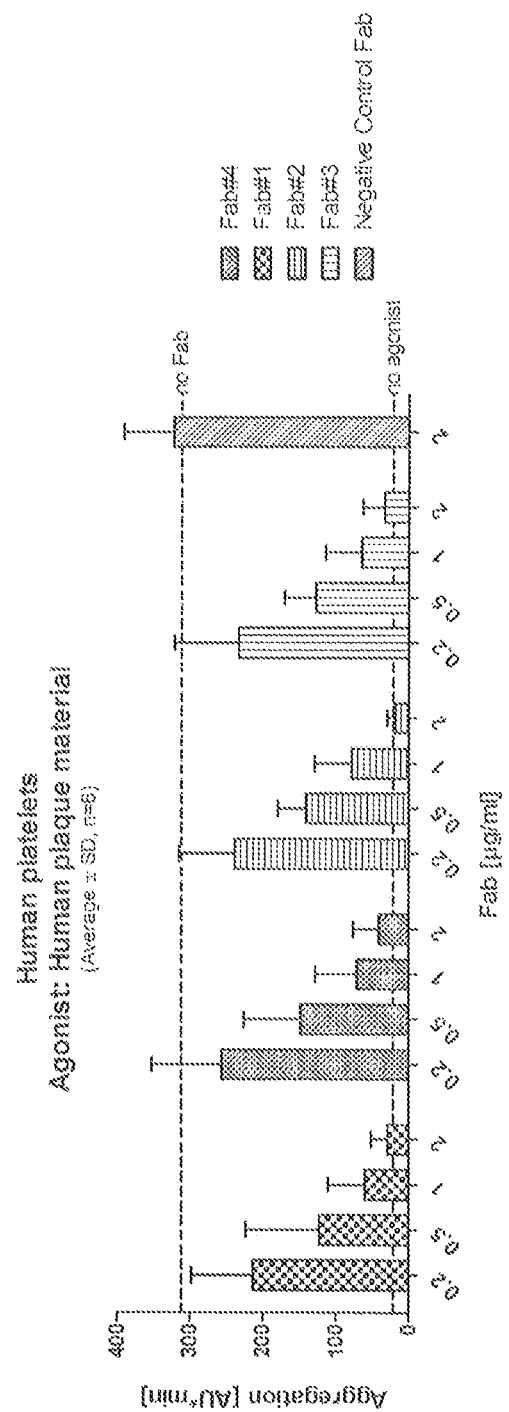
FIG. 3: In vitro inhibition of Human Atherosclerotic Plaque induced Human Platelet Aggregation by Fab #1, Fab #2, Fab #3 and Fab #4 (comprising a modified heavy chain constant region) under static conditions. Platelet aggregation was measured in a Multiplate® device as increasing impedance over a time course of six minutes. Shown are average values±SD of blood samples from 6 donors.

FIG. 3 indicates the inhibitory activity of anti-GPVI Fabs (comprising a modified heavy chain constant region; with heavy and light chain sequences according Table 12) of the present disclosure on platelet aggregation induced by human pooled plaque homogenate. The results confirm a strong dose dependent inhibitory activity for all tested Fabs on human plaque induced aggregation of human platelets with almost complete or complete inhibition of aggregation at a Fab concentration of 2 µg/ml.

Example 11: Inhibition of Human Atherosclerotic Plaque-Induced Human Platelet Aggregation Under FLOW Conditions—Flow Chamber Materials and Methods Glass cover slips were coated with pooled plaque homogenates (diluted 1:20 in PBS) obtained from patients undergoing endarterectomy for high-grade carotid arterial stenosis. Cover slips were mounted into parallel plate flow chambers using 0.1 Luer sticky slides (Ibidi®) which had been blocked with PBS supplemented with 4% human serum albumin (HSA). The flow chamber was mounted on the stage of a TE2000-E fluorescence microscope (Nikon) equipped with an incubation chamber (37° C.). Plaque-coated flow chambers were perfused with PBS and subsequently blocked with PBS containing 4% HSA. Platelets in hirudinzed human whole blood stained with 1 µM DiOC6 and incubated with 2 µg/mlanti-GPVI Fab (comprising a modified heavy chain constant region), P2Y12 antagonist ticagrelor or controls for 10 min. Where indicated, 1 mM ASA was added to blood during blood collection. Blood was perfused through the flow chamber at a shear rate of 600/s·Adhesion and aggregation of labeled platelets was continuously recorded in real-time for 6 min (1 frame/sec) using a 10× objective and a CoolSNAP HQ2 CCD camera. Platelet coverage was analyzed by quantifying the binary fluorescent area fraction using the NIS-element 3.2 software package (Nikon).

Results and Conclusions

Figure 4:
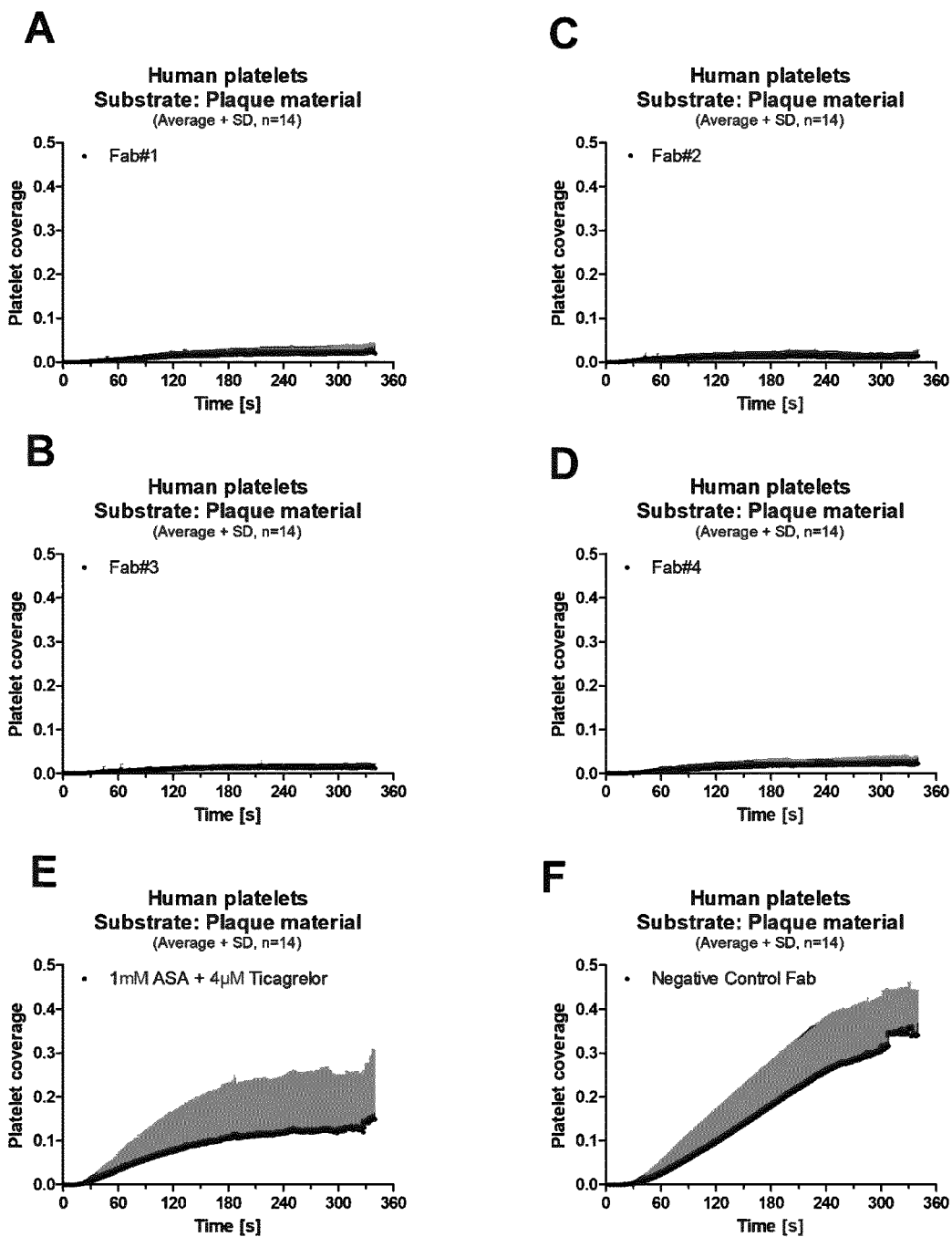
FIG. 4: A-D) In vitro inhibition of Human Atherosclerotic Plaque induced Human Platelet Adhesion/Aggregation under flow conditions by Fab #1, Fab #2, Fab #3 and Fab #4 (comprising a modified heavy chain constant region)

FIG. 4 A-D indicates the inhibitory activity of anti-GPVI Fabs Fab #1 to Fab #4 (comprising a modified heavy chain constant region; with heavy and light chain sequences according Table 12) on platelet aggregation induced by human pooled plaque homogenate under physiological flow conditions.

The results strongly indicate that Fab #1 to Fab #4 were able to almost completely inhibit platelet activation/aggregation in the presence of human plaque material at a concentration of 2 µg/ml. Moreover, all Fabs were clearly superior to the standard of care combination of ASA and Ticagrelor (FIG. 4E)

Example 12: In Vivo Efficacy—Effect of GPVI Specific Monovalent Fab in a Mouse Model of Arterial Thrombosis—Ligation-Induced Thrombosis Model Materials and Methods Intravital fluorescence microscopy was performed as described previously (Seizer et al., 2015). In brief, genetically modified mice ("ROSA"-strain) on a C57Bl/6J background were used for imaging thrombus formation. The mice were "wildtype" mice with green fluorescent platelets. The mice were anesthesized by injection of midazolame (5 mg/kg body weight), medetomidine (0.5 mg/kg body weight) and fentanyl (0.05 mg/kg body weight). The common carotid artery was dissected, and subsequently injured by a standardized vigorous ligation for 5 min (Seizer et al., 2015). Prior to ligation, 3.3 mg/kg anti-GPVI or control Fab were administered i.v. into the tail vein. Before and immediately after injury, the thrombus formation, i.e. adhesion and aggregation of fluorescent platelets to the damaged vessel wall, was visualized by in vivo video microscopy. Recording time per vessel was 20 minutes. Analysis was done by determining the percentage of thrombus covered area in relation to total injured area at indicated time points using AxioVision Software (Carl Zeiss). All animal experiments were conducted according to the German law for the care and use of laboratory animals and were approved by local authorities.

Results and Conclusions

Figure 5:
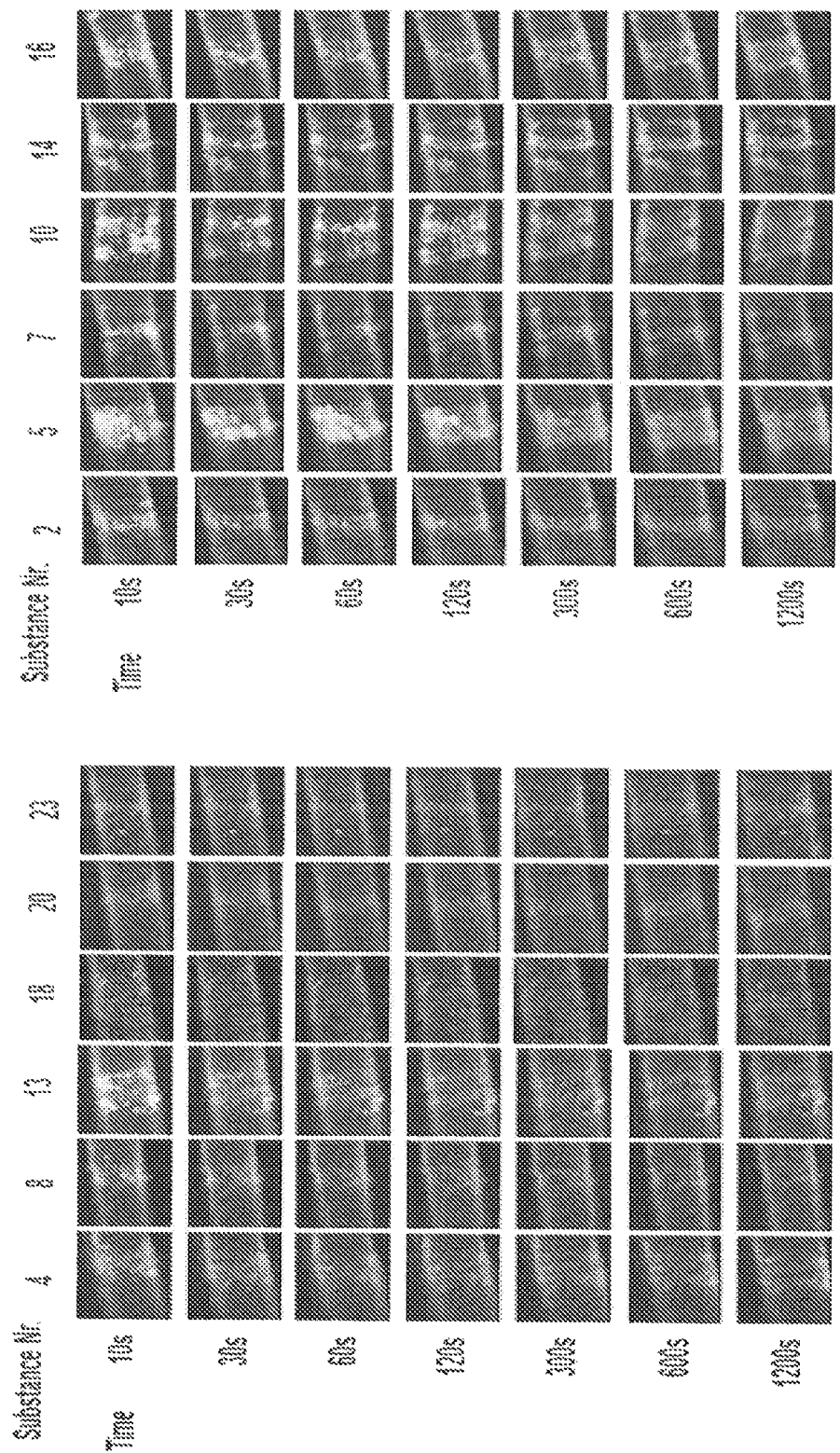
FIG. 5: Effect of anti-GPVI Fab Fab #3 (comprising a modified heavy chain constant region) (FIG. 5A) and negative control Fab (FIG. 5B) on in vivo thrombus formation in a mouse model of arterial thrombosis (ligation-induced thrombosis model) after 3 mg/kg IV bolus administration. Thrombus formation was visualized by intravital video microscopy detecting fluorescent platelets and recorded for 20 minutes per vessel. Shown are the results for six mice per group at different time points.
Figure 6:
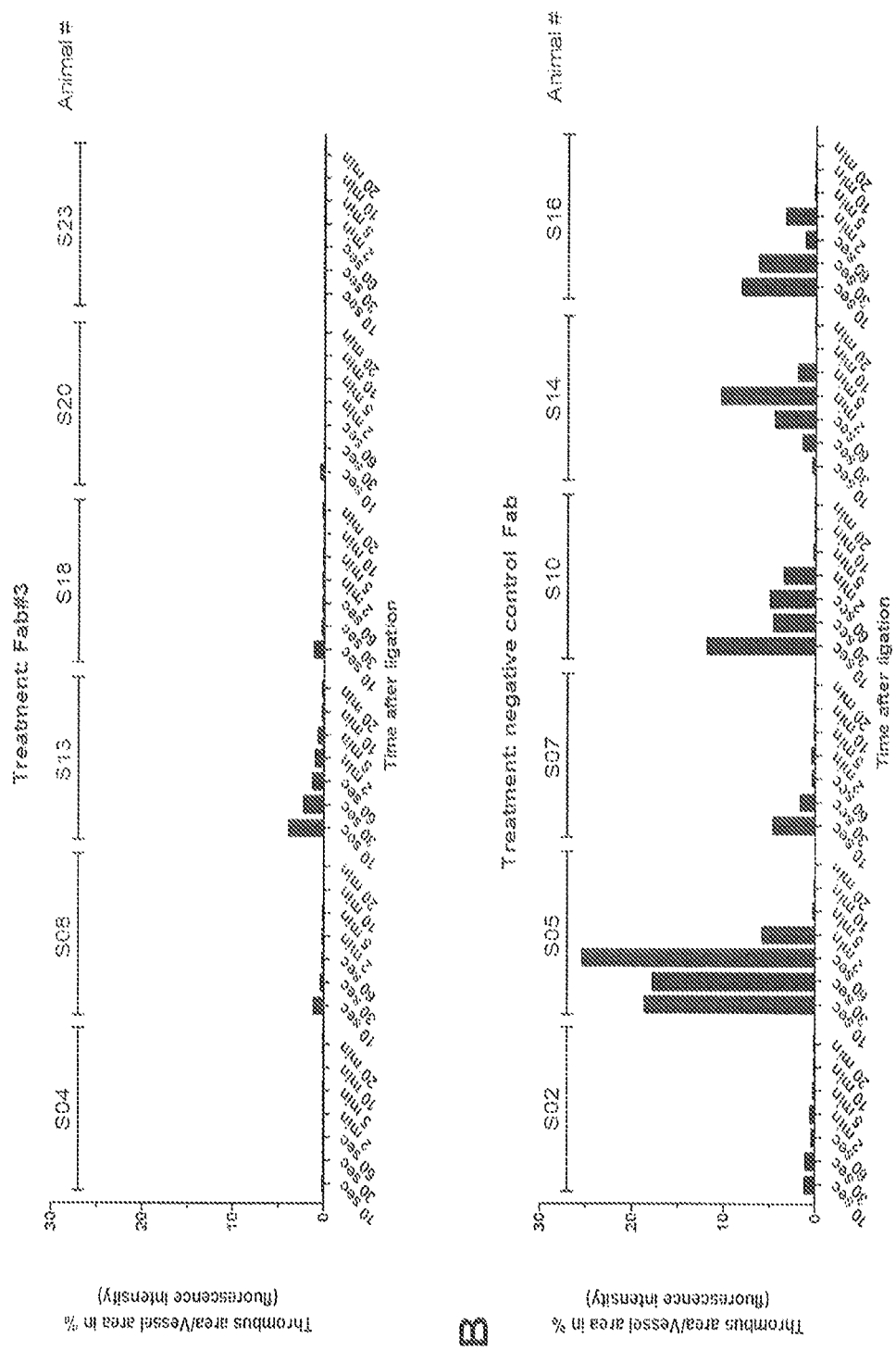
FIG. 6: Effect of anti-GPVI Fab Fab #3 (comprising a modified human heavy chain constant region) (FIG. 6A) and negative control Fab (FIG. 6B) on in vivo thrombus formation in a mouse model of arterial thrombosis (ligation-induced thrombosis model) after 3 mg/kg IV bolus administration. Y-axis depicts thrombus area/vessel area in [%] as a function of fluorescence intensity of the fluorescent platelets. Shown are the results for six mice per group at different time points.

FIG. 5 and FIG. 6 illustrates the inhibitory activity of anti-GPVI Fab Fab #3 (comprising a modified heavy chain constant region; heavy chain sequence of SEQ ID NO: 43 and light chain sequence of SEQ ID NO: 41) on thrombus formation at 7 different time points and six tested animals in comparison to the negative control Fab. Thrombus formation was observed for all animals treated with negative control Fab whereas intravenous bolus administration of 3.3 mg/kg anti-GPVI Fab Fab #3 significantly inhibited thrombus formation in 5/6 animals. In 1/6 animal treated with Fab #3, initial thrombus formation did occur, but did not persist over time.

Example 13: Platelet Activation—Ex Vivo CD62P Surface Expression

Materials and Methods

Receptor activation and subsequent downstream signaling was evaluated by fluorometric assessment of the cell surface expression of the platelet activation marker CD62P. Platelet-rich plasma (PRP) was generated by centrifugation of citrated whole blood for 15 min at 500×g at RT without brake. The resulting supernatant was transferred as PRP into a new sample tube without disturbing the underlying leukocyte-rich interphase. Platelets in PRP were incubated in a 96 well V-bottom plate with 10 µg/ml anti-GPVI Fab either bearing a modified or wildtype human heavy chain constant region diluted in PBS and incubated for 30 min at RT. Subsequently, phycoerythrin-conjugated antibody directed against CD62P (BD Pharmingen) was added followed by incubation for 20 min at RT protected from light. Cells were fixated with 1% formaldehyde solution for at least 30 min at 4° C. and analyzed using BD FACS CANTO™ II (BD Biosciences). Basal CD62P expression was determined by incubation with PBS instead of Fab. Fab-induced GPVI activation is represented as level of activation marker expression in the presence of Fab normalized to basal expression level in the presence of PBS.

Results and Conclusions

Figure 7:
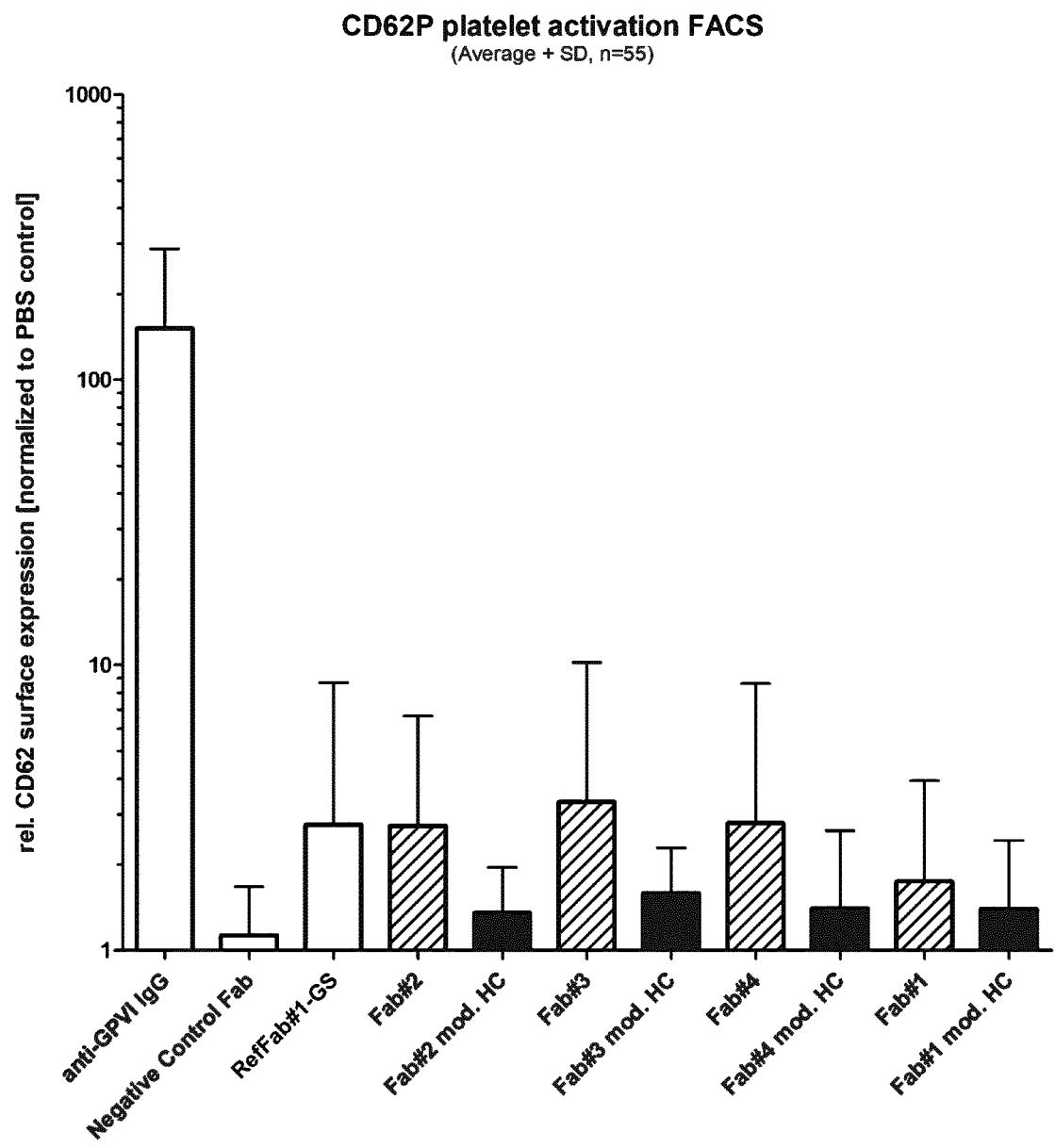
FIG. 7: FACS based characterization of Fab #1, Fab #2, Fab #3 and Fab #4 for their potential to induce GPVI receptor activation through pre-existing anti-Fab antibodies present in human plasma samples. Fabs were tested either with a wildtype human heavy chain constant region (Fab #1, Fab #2, Fab #3 and Fab #4) or with a modified human heavy chain constant region (Fab #1 mod. HC, Fab #2 mod. HC, Fab #3 mod HC. and Fab #4 mod. HC) according to the present disclosure comprising SEQ ID NO: 113. Platelet activation is represented by the relative CD62P surface expression on human platelets normalized to the CD62P expression of the PBS control. Shown are average values±SD of PRP samples from 55 donors.

Results are illustrated in FIG. 7. Anti-GPVI Fabs comprising a modified heavy chain constant region (Fab #1 mod. HC, Fab #2 mod. HC, Fab #3 mod. HC and Fab #4 mod. HC) induced CD62P expression to a much weaker extent compared to an anti-GPVI IgG due to a lack of GPVI crosslinking as a result of monovalent binding. Residual platelet activation potentially resulted from the crosslinking of GPVI-bound Fabs by pre-existing anti-Fab antibodies present in human serum. Using anti-GPVI Fab (Fab #1 mod. HC, Fab #2 mod. HC, Fab #3 mod. HC, Fab #4 mod. HC) comprising a modified heavy chain constant region further reduced the expression of the platelet activation marker CD62P when compared to the Fabs (Fab #1, Fab #2, Fab #3, Fab #4) comprising the unmodified human Fab heavy chain constant region suggesting that the modification efficiently prevented the binding of anti-Fab antibodies present in human serum to these Fabs. This effect was not observed when attaching a glycin-serin-linker to the Fab heavy chain C-terminus as described for RefFab #1.

TABLE 14

Heavy and light chain sequences of tested human unmodified Fab constructs

| | Fab with wild-type heavy chain constant region | |
|---|---|---|
| | HC SEQ ID NO: | LC SEQ ID NO: |
| Fab#1 | 20 | 19 |
| Fab#2 | 31 | 30 |
| Fab#3 | 42 | 41 |
| Fab#4 | 53 | 52 |

TABLE 15

Heavy and light chain sequences of tested Fab constructs with a modified human heavy chain constant region

| | Fab with modified heavy chain constant region | |
|---|---|---|
| | HC SEQ ID NO: | LC SEQ ID NO: |
| Fab#1 mod. HC | 21 | 19 |
| Fab#2 mod. HC | 32 | 30 |
| Fab#3 mod. HC | 43 | 41 |
| Fab#4 mod. HC | 54 | 52 |

Example 14: In Vivo Bleeding Time—Mouse Tail Clipping Model

Materials and Methods

The effect of Fab-mediated GPVI-blockade on bleeding time was evaluated in a mouse tail clipping model. Tail-bleeding was induced in C57BL/6J mice by dissecting the distal 2 mm of the tail with a scalpel blade and immersing the tail in warm PBS. Mice were anaesthesized with medetomidine (Domitor® 0.5 mg/kg), midazolam (Dormicum® 5 mg/kg) and fentanyl (Fentanyl B. Braun 0.05 mg/kg) intraperitoneally approximately 10 min prior to tail transection. Anti-GPVI Fab (comprising a modified heavy chain constant region) (10 mg/kg in PBS) or controls were applied i.v. into the tail vein 30 min prior to tail transsection. Where indicated, ASA was injected i.v. 60 min prior to tail transsection. Bleeding time was recorded immediately following transection and was continued until blood ceased to flow from the tip of the tail without restarting within 30 sec. At the end of the study, anaesthetized animals were killed by cervical dislocation. The experiment was conducted according to the German law for the care and use of laboratory animals and was approved by local authorities.

Results and Conclusion

Figure 8:
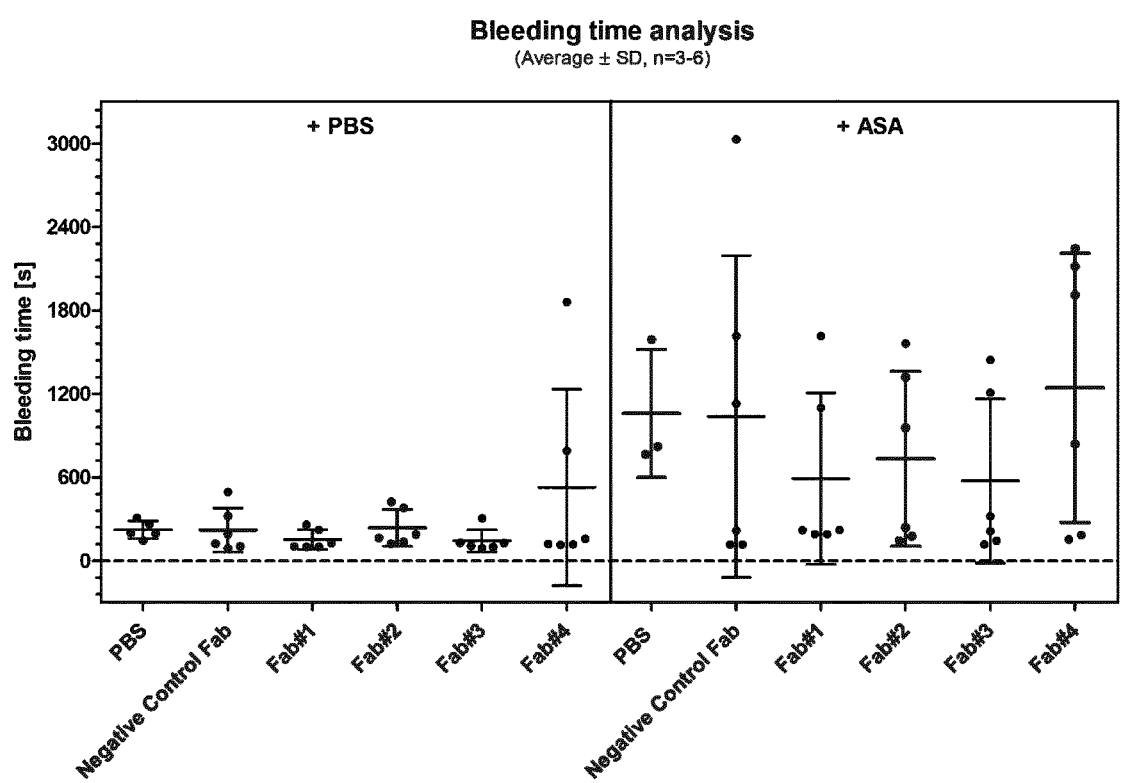
FIG. 8: Effect of anti-GPVI Fab (comprising a modified heavy chain constant region) (Fab #1, Fab #2, Fab #3 and Fab #4) mediated GPVI-blockade on bleeding time. Tail-bleeding was induced in C57BL/6J mice by dissecting the distal 2 mm of the tail with a scalpel blade and immersing the tail in warm PBS. Bleeding time was recorded until blood ceased to flow from the tip of the tail without restarting within 30 sec. Left Panel depicts bleeding time without co-administration of ASA. Right panel depicts bleeding time with co-administration of ASA. Shown are average bleeding times±SD of 3-6 mice per treatment group.

As shown in FIG. 8, anti-GPVI Fabs (Fab #1, Fab #2, Fab #3, Fab #4) comprising a modified heavy chain constant region (with heavy and light chain sequences according Table 12) alone did not cause a prolongation of bleeding time in an mouse tail clipping model. Furthermore, combination of anti-GPVI Fabs with ASA did not further increase the bleeding time compared to Aspirin alone. These results imply that treatment with anti-GPVI Fabs does not lead to an increased bleeding risk.

Example 15: Platelet Count

Materials and Methods

To assess its influence on platelet count, 10 mg/kg of anti-GPVI Fab comprising a modified heavy chain constant region (Fab #1, Fab #2, Fab #3 and Fab #4) (with heavy and light chain sequences according Table 12) or control were applied i.v. into the tail vein of C57BL/6J mice. Directly prior to and 30 min after compound injection blood samples were collected from the tail vein contralateral to the vein used for drug application. Blood samples were collected in end-to-end capillary 25 µl K2E tubes (Sanguis Counting) and diluted 1:50 in Tyrode's buffer (pH 7.3). Diluted blood samples were stained with APC-conjugated anti-CD41 antibody (Biolegend) for 10 min at RT in the dark, further diluted 1:50 in Tyrode's buffer (pH 7.3), and subsequently analyzed in a BD FACS CANTO™ II (BD Biosciences). 25 µl of CD41-positive events were recorded. Platelet count was determined according to the equation: Events*2500/25=Events*100 [platelets/µl].

Results and Conclusion

Figure 9:
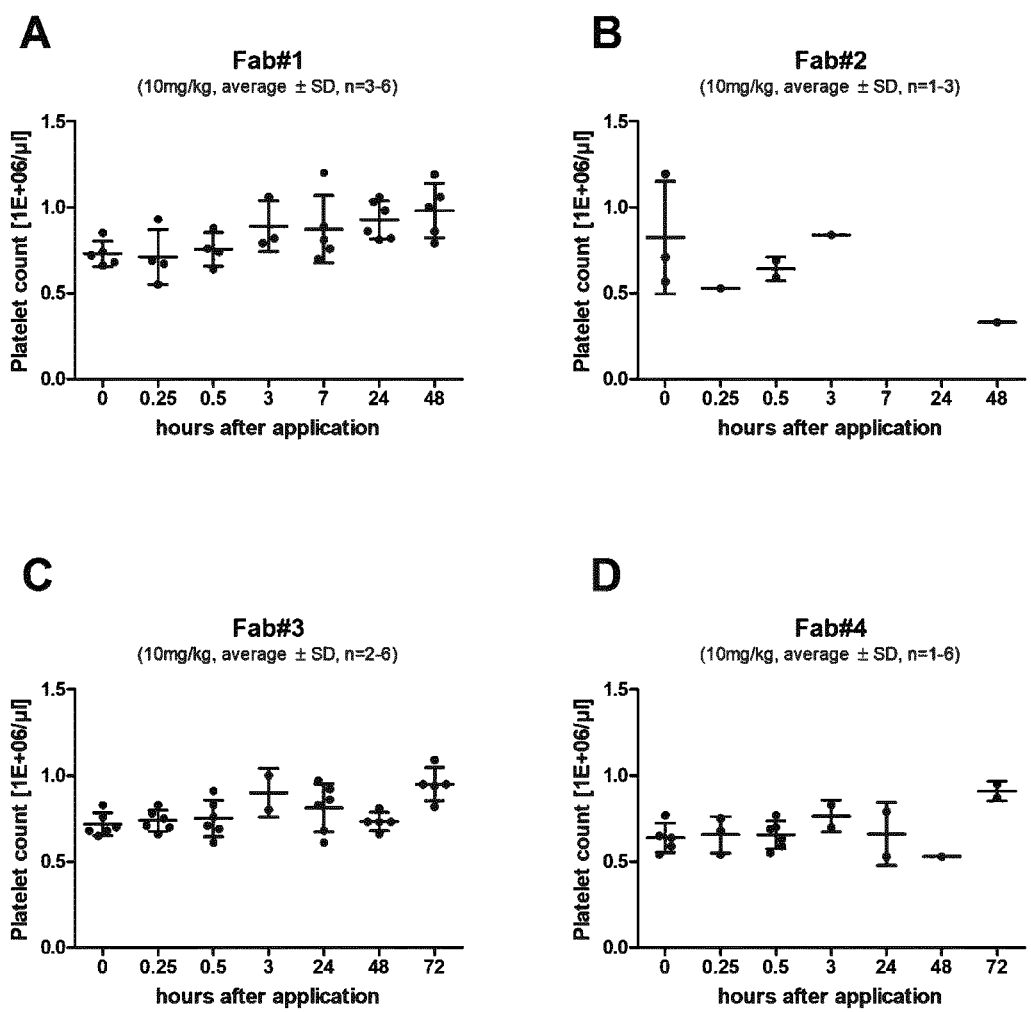
FIG. 9: A-D) Effect of anti-GPVI Fabs on platelet count after i.v. bolus administration of 10 mg/kg anti-GPVI Fab (comprising a modified heavy chain constant region) (Fab #1, Fab #2, Fab #3 and Fab #4) into C57BL/6J mice: Shown are average platelet numbers±SD at different time points from 1-6 mice per treatment group.

As shown in FIG. 9, no indication of thrombocytopenia after 48 or 72 hours and administration of 10 mg/kg anti GPVI Fab comprising a modified heavy chain constant region (Fab #1, Fab #2, Fab #3 or Fab #4) was observable. This indicates, that treatment with the anti-GPVI Fabs of the present disclosure has no deleterious effect on homeostasis, and is in line with the observed absence of bleeding time prolongation as described above (Example 13).

Example 16: GPVI Surface Expression on Platelets

Materials and Methods

Treatment of platelets with anti-GPVI antibodies might induce GPVI internalization or its shedding form the platelet surface which might be indicative for an agonistic activity of the compound and thus unwanted platelet activation. To rule this out, 10 mg/kg anti-GPVI Fab comprising a modified heavy chain constant region (Fab #1, Fab #2, Fab #3 and Fab #4) (comprising heavy and light chain sequences according Table 12) and controls were injected i.v. into the tail vein of CD-1 mice. Directly prior to and at certain time-points after compound injection blood samples were collected from the tail vein contralateral to the vein used for drug application. Blood samples were collected in end-to-end capillary 30 µl K2E tubes (Sanguis Counting). The blood was immediately transferred from the capillaries into a tube containing 1 µl of a 30× coagulation and platelet inhibitor mix (54 mg/ml K2-EDTA, 10 mg/ml acetylsalicylic acid (ASA), 167 µg/ml Ticagrelor and 3 pg/ml PGI2). Blood was diluted 1:20 in Tyrode's buffer (pH 7.3) containing APC-conjugated anti-CD41 antibody (Biolegend) and a PE-conjugated non-competing anti-GPVI Fab (in-house) and incubated for 10 min at RT in the dark. Subsequently, samples were further diluted 1:25 in PBS and analyzed in a BD FACS CANTO' II (BD Biosciences). PE signal of the CD41-positive population was converted into absolute numbers of GPVI molecules per platelet using Quantibrite™ PE Fluorescence Quantitation KIT (BD Biosciences).

Results and Conclusion

Figure 10:
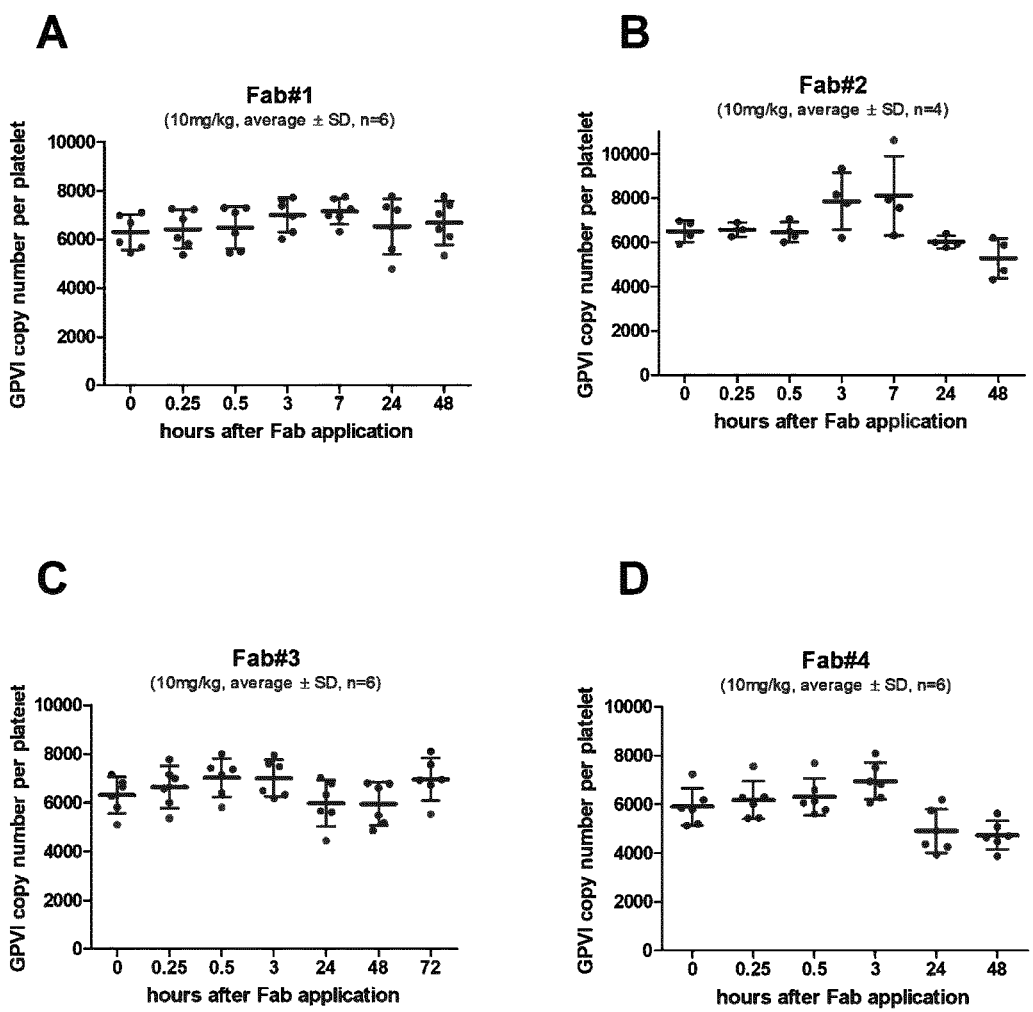
FIG. 10: A-D) Evaluation of GPVI surface expression on mouse platelets after i.v. bolus administration of 10 mg/kg anti-GPVI Fab (comprising a modified human heavy chain constant region) (Fab #1, Fab #2, Fab #3 or Fab #4) into CD-1 mice. Shown are average GPVI copy numbers±SD at different time points of 4-6 mice per treatment group.

As depicted in FIG. 10, administration of 10 mg/kg GPVI Fab (Fab #1, Fab #2, Fab #3, Fab #4) comprising a modified heavy chain constant region did not resulted in the reduction of GPVI on the platelet surface within 48 or 72 h after administration of Fab #1, Fab #2, and Fab #3. Platelets from mice treated with Fab #4 showed a slight reduction of GPVI copy number of −20% on their cell surface after 24 and 48 h. This indicates that the tested Fabs do no or only slightly induce shedding or internalization of GPVI. In line with the results observed in the CD62P platelet activation FACS (Example 13), this further confirms that the tested Fabs have no intrinsic agonistic, platelet activating capacity.

Example 17: ELISA-Based Cross-Competition Assay

Cross-competition of an antibody or antibody fragment specific for GPVI or another GPVI binding agent may be detected by using an ELISA assay according to the following standard procedure.

The general principle of the ELISA-assay involves coating of an GPVIP specific antibody or antibody fragment (such as Fab #1, Fab #2, Fab #3, Fab #1) onto the wells of an ELISA plate. An excess amount of a second, potentially cross-competitive, antibody specific for GPVI is then added in solution (i.e. not bound to the ELISA plate). Subsequently a limited amount of GPVI-Fc is then added to the wells. The antibody which is coated onto the wells and the antibody in solution will compete for binding of the limited number of GPVI molecules. The plate is then washed to remove GPVI molecules that has not bound to the coated antibody and to also remove the second, solution phase antibody as well as any complexes formed between the second, solution phase antibody and GPVI. The amount of bound GPVI is then measured using an appropriate GPVI detection reagent. Therefore, GPVI may be fused with a tag, e.g. Fc, Flag, etc. which can be detected via an appropriate tag-specific agent.

An antibody in solution that is cross-competitive to the coated antibody will be able to cause a decrease in the number of GPVI molecules that the coated antibody can bind relative to the number of GPVI molecules that the coated antibody can bind in the absence of the second, solution phase antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y GPVI binding sites per well are at least 10 fold higher than the moles of Ab-X GPVI binding sites that are used, per well, during the coating of the ELISA plate. GPVI is added such that the moles of GPVI added per well were at least 25-fold lower than the moles of Ab-X GPVI binding sites that are used for coating each well. Following a suitable incubation period, the ELISA plate is washed and a detection reagent specific for the GPVI antigen is added to measure the amount of GPVI molecules specifically bound by the coated antibody specific for GPVI (in this case Ab-X). The background signal for the assay is defined as the signal obtained in wells with the coated antibody (in this case Ab-X), second solution phase antibody (in this case Ab-Y), buffer only (i.e. no GPVI) and detection reagents. The positive control signal for the assay is defined as the signal obtained in wells with the coated antibody (in this case Ab-X), second solution phase antibody buffer only (i.e. no second solution phase antibody), GPVI detection reagents. The ELISA assay needs to be run in such a manner so as to have the positive control signal be at least 6 times the background signal.

To avoid any artifacts (e.g. significantly different affinities between Ab-X and Ab-Y for IL-17C) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

The invention claimed is:

1. An antibody or antibody fragment specific for GPVI, wherein said antibody or antibody fragment comprises
   a) the HCDR1 region of SEQ ID NO: 11, the HCDR2 region of SEQ ID NO: 12, the HCDR3 region of SEQ ID NO: 13, the LCDR1 region of SEQ ID NO: 14, the LCDR2 region of SEQ ID NO: 15 and the LCDR3 region of SEQ ID NO: 16, or
   b) the HCDR1 region of SEQ ID NO: 22, the HCDR2 region of SEQ ID NO: 23, the HCDR3 region of SEQ ID NO: 24, the LCDR1 region of SEQ ID NO: 25, the LCDR2 region of SEQ ID NO: 26 and the LCDR3 region of SEQ ID NO: 27, or
   c) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38, or
   d) the HCDR1 region of SEQ ID NO: 44, the HCDR2 region of SEQ ID NO: 45, the HCDR3 region of SEQ ID NO: 46, the LCDR1 region of SEQ ID NO: 47, the LCDR2 region of SEQ ID NO: 48 and the LCDR3 region of SEQ ID NO: 49.

2. An antibody or antibody fragment according to claim 1, wherein said antibody or antibody fragment comprises
   a) the VH of SEQ ID NO: 17 and the VL of SEQ ID NO: 18, or
   b) the VH of SEQ ID NO: 28 and the VL of SEQ ID NO: 29, or
   c) the VH of SEQ ID NO: 39 and the VL of SEQ ID NO: 40, or
   d) the VH of SEQ ID NO: 50 and the VL of SEQ ID NO: 51.

3. An antibody or antibody fragment according to claim 1, wherein said antibody or antibody fragment comprises
   a) the HC of SEQ ID NO: 20 and the LC of SEQ ID NO: 19, or
   b) the HC of SEQ ID NO: 21 and the LC of SEQ ID NO: 19, or
   c) the HC of SEQ ID NO: 31 and the LC of SEQ ID NO: 30, or
   d) the HC of SEQ ID NO: 32 and the LC of SEQ ID NO: 30, or
   e) the HC of SEQ ID NO: 42 and the LC of SEQ ID NO: 41, or
   f) the HC of SEQ ID NO: 43 and the LC of SEQ ID NO: 41, or
   g) the HC of SEQ ID NO: 53 and the LC of SEQ ID NO: 52, or
   h) the HC of SEQ ID NO: 53 and the LC of SEQ ID NO: 54.

4. An antibody or antibody fragment according to claim 1, wherein said antibody or antibody fragment is a human, humanized, chimeric or synthetic antibody or antibody fragment.

5. An antibody or antibody fragment according to claim 1, wherein said antibody or antibody fragment is an isolated antibody or antibody fragment.

6. An antibody or antibody fragment according to claim 1, wherein said antibody or antibody fragment is a recombinant antibody or antibody fragment.

7. An antibody or antibody fragment according to claim 1, wherein said antibody or antibody fragment is a monoclonal antibody or antibody fragment.

8. An antibody or antibody fragment according to claim 1, wherein said antibody or antibody fragment is a monovalent antibody or antibody fragment.

9. An antibody fragment according to claim 8, wherein said monovalent antibody fragment is a Fab.

10. An antibody or antibody fragment according to claim 9, wherein said Fib comprises a modified heavy chain constant region, wherein the modified heavy chain constant region comprises the amino acid sequence ASTKGPSVFPLAPSSKSTSGGTAALGCLVKDYF-PEPVTVSWNSGALTSGVHTFPAVL QSSGLYS-LSSVVTVPSSSLGTQTYICNVNHKPSNTKVDKEVERR QGGIGHKC (SEQ ID NO: 113 and wherein the modified heavy chain constant region inhibits recognition of said Fab by anti-Fab antibodies present in a subject's serum.

11. An antibody or antibody fragment according to claim 10, wherein the modified heavy chain constant region consists of the amino acid sequence

```
                                          (SEQ ID NO: 113)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKEVER

RQGGIGHKC.
```

12. An antibody or antibody fragment according to claim 1, wherein said antibody or antibody fragment is specific for human GPVI, cynomolgus monkey GPVI, mouse GPVI and rat GPVI.

13. An antibody or antibody fragment according to claim 1 for use in medicine.

14. An antibody or antibody fragment according to claim 1 for use in the treatment of a subject in need thereof.

15. A nucleic acid composition comprising a nucleic acid sequence or a plurality of nucleic acid sequences encoding the antibody or antibody fragment according to claim 1.

16. A vector composition comprising a vector or a plurality of vectors comprising the nucleic acid sequence or plurality of nucleic acid sequences of claim 15.

17. A host cell comprising the vector composition of claim 16.

18. A pharmaceutical composition comprising an isolated antibody or antibody fragment according to claim 1 and a pharmaceutically acceptable carrier or excipient.

* * * * *

SEQUENCE LISTING

<160> NUMBER OF SEQ ID NOS: 113

<210> SEQ ID NO 1
<211> LENGTH: 339
<212> TYPE: PRT
<213> ORGANISM: Homo sapiens

<400> SEQUENCE: 1

```
Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
    210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270

Ile Cys Leu Gly Ala Val Ile Leu Ile Leu Ala Gly Phe Leu Ala
        275                 280                 285

Glu Asp Trp His Ser Arg Arg Lys Arg Leu Arg His Arg Gly Arg Ala
    290                 295                 300

Val Gln Arg Pro Leu Pro Pro Leu Pro Pro Leu Pro Leu Thr Arg Lys
305                 310                 315                 320

Ser Asn Gly Gly Gln Asp Gly Arg Gln Asp Val His Ser Arg Gly
                325                 330                 335

Leu Cys Ser
```

<210> SEQ ID NO 2
<211> LENGTH: 318
<212> TYPE: PRT
<213> ORGANISM: Macaca fascicularis

<400> SEQUENCE: 2

```
Met Ser Pro Ser Pro Thr Thr Leu Phe Cys Leu Gly Leu Cys Leu Gly
1               5                   10                  15
```

His Val Pro Ala Gln Arg Gly Pro Leu Pro Lys Pro Ser Leu Gln Ala
                20                  25                  30

Leu Pro Ser Ser Leu Val Pro Leu Glu Lys Pro Val Thr Leu Arg Cys
            35                  40                  45

Gln Gly Pro Pro Gly Val Asp Leu Tyr Arg Leu Glu Lys Leu Ser Ser
 50                  55                  60

Ser Arg Tyr Gln Asp Gln Ala Val Leu Phe Ile Pro Ala Met Lys Arg
65                  70                  75                  80

His Leu Ala Gly Arg Tyr Arg Cys Ser Tyr Gln Asn Gly Ser Leu Trp
                85                  90                  95

Ser Pro Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
            115                 120                 125

Asp Val Thr Leu Gln Cys Gln Thr Arg Tyr Gly Phe Asp Gln Phe Ala
            130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Gly Asp Pro Tyr Leu Trp Ser
            180                 185                 190

Ala Pro Ser Asp Pro Leu Glu Leu Met Val Thr Glu Phe Ser Glu Ala
            195                 200                 205

Thr Thr Glu Leu Thr Val Ser Leu Thr Asn Lys Val Phe Thr Thr Glu
            210                 215                 220

Thr Ser Arg Ser Ile Thr Ala Ser Pro Lys Glu Pro Gly Ser Pro Ala
225                 230                 235                 240

Gly Pro Ala Arg Gln Tyr Tyr Thr Lys Gly Asn Leu Val Arg Ile Cys
                245                 250                 255

Leu Gly Ala Val Ile Leu Ile Leu Leu Ala Gly Phe Leu Ala Glu Asp
            260                 265                 270

Trp His Ser Arg Arg Lys Arg Leu Arg His Arg Val Arg Ala Val Gln
            275                 280                 285

Arg Pro Leu Pro Pro Leu Pro Pro Thr Arg Lys Ser His Gly Asp Gln
290                 295                 300

Asp Gly Gly Arg Pro Asp Val His Ser Arg Gly Leu Cys Ser
305                 310                 315

<210> SEQ ID NO 3
<211> LENGTH: 313
<212> TYPE: PRT
<213> ORGANISM: Mus musculus

<400> SEQUENCE: 3

Met Ser Pro Ala Ser Pro Thr Phe Phe Cys Ile Gly Leu Cys Val Leu
1               5                   10                  15

Gln Val Ile Gln Thr Gln Ser Gly Pro Leu Pro Lys Pro Ser Leu Gln
                20                  25                  30

Ala Gln Pro Ser Ser Leu Val Pro Leu Gly Ser Val Ile Leu Arg
            35                  40                  45

Cys Gln Gly Pro Pro Asp Val Asp Leu Tyr Arg Leu Glu Lys Leu Lys
 50                  55                  60

Pro Glu Lys Tyr Glu Asp Gln Asp Phe Leu Phe Ile Pro Thr Met Glu
65                  70                  75                  80

```
Arg Ser Asn Ala Gly Arg Tyr Arg Cys Ser Tyr Gln Asn Gly Ser His
                85                  90                  95

Trp Ser Leu Pro Ser Asp Gln Leu Glu Leu Ile Ala Thr Gly Val Tyr
            100                 105                 110

Ala Lys Pro Ser Leu Ser Ala His Pro Ser Ser Ala Val Pro Gln Gly
        115                 120                 125

Arg Asp Val Thr Leu Lys Cys Gln Ser Pro Tyr Ser Phe Asp Glu Phe
    130                 135                 140

Val Leu Tyr Lys Glu Gly Asp Thr Gly Ser Tyr Lys Arg Pro Glu Lys
145                 150                 155                 160

Trp Tyr Arg Ala Asn Phe Pro Ile Ile Thr Val Thr Ala Ala His Ser
                165                 170                 175

Gly Thr Tyr Arg Cys Tyr Ser Phe Ser Ser Ser Pro Tyr Leu Trp
            180                 185                 190

Ser Ala Pro Ser Asp Pro Leu Val Leu Val Val Thr Gly Leu Ser Ala
        195                 200                 205

Thr Pro Ser Gln Val Pro Thr Glu Glu Ser Phe Pro Val Thr Glu Ser
    210                 215                 220

Ser Arg Arg Pro Ser Ile Leu Pro Thr Asn Lys Ile Ser Thr Thr Glu
225                 230                 235                 240

Lys Pro Met Asn Ile Thr Ala Ser Pro Glu Gly Leu Ser Pro Pro Phe
                245                 250                 255

Gly Phe Ala His Gln His Tyr Ala Lys Gly Asn Leu Val Arg Ile Cys
            260                 265                 270

Leu Gly Ala Thr Ile Ile Ile Ile Leu Leu Gly Leu Leu Ala Glu Asp
        275                 280                 285

Trp His Ser Arg Lys Cys Leu Gln His Arg Met Arg Ala Leu Gln
    290                 295                 300

Arg Pro Leu Pro Pro Leu Pro Leu Ala
305                 310

<210> SEQ ID NO 4
<211> LENGTH: 249
<212> TYPE: PRT
<213> ORGANISM: Homo sapiens

<400> SEQUENCE: 4

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
```

```
                130             135             140
Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
            195                 200                 205

Glu Leu Thr Val Ser Phe Thr Asn Lys Val Phe Thr Thr Glu Thr Ser
        210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn
                245

<210> SEQ ID NO 5
<211> LENGTH: 249
<212> TYPE: PRT
<213> ORGANISM: Homo sapiens

<400> SEQUENCE: 5

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg Ser Leu Ala Gly
        50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
        130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Pro Val Ala Glu Phe Ser Glu Ala Thr Ala
            195                 200                 205

Glu Leu Thr Val Ser Phe Thr Asn Glu Val Phe Thr Thr Glu Thr Ser
        210                 215                 220

Arg Ser Ile Thr Ala Ser Pro Lys Glu Ser Asp Ser Pro Ala Gly Pro
225                 230                 235                 240

Ala Arg Gln Tyr Tyr Thr Lys Gly Asn
                245
```

<210> SEQ ID NO 6
<211> LENGTH: 231
<212> TYPE: PRT
<213> ORGANISM: Homo sapiens

<400> SEQUENCE: 6

```
Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg Ser Leu Ala Gly
        50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
        130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Glu Phe Ser Glu Ala Thr Ala Glu Leu
                180                 185                 190

Thr Val Ser Phe Thr Asn Lys Val Phe Thr Thr Glu Thr Ser Arg Ser
            195                 200                 205

Ile Thr Thr Ser Pro Lys Glu Ser Asp Ser Pro Ala Gly Pro Ala Arg
        210                 215                 220

Gln Tyr Tyr Thr Lys Gly Asn
225                 230
```

<210> SEQ ID NO 7
<211> LENGTH: 229
<212> TYPE: PRT
<213> ORGANISM: Macaca fascicularis

<400> SEQUENCE: 7

```
Gln Arg Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg His Leu Ala Gly
        50                  55                  60

Arg Tyr Arg Cys Ser Tyr Gln Asn Gly Ser Leu Trp Ser Pro Pro Ser
65                  70                  75                  80

Asp Gln Leu Glu Leu Val Ala Thr Gly Val Phe Ala Lys Pro Ser Leu
                85                  90                  95
```

```
Ser Ala Gln Pro Gly Pro Ala Val Ser Ser Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
130                 135                 140

Phe Pro Ile Ile Thr Val Thr Ala Ala His Ser Gly Thr Tyr Arg Cys
145                 150                 155                 160

Tyr Ser Phe Ser Ser Gly Asp Pro Tyr Leu Trp Ser Ala Pro Ser Asp
                165                 170                 175

Pro Leu Glu Leu Met Val Thr Glu Phe Ser Glu Ala Thr Thr Glu Leu
            180                 185                 190

Thr Val Ser Leu Thr Asn Lys Val Phe Thr Thr Glu Thr Ser Arg Ser
        195                 200                 205

Ile Thr Ala Ser Pro Lys Glu Pro Gly Ser Pro Ala Gly Pro Ala Arg
    210                 215                 220

Gln Tyr Tyr Thr Lys
225

<210> SEQ ID NO 8
<211> LENGTH: 246
<212> TYPE: PRT
<213> ORGANISM: Mus musculus

<400> SEQUENCE: 8

Gln Ser Gly Pro Leu Pro Lys Pro Ser Leu Gln Ala Gln Pro Ser Ser
1               5                   10                  15

Leu Val Pro Leu Gly Gln Ser Val Ile Leu Arg Cys Gln Gly Pro Pro
            20                  25                  30

Asp Val Asp Leu Tyr Arg Leu Glu Lys Leu Lys Pro Gln Lys Tyr Glu
        35                  40                  45

Asp Gln Asp Phe Leu Phe Ile Pro Thr Met Glu Arg Ser Asn Ala Gly
    50                  55                  60

Arg Tyr Arg Cys Ser Tyr Gln Asn Gly Ser His Trp Ser Leu Pro Ser
65                  70                  75                  80

Asp Gln Leu Glu Leu Ile Ala Thr Gly Val Tyr Ala Lys Pro Ser Leu
                85                  90                  95

Ser Ala His Pro Ser Ser Ala Val Pro Gln Gly Arg Asp Val Thr Leu
            100                 105                 110

Lys Cys Gln Ser Pro Tyr Ser Phe Asp Glu Phe Val Leu Tyr Lys Glu
        115                 120                 125

Gly Asp Thr Gly Ser Tyr Lys Arg Pro Glu Lys Trp Tyr Arg Ala Asn
130                 135                 140

Phe Pro Ile Ile Thr Val Thr Ala Ala His Ser Gly Thr Tyr Arg Cys
145                 150                 155                 160

Tyr Ser Phe Ser Ser Ser Pro Tyr Leu Trp Ser Ala Pro Ser Asp
                165                 170                 175

Pro Leu Val Leu Val Val Thr Gly Leu Ser Ala Thr Pro Ser Gln Val
            180                 185                 190

Pro Thr Glu Glu Ser Phe Pro Val Thr Glu Ser Ser Arg Arg Pro Ser
        195                 200                 205

Ile Leu Pro Thr Asn Lys Ile Ser Thr Thr Glu Lys Pro Met Asn Ile
    210                 215                 220

Thr Ala Ser Pro Glu Gly Leu Ser Pro Pro Phe Gly Phe Ala His Gln
225                 230                 235                 240
```

His Tyr Ala Lys Gly Asn
                245

<210> SEQ ID NO 9
<211> LENGTH: 248
<212> TYPE: PRT
<213> ORGANISM: Rattus norvegicus

<400> SEQUENCE: 9

Gln His Gly Pro Leu Pro Lys Pro Ser Leu Gln Ala Gln Pro Ser Ser
1               5                   10                  15

Leu Val Pro Leu Gly His Pro Val Thr Leu Arg Cys Leu Gly Pro Ser
            20                  25                  30

Asp Ala Asp Leu Tyr Arg Leu Glu Lys Val Lys Pro Gly Lys Leu Ile
        35                  40                  45

Phe Ile Asp Gln Asp Phe Leu Phe Ile Pro Ile Met Glu Ile Asn Asn
    50                  55                  60

Ala Gly Arg Tyr Arg Cys Ser Tyr Gln Asn Glu Ser His Trp Ser Leu
65                  70                  75                  80

Pro Ser Asp Gln Leu Glu Leu Ile Ala Thr Gly Val Tyr Ser Lys Pro
                85                  90                  95

Ser Leu Ser Ala His Pro Ser Ser Ala Ile Pro Pro Gly Arg Asp Val
            100                 105                 110

Thr Leu Lys Cys Gln Ser Gln Tyr Ser Phe Asp Glu Phe Val Leu Tyr
        115                 120                 125

Lys Glu Gly Asp Thr Arg Pro Tyr Lys Arg Pro Glu Lys Trp Tyr Arg
    130                 135                 140

Ala Asn Phe Pro Val Ile Thr Val Thr Ala Ala His Ser Gly Thr Tyr
145                 150                 155                 160

Arg Cys Tyr Ser Phe Ser Ser Ser Pro Tyr Leu Trp Ser Ala Pro
                165                 170                 175

Ser Asp Pro Leu Val Val Val Thr Gly Pro Ser Ala Thr Pro Ser
            180                 185                 190

Gln Val Pro Thr Glu Val Pro Ser Pro Met Thr Glu Ala Ser Arg Arg
        195                 200                 205

Pro Ser Met Leu Leu Thr Asn Lys Ile Ser Thr Glu Lys Pro Met
    210                 215                 220

Asn Ile Thr Val Ser Pro Glu Gly Pro Ser Pro Phe Gly Phe Ala
225                 230                 235                 240

His Gln His Tyr Ala Lys Gly Asn
                245

<210> SEQ ID NO 10
<211> LENGTH: 228
<212> TYPE: PRT
<213> ORGANISM: Homo sapiens

<400> SEQUENCE: 10

Asp Ile Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 11
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser His Tyr Met His
1               5

<210> SEQ ID NO 12
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Leu Ile Glu Pro Ser Glu Gly Glu Thr Glu Tyr Ala Gln Arg Phe Gln
1               5                   10                  15

Gly

<210> SEQ ID NO 13
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Asp Ser Ser Arg Ser Tyr Pro Leu Gly Phe Asp Ile

```
1               5                  10
```

<210> SEQ ID NO 14
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

```
Ser Gly Ser Ser Ser Asn Ile Gly Asn Asn Tyr Val Ser
1               5                   10
```

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

```
Asp Asn Asn Lys Arg Pro Ser
1               5
```

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

```
Ala Ala Trp Asp Phe Arg Ser Ser Arg Trp Val
1               5                   10
```

<210> SEQ ID NO 17
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Leu Ile Glu Pro Ser Glu Gly Glu Thr Glu Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Arg Ser Tyr Pro Leu Gly Phe Asp Ile Trp Gly
            100                 105                 110
```

```
Gln Gly Thr Leu Val Thr Val Ser Ser
        115                 120
```

<210> SEQ ID NO 18
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Glu Asp Glu Ala Asp Tyr Tyr Cys Ala Ala Trp Asp Phe Arg Ser
                85                  90                  95

Ser Arg Trp Val Phe Gly Gly Gly Thr Lys Leu Thr Val Leu Gly Gln
            100                 105                 110
```

<210> SEQ ID NO 19
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Glu Asp Glu Ala Asp Tyr Tyr Cys Ala Ala Trp Asp Phe Arg Ser
                85                  90                  95

Ser Arg Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

-continued

```
Ala Gly Val Glu Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 20
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Leu Ile Glu Pro Ser Glu Gly Thr Glu Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Arg Ser Tyr Pro Leu Gly Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

<210> SEQ ID NO 21
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Val Gln Leu Val Gln Ser Gly Ala Glu Val Lys Lys Pro Gly Ala
```

```
                1               5                  10                  15
            Ser Val Lys Val Ser Cys Lys Ala Ser Gly Tyr Thr Phe Thr Ser His
                           20                  25                  30
            Tyr Met His Trp Val Arg Gln Ala Pro Gly Gln Gly Leu Glu Trp Met
                           35                  40                  45
            Gly Leu Ile Glu Pro Ser Glu Gly Thr Glu Tyr Ala Gln Arg Phe
                50                  55                  60
            Gln Gly Arg Val Thr Met Thr Arg Asp Thr Ser Thr Ser Thr Val Tyr
             65                  70                  75                  80
            Met Glu Leu Ser Ser Leu Arg Ser Glu Asp Thr Ala Val Tyr Tyr Cys
                           85                  90                  95
            Ala Arg Asp Ser Ser Arg Ser Tyr Pro Leu Gly Phe Asp Ile Trp Gly
                          100                 105                 110
            Gln Gly Thr Leu Val Thr Val Ser Ala Ser Thr Lys Gly Pro Ser
                          115                 120                 125
            Val Phe Pro Leu Ala Pro Ser Ser Lys Ser Thr Ser Gly Gly Thr Ala
            130                 135                 140
            Ala Leu Gly Cys Leu Val Lys Asp Tyr Phe Pro Glu Pro Val Thr Val
            145                 150                 155                 160
            Ser Trp Asn Ser Gly Ala Leu Thr Ser Gly Val His Thr Phe Pro Ala
                          165                 170                 175
            Val Leu Gln Ser Ser Gly Leu Tyr Ser Leu Ser Ser Val Val Thr Val
                          180                 185                 190
            Pro Ser Ser Ser Leu Gly Thr Gln Thr Tyr Ile Cys Asn Val Asn His
                          195                 200                 205
            Lys Pro Ser Asn Thr Lys Val Asp Lys Glu Val Glu Arg Arg Gln Gly
                          210                 215                 220
            Gly Ile Gly His Lys Cys
            225                 230

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asp His Tyr Met Ser
1               5

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Val Gly Ser Glu Gly Lys Phe Ile Asp Tyr Ala Ala Ser Val Lys
1               5                   10                  15
Gly

<210> SEQ ID NO 24
<211> LENGTH: 14
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

His Tyr Arg Glu Phe Arg Trp His Tyr Tyr Tyr Phe Asp Tyr
1               5                   10

<210> SEQ ID NO 25
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Thr Gly Ser Ser Ser Asn Ile Gly Ala Gly Tyr Asp Val His
1               5                   10

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Asn Ser Asn Arg Pro Ser
1               5

<210> SEQ ID NO 27
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gln Ser His Asp Leu Gly Ala His Val Trp Val
1               5                   10

<210> SEQ ID NO 28
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asp His
                20                  25                  30

Tyr Met Ser Trp Ile Arg Gln Ala Pro Gly Lys Gly Leu Glu Trp Val
            35                  40                  45

Ser Ser Val Gly Ser Glu Gly Lys Phe Ile Asp Tyr Ala Ala Ser Val
```

```
                    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                    85                  90                  95

Ala Arg His Tyr Arg Glu Phe Arg Trp His Tyr Tyr Phe Asp Tyr
                100                 105                 110

Trp Gly Gln Gly Thr Leu Val Thr Val Ser Ser
            115                 120

<210> SEQ ID NO 29
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser His Asp Leu Gly
                85                  90                  95

Ala His Val Trp Val Phe Gly Gly Gly Thr Lys Leu Thr Val Leu Gly
                100                 105                 110

Gln

<210> SEQ ID NO 30
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser His Asp Leu Gly
                85                  90                  95
```

```
Ala His Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
        210                 215
```

<210> SEQ ID NO 31
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asp His
            20                  25                  30

Tyr Met Ser Trp Ile Arg Gln Ala Pro Gly Lys Gly Leu Glu Trp Val
        35                  40                  45

Ser Ser Val Gly Ser Glu Gly Lys Phe Ile Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Arg Glu Phe Arg Trp His Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys
```

<210> SEQ ID NO 32
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asp His
            20                  25                  30

Tyr Met Ser Trp Ile Arg Gln Ala Pro Gly Lys Gly Leu Glu Trp Val
        35                  40                  45

Ser Ser Val Gly Ser Glu Gly Lys Phe Ile Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Arg Glu Phe Arg Trp His Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Glu Val Glu Arg Arg
    210                 215                 220

Gln Gly Gly Ile Gly His Lys Cys
225                 230
```

<210> SEQ ID NO 33
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

```
Asp Tyr Tyr Val Ser
1               5
```

<210> SEQ ID NO 34
<211> LENGTH: 17
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 34

Ala Ile Gly Gly Ser Gly Ser Ala Val Gln Tyr Ala Glu Ser Val Lys
1               5                   10                  15

Gly

<210> SEQ ID NO 35
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

His Tyr Arg Glu Phe Arg Trp His Tyr Tyr Tyr Phe Asp Tyr
1               5                   10

<210> SEQ ID NO 36
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Thr Gly Ser Ser Ser Asn Ile Gly Ala Gly Tyr Asp Val His
1               5                   10

<210> SEQ ID NO 37
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Asn Ser Asn Arg Pro Ser
1               5

<210> SEQ ID NO 38
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gln Ser His Asp Leu Gly Ala His Val Trp Val
1               5                   10

<210> SEQ ID NO 39
<211> LENGTH: 123
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic polypeptide"

<400> SEQUENCE: 39

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Gly Asp Tyr
            20                  25                  30

Tyr Val Ser Trp Ile Arg Gln Ala Pro Gly Lys Gly Leu Glu Trp Val
        35                  40                  45

Ser Ala Ile Gly Gly Ser Gly Ser Ala Val Gln Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Arg Glu Phe Arg Trp His Tyr Tyr Tyr Phe Asp Tyr
            100                 105                 110

Trp Gly Gln Gly Thr Leu Val Thr Val Ser Ser
        115                 120

<210> SEQ ID NO 40
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 40

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser His Asp Leu Gly
                85                  90                  95

Ala His Val Trp Val Phe Gly Gly Gly Thr Lys Leu Thr Val Leu Gly
            100                 105                 110

Gln

<210> SEQ ID NO 41
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 41

Gln Ser Val Leu Thr Gln Pro Pro Ser Val Ser Gly Ala Pro Gly Gln
1               5                   10                  15

```
Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser His Asp Leu Gly
                85                  90                  95

Ala His Val Trp Val Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 42
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Gly Asp Tyr
                20                  25                  30

Tyr Val Ser Trp Ile Arg Gln Ala Pro Gly Lys Gly Leu Glu Trp Val
            35                  40                  45

Ser Ala Ile Gly Gly Ser Gly Ser Ala Val Gln Tyr Ala Glu Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg His Tyr Arg Glu Phe Arg Trp His Tyr Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
```

```
                145                 150                 155                 160
Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                    180                 185                 190

Thr Val Pro Ser Ser Ser Leu Gly Thr Gln Thr Tyr Ile Cys Asn Val
                    195                 200                 205

Asn His Lys Pro Ser Asn Thr Lys Val Asp Lys Arg Val Glu Pro Lys
                    210                 215                 220

Ser Cys
225

<210> SEQ ID NO 43
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Gly Asp Tyr
                20                  25                  30

Tyr Val Ser Trp Ile Arg Gln Ala Pro Gly Lys Gly Leu Glu Trp Val
                35                  40                  45

Ser Ala Ile Gly Gly Ser Gly Ser Ala Val Gln Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Arg Glu Phe Arg Trp His Tyr Tyr Tyr Phe Asp Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                    180                 185                 190

Thr Val Pro Ser Ser Ser Leu Gly Thr Gln Thr Tyr Ile Cys Asn Val
                    195                 200                 205

Asn His Lys Pro Ser Asn Thr Lys Val Asp Lys Glu Val Glu Arg Arg
                    210                 215                 220

Gln Gly Gly Ile Gly His Lys Cys
225                 230

<210> SEQ ID NO 44
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 44

Ser Ser Tyr Met His
1               5

<210> SEQ ID NO 45
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ile Ile Glu Pro Thr Gly Ala Ser Thr Leu Tyr Ala Gln Arg Phe Gln
1               5                   10                  15

Gly

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Thr Gly Ile Ala Leu Pro Leu Gly Phe Asp Leu
1               5                   10

<210> SEQ ID NO 47
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ser Gly Ser Ser Ser Asn Ile Gly Asn Asn Tyr Val Ser
1               5                   10

<210> SEQ ID NO 48
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Asp Asn Asn Lys Arg Pro Ser
1               5

<210> SEQ ID NO 49
<211> LENGTH: 10
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 49

Ala Ala Trp Ser Thr Arg Phe Arg Trp Val
1               5                   10

<210> SEQ ID NO 50
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Gly Ala Phe Thr Ser Ser
            20                  25                  30

Tyr Met His Trp Val Arg Gln Ala Pro Gly Gln Gly Leu Glu Trp Met
        35                  40                  45

Gly Ile Ile Glu Pro Thr Gly Ala Ser Thr Leu Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Gly Ile Ala Leu Pro Leu Gly Phe Asp Leu Trp Gly Gln
            100                 105                 110

Gly Thr Leu Val Thr Val Ser Ser
        115                 120

<210> SEQ ID NO 51
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Glu Asp Glu Ala Asp Tyr Tyr Cys Ala Ala Trp Ser Thr Arg Phe
                85                  90                  95

Arg Trp Val Phe Gly Gly Gly Thr Lys Leu Thr Val Leu Gly Gln
            100                 105                 110

<210> SEQ ID NO 52

<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Glu Asp Glu Ala Asp Tyr Tyr Cys Ala Ala Trp Ser Thr Arg Phe
                85                  90                  95

Arg Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 53
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Gln Val Gln Leu Val Gln Ser Gly Ala Glu Val Lys Lys Pro Gly Ala
1               5                   10                  15

Ser Val Lys Val Ser Cys Lys Ala Ser Gly Gly Ala Phe Thr Ser Ser
            20                  25                  30

Tyr Met His Trp Val Arg Gln Ala Pro Gly Gln Gly Leu Glu Trp Met
        35                  40                  45

Gly Ile Ile Glu Pro Thr Gly Ala Ser Thr Leu Tyr Ala Gln Arg Phe
    50                  55                  60

Gln Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Thr Gly Ile Ala Leu Pro Leu Gly Phe Asp Leu Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys
            210                 215                 220
```

<210> SEQ ID NO 54
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

```
Gln Val Gln Leu Val Gln Ser Gly Ala Glu Val Lys Lys Pro Gly Ala
1               5                   10                  15

Ser Val Lys Val Ser Cys Lys Ala Ser Gly Gly Ala Phe Thr Ser Ser
            20                  25                  30

Tyr Met His Trp Val Arg Gln Ala Pro Gly Gln Gly Leu Glu Trp Met
            35                  40                  45

Gly Ile Ile Glu Pro Thr Gly Ala Ser Thr Leu Tyr Ala Gln Arg Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Gly Ile Ala Leu Pro Leu Gly Phe Asp Leu Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Glu Val Glu Arg Arg Gln Gly Gly
```

Ile Gly His Lys Cys
225

<210> SEQ ID NO 55
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 55
tcccattaca tgcat                                                    15

<210> SEQ ID NO 56
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 56
ctgatcgagc cctccgaggg agagactgag tatgctcaac ggttccaagg c             51

<210> SEQ ID NO 57
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 57
gacagcagcc gtagctaccc tctgggtttc gatatt                             36

<210> SEQ ID NO 58
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 58
agcggcagca gcagcaacat cggcaacaac tacgttagc                          39

<210> SEQ ID NO 59
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 59
gataacaaca aacgcccgag c                                             21

<210> SEQ ID NO 60
<211> LENGTH: 33
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
gctgcttggg acttccgttc ttctcgttgg gtg                                  33

<210> SEQ ID NO 61
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61
caggtgcagc tggtgcagag cggtgccgaa gtgaaaaaac caggcgccag cgtgaaagtt      60
agctgcaaag ccagcggcta tacctttacc tcccattaca tgcattgggt tcgccaggcc     120
ccaggccagg gtctggaatg gatggggctg atcgagccct ccgagggaga gactgagtat     180
gctcaacggt tccaaggccg cgtgaccatg acccgcgata ccagcaccag caccgtgtat     240
atggaactga gcagcctgcg cagcgaagat accgccgtgt attattgcgc gcgagacagc     300
agccgtagct accctctggg tttcgatatt tggggccagg gcaccctggt tactgtctcg     360
agc                                                                 363

<210> SEQ ID NO 62
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
cagagcgtgc tgacccagcc gccgagcgtt agcgccgcac caggccagaa agtgaccatt      60
agctgtagcg gcagcagcag caacatcggc aacaactacg ttagctggta tcagcagctg     120
ccgggcaccg ccccgaaact gctgatctat gataacaaca aacgcccgag cggcatcccg     180
gatcgcttta gcggtagcaa aagcggcacc agcgccaccc tgggcattac cggcctgcaa     240
accgaagacg aagccgatta ttactgcgct gcttgggact ccgttcttc tcgttgggtg     300 tttggcggcg gtaccaagct gaccgtgctg ggccag                              336

<210> SEQ ID NO 63
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63
cagagcgtgc tgacccagcc gccgagcgtt agcgccgcac caggccagaa agtgaccatt      60
agctgtagcg gcagcagcag caacatcggc aacaactacg ttagctggta tcagcagctg     120
ccgggcaccg ccccgaaact gctgatctat gataacaaca aacgcccgag cggcatcccg     180
gatcgcttta gcggtagcaa aagcggcacc agcgccaccc tgggcattac cggcctgcaa     240
```

```
accgaagacg aagccgatta ttactgcgct gcttgggact tccgttcttc tcgttgggtg    300
tttggcggcg gtaccaagct gaccgtgctg ggccagccca agccgcccc tagcgtgacc    360 ctgttccccc caagcagcga ggaactccag gccaacaagg ccaccctcgt gtgcctgatc    420
agcgacttct accctggcgc cgtgaccgtg gcctggaagg ccgatagcag ccctgtgaag    480
gccggcgtgg aaaccaccac ccccagcaag cagagcaaca caaatacgc cgccagcagc    540 tacctgagcc tgaccccga gcagtggaag tcccacagat cctacagctg ccaggtcaca    600
cacgagggca gcaccgtgga aaagaccgtg gcccccaccg agtgcagc              648
```

<210> SEQ ID NO 64
<211> LENGTH: 672
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64

```
caggtgcagc tggtgcagag cggtgccgaa gtgaaaaaac caggcgccag cgtgaaagtt    60
agctgcaaag ccagcggcta tacctttacc tcccattaca tgcattgggt tcgccaggcc    120
ccaggccagg gtctggaatg gatggggctg atcgagccct ccgagggaga gactgagtat    180
gctcaacggt tccaaggccg cgtgaccatg accgcgata ccagcaccag caccgtgtat    240
atggaactga gcagcctgcg cagcgaagat accgccgtgt attattgcgc gcgagacagc    300
agccgtagct accctctggg tttcgatatt tggggccagg gcaccctggt tactgtctcg    360
agcgccagca caagggacc cagcgtgttc cctctggccc ccagcagcaa gtctacatct    420
ggcggaacag ccgccctggg ctgcctcgtg aaggactact ttcccgagcc cgtgaccgtg    480
tcctggaact ctggcgctct gacaagcggc gtgcacacct tccagccgt gctccagagc    540 agcggcctgt actctctgag cagcgtcgtg acagtgccca gcagctctct gggcacccag    600
acctacatct gcaacgtgaa ccacaagccc agcaacacaa aggtggacaa gcgggtggaa    660
cccaagtcct gc                                                      672
```

<210> SEQ ID NO 65
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65

```
caggtgcagc tggtgcagag cggtgccgaa gtgaaaaaac caggcgccag cgtgaaagtt    60
agctgcaaag ccagcggcta tacctttacc tcccattaca tgcattgggt tcgccaggcc    120
ccaggccagg gtctggaatg gatggggctg atcgagccct ccgagggaga gactgagtat    180
gctcaacggt tccaaggccg cgtgaccatg accgcgata ccagcaccag caccgtgtat    240
atggaactga gcagcctgcg cagcgaagat accgccgtgt attattgcgc gcgagacagc    300
agccgtagct accctctggg tttcgatatt tggggccagg gcaccctggt tactgtctcg    360
agcgccagca caagggacc cagcgtgttc cctctggccc ccagcagcaa gtctacatct    420
ggcggaacag ccgccctggg ctgcctcgtg aaggactact ttcccgagcc cgtgaccgtg    480
```

```
tcctggaact ctggcgctct gacaagcggc gtgcacacct ttccagccgt gctccagagc    540
agcggcctgt actctctgag cagcgtcgtg acagtgccca gcagctctct gggcacccag    600
acctacatct gcaacgtgaa ccacaagccc agcaacacaa aggtggacaa ggaagtcgag    660
cgcagacagg gcggcatcgg ccataaatgc                                     690
```

<210> SEQ ID NO 66
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66

```
gaccattaca tgagc                                                      15
```

<210> SEQ ID NO 67
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67

```
agcgttggga gcgagggcaa attcatcgac tatgctgcaa gcgtgaaagg g              51
```

<210> SEQ ID NO 68
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68

```
cactaccgtg agttccgttg gcactactat tactttgact at                        42
```

<210> SEQ ID NO 69
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69

```
accggcagca gcagcaacat tggcgcaggc tatgatgtgc at                        42
```

<210> SEQ ID NO 70
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70

```
ggcaacagca atcgcccaag c                                               21
```

<210> SEQ ID NO 71
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 71
cagtctcatg acctgggtgc tcatgtttgg gtg                33

<210> SEQ ID NO 72
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 72
caggtgcagc tggtggaaag cggcggtggc ctggtgaaac caggcggtag cctgcgcctg      60
agctgcgccg ccagcgggtt tagcttttcc gaccattaca tgagctggat tcgccaggcc     120
ccaggcaaag gcctggaatg ggttagcagc gttgggagcg agggcaaatt catcgactat     180
gctgcaagcg tgaaagggcg ctttaccatt agcgcgata acgccaaaaa cagcctgtat      240
ctgcaaatga acagcctgcg ggccgaagat accgccgtgt attattgcgc gcgtcactac      300
cgtgagttcc gttggcacta ctattacttt gactattggg gtcagggcac cctggttact     360
gtctcgagc                                                              369

<210> SEQ ID NO 73
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 73
cagagcgtgc tgacccagcc accaagcgtg agcggtgcac caggtcagcg cgtgaccatt      60
agctgcaccg gcagcagcag caacattggc gcaggctatg atgtgcattg gtatcagcag     120
ctgccaggca ccgcaccgaa actgctgatt tatggcaaca gcaatcgccc aagcggtgtg     180
ccggatcgct ttagcggcag caaaagcggc accagcgcca gcctggcgat taccggtctg     240
caagccgaag acgaagccga ttattactgc cagtctcatg acctgggtgc tcatgtttgg     300
gtgtttggcg gcggtaccaa gctgaccgtg ctgggccag                             339

<210> SEQ ID NO 74
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 74
cagagcgtgc tgacccagcc accaagcgtg agcggtgcac caggtcagcg cgtgaccatt      60
agctgcaccg gcagcagcag caacattggc gcaggctatg atgtgcattg gtatcagcag     120

```
ctgccaggca ccgcaccgaa actgctgatt tatggcaaca gcaatcgccc aagcggtgtg    180
ccggatcgct ttagcggcag caaaagcggc accagcgcca gcctggcgat taccggtctg    240
caagccgaag acgaagccga ttattactgc cagtctcatg acctgggtgc tcatgtttgg    300
gtgtttggcg gcggtaccaa gctgaccgtg ctgggccagc ccaaagccgc ccctagcgtg    360
accctgttcc ccccaagcag cgaggaactc caggccaaca aggccaccct cgtgtgcctg    420
atcagcgact ctacccctgg cgccgtgacc gtggcctgga aggccgatag cagccctgtg    480
aaggccggcg tggaaaccac cacccccagc aagcagagca caacaaata cgccgccagc    540 agctacctga gcctgacccc cgagcagtgg aagtcccaca gatcctacag ctgccaggtc    600
acacacgagg gcagcaccgt ggaaaagacc gtggccccca ccgagtgcag c            651
```

<210> SEQ ID NO 75
<211> LENGTH: 678
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75

```
caggtgcagc tggtggaaag cggcggtggc ctggtgaaac caggcggtag cctgcgcctg     60
agctgcgccg ccagcgggtt tagcttttcc gaccattaca tgagctggat tcgccaggcc    120
ccaggcaaag gcctggaatg ggttagcagc gttgggagcg agggcaaatt catcgactat    180
gctgcaagcg tgaaagggcg ctttaccatt agccgcgata cgccaaaaa cagcctgtat    240 ctgcaaatga acagcctgcg ggccgaagat accgccgtgt attattgcgc gcgtcactac    300
cgtgagttcc gttggcacta ctattacttt gactattggg gtcagggcac cctggttact    360
gtctcgagcg ccagcacaaa gggacccagc gtgttccctc tggcccccag cagcaagtct    420
acatctggcg gaacagccgc cctgggctgc ctcgtgaagg actactttcc cgagcccgtg    480
accgtgtcct ggaactctgg cgctctgaca agcggcgtgc acacctttcc agccgtgctc    540
cagagcagcg gcctgtactc tctgagcagc gtcgtgacag tgcccagcag ctctctgggc    600
acccagacct acatctgcaa cgtgaaccac aagcccagca acacaaaggt ggacaagcgg    660
gtggaaccca gtcctgc                                                   678
```

<210> SEQ ID NO 76
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76

```
caggtgcagc tggtggaaag cggcggtggc ctggtgaaac caggcggtag cctgcgcctg     60
agctgcgccg ccagcgggtt tagcttttcc gaccattaca tgagctggat tcgccaggcc    120
ccaggcaaag gcctggaatg ggttagcagc gttgggagcg agggcaaatt catcgactat    180
gctgcaagcg tgaaagggcg ctttaccatt agccgcgata cgccaaaaa cagcctgtat    240 ctgcaaatga acagcctgcg ggccgaagat accgccgtgt attattgcgc gcgtcactac    300
cgtgagttcc gttggcacta ctattacttt gactattggg gtcagggcac cctggttact    360
gtctcgagcg ccagcacaaa gggacccagc gtgttccctc tggcccccag cagcaagtct    420
```

```
acatctggcg gaacagccgc cctgggctgc ctcgtgaagg actactttcc cgagcccgtg    480
accgtgtcct ggaactctgg cgctctgaca agcggcgtgc acacctttcc agccgtgctc    540
cagagcagcg gcctgtactc tctgagcagc gtcgtgacag tgcccagcag ctctctgggc    600
acccagacct acatctgcaa cgtgaaccac aagcccagca acacaaaggt ggacaaggaa    660
gtcgagcgca gacagggcgg catcggccat aaatgc                              696
```

<210> SEQ ID NO 77
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77

```
gactattacg tgagc                                                      15
```

<210> SEQ ID NO 78
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78

```
gccattgggg ggtccggttc cgccgtgcaa tacgctgaat ccgtgaaggg c              51
```

<210> SEQ ID NO 79
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79

```
cactaccgtg agttccgttg gcactactat tactttgact at                        42
```

<210> SEQ ID NO 80
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80

```
accggcagca gcagcaacat tggcgcaggc tatgatgtgc at                        42
```

<210> SEQ ID NO 81
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
ggcaacagca atcgcccaag c                                              21

<210> SEQ ID NO 82
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
cagtctcatg acctgggtgc tcatgtttgg gtg                                 33

<210> SEQ ID NO 83
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
caggtgcagc tggtggaaag cggcggtggc ctggtgaaac caggcggtag cctgcgcctg     60
agctgcgccg ccagcgggtt tagcttcggc gactattacg tgagctggat tcgccaggcc    120
ccaggcaaag gcctggaatg ggttagcgcc attgggggt ccggttccgc cgtgcaatac    180
gctgaatccg tgaagggccg ctttaccatt agccgcgata cgccaaaaa cagcctgtat    240 ctgcaaatga acagcctgcg ggccgaagat accgccgtgt attattgcgc cgtcactac    300 cgtgagttcc gttggcacta ctattacttt gactattggg gtcagggcac cctggttact    360
gtctcgagc                                                            369

<210> SEQ ID NO 84
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
cagagcgtgc tgacccagcc accaagcgtg agcggtgcac caggtcagcg cgtgaccatt     60
agctgcaccg gcagcagcag caacattggc gcaggctatg atgtgcattg gtatcagcag    120
ctgccaggca ccgcaccgaa actgctgatt tatggcaaca gcaatcgccc aagcggtgtg    180
ccggatcgct ttagcggcag caaaagcggc accagcgcca gcctggcgat taccggtctg    240
caagccgaag acgaagccga ttattactgc cagtctcatg acctgggtgc tcatgtttgg    300
gtgtttggcg gcggtaccaa gctgaccgtg ctgggccag                           339

<210> SEQ ID NO 85
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
cagagcgtgc tgacccagcc accaagcgtg agcggtgcac caggtcagcg cgtgaccatt     60

```
agctgcaccg gcagcagcag caacattggc gcaggctatg atgtgcattg gtatcagcag    120
ctgccaggca ccgcaccgaa actgctgatt tatggcaaca gcaatcgccc aagcggtgtg    180
ccggatcgct ttagcggcag caaaagcggc accagcgcca gcctggcgat taccggtctg    240
caagccgaag acgaagccga ttattactgc cagtctcatg acctgggtgc tcatgtttgg    300
gtgtttggcg gcggtaccaa gctgaccgtg ctgggccagc ccaaagccgc ccctagcgtg    360
accctgttcc ccccaagcag cgaggaactc caggccaaca aggccaccct cgtgtgcctg    420
atcagcgact tctaccctgg cgccgtgacc gtggcctgga aggccgatag cagccctgtg    480
aaggccggcg tggaaaccac cacccccagc aagcagagca caacaaata cgccgccagc    540 agctacctga gcctgacccc cgagcagtgg aagtcccaca gatcctacag ctgccaggtc    600
acacacgagg gcagcaccgt ggaaaagacc gtggccccca ccgagtgcag c              651

<210> SEQ ID NO 86
<211> LENGTH: 678
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
caggtgcagc tggtggaaag cggcggtggc ctggtgaaac aggcggtag cctgcgcctg      60 agctgcgccg ccagcgggtt tagcttcggc gactattacg tgagctggat tcgccaggcc    120
ccaggcaaag gcctggaatg ggttagcgcc attgggggt ccggttccgc cgtgcaatac    180
gctgaatccg tgaagggccg ctttaccatt agccgcgata cgccaaaaa cagcctgtat     240 ctgcaaatga acagcctgcg ggccgaagat accgccgtgt attattgcgc gcgtcactac    300
cgtgagttcc gttggcacta ctattacttt gactattggg gtcagggcac cctggttact    360
gtctcgagcg ccagcacaaa gggacccagc gtgttccctc tggcccccag cagcaagtct    420
acatctggcg gaacagccgc cctgggctgc ctcgtgaagg actactttcc cgagcccgtg    480
accgtgtcct ggaactctgg cgctctgaca agcggcgtgc acacctttcc agccgtgctc    540
cagagcagcg gcctgtactc tctgagcagc gtcgtgacag tgcccagcag ctctctgggc    600
acccagacct acatctgcaa cgtgaaccac aagcccagca cacaaaggt ggacaagcgg    660 gtggaaccca gtcctgc                                                    678

<210> SEQ ID NO 87
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87
caggtgcagc tggtggaaag cggcggtggc ctggtgaaac aggcggtag cctgcgcctg      60 agctgcgccg ccagcgggtt tagcttcggc gactattacg tgagctggat tcgccaggcc    120
ccaggcaaag gcctggaatg ggttagcgcc attgggggt ccggttccgc cgtgcaatac    180
gctgaatccg tgaagggccg ctttaccatt agccgcgata cgccaaaaa cagcctgtat     240 ctgcaaatga acagcctgcg ggccgaagat accgccgtgt attattgcgc gcgtcactac    300
```

```
cgtgagttcc gttggcacta ctattacttt gactattggg gtcagggcac cctggttact    360
gtctcgagcg ccagcacaaa gggacccagc gtgttccctc tggcccccag cagcaagtct    420
acatctggcg aacagccgc cctgggctgc ctcgtgaagg actactttcc cgagcccgtg     480
accgtgtcct ggaactctgg cgctctgaca agcggcgtgc acacctttcc agccgtgctc    540
cagagcagcg gcctgtactc tctgagcagc gtcgtgacag tgcccagcag ctctctgggc    600
acccagacct acatctgcaa cgtgaaccac aagcccagca acacaaaggt ggacaaggaa    660
gtcgagcgca gacagggcgg catcggccat aaatgc                              696
```

```
<210> SEQ ID NO 88
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
tccagctaca tgcat                                                     15

<210> SEQ ID NO 89
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
attatcgagc ccactggggc atccacactg tacgcacagc ggttccaagg g             51

<210> SEQ ID NO 90
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
actggaatcg cactgcctct gggttttgac ctg                                 33

<210> SEQ ID NO 91
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
agcggcagca gcagcaacat cggcaacaac tacgttagc                           39

<210> SEQ ID NO 92
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 92
gataacaaca aacgcccgag c                                                 21

<210> SEQ ID NO 93
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
gccgcttgga gtactcgttt ccgttgggtg                                        30

<210> SEQ ID NO 94
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94
caggtgcagc tggtgcagag cggtgccgaa gtgaaaaaac caggcgccag cgtgaaagtt       60
agctgcaaag ccagcggcgg cgcatttacc tccagctaca tgcattgggt tcgccaggcc     120
ccaggccagg gtctggaatg gatgggcatt atcgagccca ctggggcatc cacactgtac     180
gcacagcggt tccaagggcg cgtgaccatg acccgcgata ccagcaccag caccgtgtat     240
atggaactga gcagcctgcg cagcgaagat accgccgtgt attattgcgc gcgaactgga     300
atcgcactgc ctctgggttt tgacctgtgg ggccagggca ccctggttac tgtctcgagc     360

<210> SEQ ID NO 95
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
cagagcgtgc tgacccagcc gccgagcgtt agcgccgcac caggccagaa agtgaccatt       60
agctgtagcg gcagcagcag caacatcggc aacaactacg ttagctggta tcagcagctg     120
ccgggcaccg ccccgaaaact gctgatctat gataacaaca acgcccgag cggcatcccg      180 gatcgcttta gcggtagcaa aagcggcacc agcgccaccc tggcattac cggcctgcaa      240 accgaagacg aagccgatta ttactgtgcc gcttggagta ctcgtttccg ttgggtgttt     300
ggcggcggta ccaagctgac cgtgctgggc cag                                   333

<210> SEQ ID NO 96
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96

| | |
|---|---|
| cagagcgtgc tgacccagcc gccgagcgtt agcgccgcac caggccagaa agtgaccatt | 60 |
| agctgtagcg gcagcagcag caacatcggc aacaactacg ttagctggta tcagcagctg | 120 |
| ccgggcaccg ccccgaaact gctgatctat gataacaaca acgcccgag cggcatcccg | 180 |
| gatcgcttta gcgtagcaa aagcggcacc agcgccaccc tgggcattac cggcctgcaa | 240 |
| accgaagacg aagccgatta ttactgtgcc gcttggagta ctcgtttccg ttgggtgttt | 300 |
| ggcggcggta ccaagctgac cgtgctgggc agcccaaag ccgcccctag cgtgaccctg | 360 |
| ttccccccaa gcagcgagga actccaggcc aacaaggcca ccctcgtgtg cctgatcagc | 420 |
| gacttctacc ctggcgccgt gaccgtggcc tggaaggccg atagcagccc tgtgaaggcc | 480 |
| ggcgtggaaa ccaccacccc cagcaagcag agcaacaaca atacgccgc cagcagctac | 540 |
| ctgagcctga cccccgagca gtggaagtcc cacagatcct acagctgcca ggtcacacac | 600 |
| gagggcagca ccgtggaaaa gaccgtggcc cccaccgagt gcagc | 645 |

<210> SEQ ID NO 97
<211> LENGTH: 669
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97

| | |
|---|---|
| caggtgcagc tggtgcagag cggtgccgaa gtgaaaaaac caggcgccag cgtgaaagtt | 60 |
| agctgcaaag ccagcggcgg cgcatttacc tccagctaca tgcattgggt tcgccaggcc | 120 |
| ccaggccagg gtctggaatg gatgggcatt atcgagccca ctggggcatc cacactgtac | 180 |
| gcacagcggt tccaagggcg cgtgaccatg accgcgata ccagcaccag caccgtgtat | 240 |
| atggaactga gcagcctgcg cagcgaagat accgccgtgt attattgcgc gcgaactgga | 300 |
| atcgcactgc ctctgggttt tgacctgtgg ggccagggca ccctggttac tgtctcgagc | 360 |
| gccagcacaa agggacccag cgtgttccct ctggccccca gcagcaagtc tacatctggc | 420 |
| ggaacagccg ccctgggctg cctcgtgaag gactactttc ccgagcccgt gaccgtgtcc | 480 |
| tggaactctg gcgctctgac aagcggcgtg cacacctttc cagccgtgct ccagagcagc | 540 |
| ggcctgtact ctctgagcag cgtcgtgaca gtgcccagca gctctctggg cacccagacc | 600 |
| tacatctgca acgtgaacca caagcccagc aacacaaagg tggacaagcg ggtggaaccc | 660 |
| aagtcctgc | 669 |

<210> SEQ ID NO 98
<211> LENGTH: 687
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98

| | |
|---|---|
| caggtgcagc tggtgcagag cggtgccgaa gtgaaaaaac caggcgccag cgtgaaagtt | 60 |
| agctgcaaag ccagcggcgg cgcatttacc tccagctaca tgcattgggt tcgccaggcc | 120 |
| ccaggccagg gtctggaatg gatgggcatt atcgagccca ctggggcatc cacactgtac | 180 |
| gcacagcggt tccaagggcg cgtgaccatg accgcgata ccagcaccag caccgtgtat | 240 |
| atggaactga gcagcctgcg cagcgaagat accgccgtgt attattgcgc gcgaactgga | 300 |

```
atcgcactgc ctctgggttt tgacctgtgg ggccagggca ccctggttac tgtctcgagc    360
gccagcacaa agggacccag cgtgttccct ctggccccca gcagcaagtc tacatctggc    420
ggaacagccg ccctgggctg cctcgtgaag gactactttc ccgagcccgt gaccgtgtcc    480
tggaactctg gcgctctgac aagcggcgtg cacacccttc cagccgtgct ccagagcagc    540
ggcctgtact ctctgagcag cgtcgtgaca gtgcccagca gctctctggg cacccagacc    600
tacatctgca acgtgaacca caagcccagc aacacaaagg tggacaagga agtcgagcgc    660
agacagggcg gcatcggcca taaatgc                                       687
```

<210> SEQ ID NO 99
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 99

```
Glu Val Gln Leu Leu Glu Ser Gly Pro Gly Leu Val Ala Pro Ser Gly
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Gln Ser Thr Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Arg Thr Asp Asp Thr Ala Arg Tyr Tyr Cys Ala
                85                  90                  95

Arg Asp Leu Pro Met Asp Tyr Trp Gly Leu Gly Thr Ser Val Thr Val
            100                 105                 110

Ser Ser
```

<210> SEQ ID NO 100
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

```
Asp Ile Gln Met Thr Gln Ser Pro Ser Ser Leu Ser Ala Ser Val Gly
1               5                   10                  15

Gly Arg Val Thr Ile Thr Cys Lys Ala Ser Gln Asp Ile Asn Lys Tyr
            20                  25                  30

Ile Ala Trp Tyr Gln His Lys Pro Gly Lys Gly Pro Ser Leu Leu Ile
        35                  40                  45

His Tyr Thr Ser Thr Leu Gln Pro Gly Val Pro Ser Arg Phe Ser Gly
    50                  55                  60

Ser Gly Ser Gly Arg Asp Tyr Ser Phe Ser Ile Ser Asn Leu Gln Pro
65                  70                  75                  80

Glu Asp Ile Ala Thr Tyr Tyr Cys Leu Gln Tyr Ala Asn Leu Leu Thr
                85                  90                  95
```

Phe Gly Gly Gly Thr Lys Leu Glu Ile Lys Arg Thr
            100                 105

<210> SEQ ID NO 101
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Glu Pro Lys Ser Cys
1               5

<210> SEQ ID NO 102
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(5)
<223> OTHER INFORMATION: Any natural occurring amino acid residue except
      cysteine

<400> SEQUENCE: 102

Glu Arg Arg Xaa Xaa Gly Ile Gly His Lys Cys
1               5                   10

<210> SEQ ID NO 103
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Glu Arg Arg Asn Gly Gly Ile Gly His Lys Cys
1               5                   10

<210> SEQ ID NO 104
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Glu Glu Arg Asn Gly Gly Ile Gly His Lys Cys
1               5                   10

<210> SEQ ID NO 105
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 105

Glu Arg Arg Gln Gly Gly Ile Gly His Lys Cys
1               5                   10

<210> SEQ ID NO 106
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Val Pro Arg Glu Cys
1               5

<210> SEQ ID NO 107
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ile Val Pro Arg Glu Cys
            100

<210> SEQ ID NO 108
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

-continued

Tyr Ile Cys Asn Val Asn His Lys Pro Ser Asn Thr Lys Val Asp Lys
                85                  90                  95

Lys Val Glu Arg Arg Asn Gly Gly Ile Gly His Lys Cys
            100                 105

<210> SEQ ID NO 109
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Glu Lys
                85                  90                  95

Lys Val Glu Arg Arg Asn Gly Gly Ile Gly His Lys Cys
            100                 105

<210> SEQ ID NO 110
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Gly Val Glu Arg Arg Asn Gly Gly Ile Gly His Lys Cys
            100                 105

<210> SEQ ID NO 111
<211> LENGTH: 109
<212> TYPE: PRT
<213> ORGANISM: Artificial Sequence
<220> FEATURE:

<220> FEATURE:
<221> NAME/KEY: source
<223> OTHER INFORMATION: /note="Description of Artificial Sequence: Synthetic polypeptide"

<400> SEQUENCE: 111

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Glu Val Glu Arg Arg Asn Gly Gly Ile Gly His Lys Cys
            100                 105

<210> SEQ ID NO 112
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 112

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Glu Arg Asn Gly Gly Ile Gly His Lys Cys
            100                 105

<210> SEQ ID NO 113
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 113

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

-continued

```
            35                  40                  45
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Glu Val Glu Arg Arg Gln Gly Gly Ile Gly His Lys Cys
                100                 105
```